United States Patent
Ueki et al.

(10) Patent No.: US 10,870,638 B2
(45) Date of Patent: Dec. 22, 2020

(54) PYRIDAZINONE COMPOUND OR ITS SALT, AND HERBICIDE CONTAINING IT

(71) Applicant: ISHIHARA SANGYO KAISHA, LTD., Osaka (JP)

(72) Inventors: Toshihiko Ueki, Osaka (JP); Ryu Yamada, Osaka (JP); Hisaki Tanaka, Osaka (JP)

(73) Assignee: ISHIHARA SANGYO KAISHA, LTD., Osaka (JP)

( * ) Notice: Subject to any disclaimer, the term of this patent is extended or adjusted under 35 U.S.C. 154(b) by 141 days.

(21) Appl. No.: 16/088,722

(22) PCT Filed: Mar. 29, 2017

(86) PCT No.: PCT/JP2017/013043
§ 371 (c)(1),
(2) Date: Sep. 26, 2018

(87) PCT Pub. No.: WO2017/170759
PCT Pub. Date: Oct. 5, 2017

(65) Prior Publication Data
US 2020/0172517 A1    Jun. 4, 2020

(30) Foreign Application Priority Data

Mar. 30, 2016   (JP) .................. 2016-067797

(51) Int. Cl.
| | | |
|---|---|---|
| C07D 403/12 | (2006.01) |
| A01N 43/58 | (2006.01) |
| A01N 43/60 | (2006.01) |
| A01N 43/76 | (2006.01) |
| A01N 43/78 | (2006.01) |
| A01N 43/90 | (2006.01) |
| C07D 237/16 | (2006.01) |
| C07D 401/12 | (2006.01) |
| C07D 401/14 | (2006.01) |
| C07D 413/12 | (2006.01) |
| C07D 413/14 | (2006.01) |
| C07D 417/12 | (2006.01) |
| C07D 471/04 | (2006.01) |
| C07D 513/04 | (2006.01) |

(52) U.S. Cl.
CPC ........... *C07D 403/12* (2013.01); *A01N 43/58* (2013.01); *A01N 43/60* (2013.01); *A01N 43/76* (2013.01); *A01N 43/78* (2013.01); *A01N 43/90* (2013.01); *C07D 237/16* (2013.01); *C07D 401/12* (2013.01); *C07D 401/14* (2013.01); *C07D 413/12* (2013.01); *C07D 413/14* (2013.01); *C07D 417/12* (2013.01); *C07D 471/04* (2013.01); *C07D 513/04* (2013.01)

(58) Field of Classification Search
None
See application file for complete search history.

(56) References Cited

U.S. PATENT DOCUMENTS

| | | |
|---|---|---|
| 5,191,089 A | 3/1993 | Baasner et al. |
| 2009/0111696 A1 | 4/2009 | Kiji et al. |
| 2010/0216642 A1 | 8/2010 | Fusaka |
| 2012/0021907 A1 | 1/2012 | Mathews et al. |
| 2012/0021912 A1 | 1/2012 | Mathews et al. |
| 2013/0023415 A1 | 1/2013 | Witschel et al. |
| 2014/0378305 A1 | 12/2014 | Mathews et al. |
| 2017/0096402 A1* | 4/2017 | Ahrens ................ C07D 237/14 |

FOREIGN PATENT DOCUMENTS

| | | |
|---|---|---|
| GB | 2525270 A | 10/2015 |
| JP | 3-099059 A | 4/1991 |
| JP | 2012-515183 A | 7/2012 |

(Continued)

OTHER PUBLICATIONS

English Translation of WO 2014/119770 (2014).*
European Search Report, European Patent Office, Application No. 17775293.8, dated Aug. 19, 2019, 8 pages.
Thomas M. Stevenson et al., "Application of Cross-Coupling and Metalation Chemistry of 3(2H)-Pyridazinones to Fungicide and Herbicide Discovery", Journal of Heterocyclic Chemistry, 42 (3), ISSN: 0022-152X, compound 45, Apr. 2015, pp. 427-435.

(Continued)

*Primary Examiner* — Bong-Sook Baek
(74) *Attorney, Agent, or Firm* — Greenblum & Bernstein, P.L.C.

(57) ABSTRACT

A novel herbicide having remarkable herbicidal activities against undesired plants is provided.

A pyridazinone compound represented by the formula (I) or its salt:

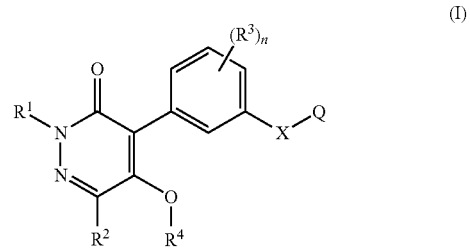

wherein X is —O—, —S—, —SO—, —SO$_2$— or —N(Y)—; Q is monocyclic aryl which may be substituted by Z, monocyclic heteroaryl which may be substituted by Z or the like; Y is a hydrogen atom or alkyl; Z is halogen, alkyl or the like; $R^1$ is alkyl, alkenyl or the like; $R^2$ is a hydrogen atom, alkyl or the like; $R^3$ is halogen, hydroxy or the like; $R^4$ is a hydrogen atom, alkyl or the like; and n is an integer of from 0 to 4.

5 Claims, No Drawings

(56) References Cited

FOREIGN PATENT DOCUMENTS

| JP | 2012-515742 A | 7/2012 |
|---|---|---|
| JP | 2013-522339 A | 6/2013 |
| JP | 2014-210806 A | 11/2014 |
| RU | 2463296 | 10/2011 |
| RU | 2440990 | 1/2012 |
| WO | 2008/013838 A2 | 1/2008 |
| WO | 2009/086041 A1 | 7/2009 |
| WO | 2012/091156 A1 | 7/2012 |
| WO | 2014/119770 A1 | 8/2014 |
| WO | 2014/207601 A1 | 12/2014 |
| WO | 2015/177109 A1 | 11/2015 |

OTHER PUBLICATIONS

International Search Report issued with respect to Patent Application No. PCT/JP2017/013043, dated Jun. 13, 2017.
International Preliminary Report on Patentability issued with respect to Patent Application No. PCT/JP2017/013043, dated Oct. 2, 2018.
Office Action issued in Russia Counterpart Patent Appl. No. 2018134186/04, dated Mar. 26, 2020, along with an English translation thereof.
Search Report for Application PCT/JP2017/013043, dated Mar. 26, 2020, with English translation.

* cited by examiner

PYRIDAZINONE COMPOUND OR ITS SALT, AND HERBICIDE CONTAINING IT

TECHNICAL FIELD

The present invention relates to a pyridazinone compound or its salt. More specifically, it relates to a novel pyridazinone compound or its salt useful as an active ingredient of a herbicide, and a herbicide containing it.

BACKGROUND ART

Patent Document 1 discloses a pyridazinone compound having a specific chemical structure. The compound has a —O-A group at the 4-position of a benzene ring substituted on the pyridazinone ring, and has a chemical structure different from that of the compound of the present invention.

Patent Document 2 discloses a heteroaromatic compound having a specific chemical structure. The compound has no pyridazinone ring as substituents at the m-positions (substituents $R^3$ and $R^4$ in Patent Document 2) of a phenyl ring bound to the pyridine ring via L1, and is distinguished from the compound of the present invention.

Patent Document 3 discloses a pyridazinone compound having a specific chemical structure. The compound has a phenyl group or heteroaromatic group directly bonded to a substituent G (benzene ring) on the pyridazinone ring and has a chemical structure different from that of the compound of the present invention.

Patent Document 4 discloses a pyridazinone compound having a specific chemical structure. The compound has a substituent (substituent $R^1$ in Patent Document 4) corresponding to the substituent Q in the after-mentioned formula (I) of the present application, which is a $NR^{10}R^{11}$ group or a heterocycloalkyl ring group, and has a chemical structure different from that of the compound of the present invention.

PRIOR ART DOCUMENTS

Patent Documents

Patent Document 1: WO2014/119770
Patent Document 2: WO2014/207601
Patent Document 3: WO2009/086041
Patent Document 4: WO2008/013838

DISCLOSURE OF INVENTION

Technical Problem

It is an object of the present invention to provide a herbicide having excellent herbicidal activities against weeds, for labor saving in the operation of controlling weeds and for improvement of productivity of agricultural and horticultural plants.

Solution to Problem

The present inventors have conducted extensive studies to achieve the above object and as a result, found that a pyridazinone compound having a specific chemical structure has high herbicidal effects against a wide variety of weeds with a low dose, and accomplished the present invention.

That is, the present invention relates to a pyridazinone compound represented by the formula (I) or its salt:

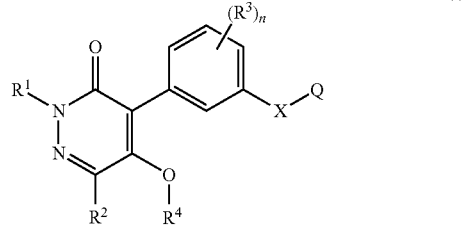

(I)

wherein X is —O—, —S—, —SO—, —SO$_2$— or —N(Y)—;

Q is monocyclic aryl which may be substituted by Z, monocyclic heteroaryl which may be substituted by Z, bicyclic aryl which may be substituted by Z, or bicyclic heteroaryl which may be substituted by Z;

Y is a hydrogen atom or alkyl;

$R^1$ is alkyl, alkenyl, alkynyl, cycloalkyl, cycloalkylalkyl, haloalkyl, monocyclic aryl which may be substituted by Z, monocyclic arylalkyl which may be substituted by Z, alkylthioalkyl, alkylsulfinylalkyl, alkylsulfonylalkyl, dialkylaminoalkyl, alkoxyalkyl, amino, nitro, alkylcarbonylalkyl, alkoxycarbonylalkyl or hydroxycarbonylalkyl;

$R^2$ is a hydrogen atom, alkyl, haloalkyl, cycloalkyl, halogen, alkoxy, alkylthio, alkylsulfinyl, alkylsulfonyl or cyano;

$R^3$ is halogen, hydroxy, alkyl, haloalkyl, alkenyl, haloalkenyl, alkynyl, haloalkynyl, alkoxy, haloalkoxy, nitro, amino, alkylcarbonyl or cycloalkyl;

$R^4$ is a hydrogen atom, alkyl, —C(O)R$^6$, —C(S)R$^6$, —SR$^7$, —SOR$^7$, —SO$_2$R$^7$, monocyclic arylalkyl which may be substituted by Z, alkoxyalkyl, —CH(J$^1$)OCOOJ$^2$, alkylcarbonylalkyl, monocyclic aryl which may be substituted by Z, monocyclic arylcarbonylalkyl which may be substituted by Z, alkenyl, alkoxyalkoxyalkyl, alkoxycarbonylalkyl, alkynyl, cyanoalkyl, haloalkoxyalkyl or dialkylaminoalkyl;

$R^6$ is alkyl, alkoxy, morpholino, dialkylamino, (monocyclic aryl which may be substituted by Z)(alkyl)amino, cycloalkyl, alkoxyalkyl, alkylthioalkyl, haloalkyl, alkylthio, alkenyl, alkynyl, alkoxycarbonylalkyl, cycloalkylalkyl, cyanoalkyl, alkoxyalkoxyalkyl, monocyclic aryl which may be substituted by Z, monocyclic heteroaryl which may be substituted by Z, monocyclic arylalkyl which may be substituted by Z, monocyclic aryloxy which may be substituted by Z, monocyclic arylthio which may be substituted by Z, monocyclic aryloxyalkyl which may be substituted by Z, monocyclic arylthioalkyl which may be substituted by Z, alkoxycarbonyl, alkoxyalkoxy, haloalkoxy, haloalkoxyalkoxy, alkylthioalkoxy, cycloalkoxyalkoxy, monocyclic arylalkoxy which may be substituted by Z, monocyclic aryloxyalkoxy which may be substituted by Z, monocyclic heteroaryloxyalkoxy which may be substituted by Z, alkenyloxyalkoxy, alkoxyalkoxyalkoxy, alkynyloxy, alkenyloxy, haloalkenyl, dialkylaminoalkyl, alkylthioalkoxy, cycloalkylalkoxy, cycloalkylalkoxyalkoxy, monocyclic arylalkoxyalkoxy which may be substituted by Z, monocyclic heteroarylalkoxyalkoxy which may be substituted by Z or cycloalkoxy which may be substituted by Z;

$R^7$ is alkyl, haloalkyl, cycloalkyl or monocyclic aryl which may be substituted by Z;

Z is halogen, alkyl, haloalkyl, alkoxy, haloalkoxy, cycloalkyl, cyano, nitro, —C(O)OR$^5$, formyl, alkylthio, alkylsulfinyl, alkylsulfonyl, —CH=NOJ$^3$ or dialkylaminocarbonyl;

$R^5$ is a hydrogen atom or alkyl;
$J^1$ is a hydrogen atom or alkyl;
$J^2$ is alkyl or cycloalkyl;
$J^3$ is a hydrogen atom, alkylcarbonyl or alkoxyalkyl; and
n is an integer of from 0 to 4.

Preferably, the present invention relates to a pyridazinone compound represented by the formula (I) or its salt:

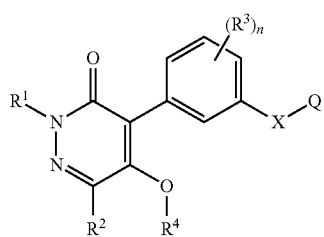

wherein X is —O—, —S—, —SO—, —SO$_2$— or —N(Y)—;

Q is monocyclic aryl which may be substituted by Z, monocyclic heteroaryl which may be substituted by Z, bicyclic aryl which may be substituted by Z or bicyclic heteroaryl which may be substituted by Z;

Y is a hydrogen atom or alkyl;
Z is halogen, alkyl, haloalkyl, cyano, nitro or —C(O)OR$^5$;
$R^1$ is alkyl, alkenyl, alkynyl or cycloalkyl;
$R^2$ is a hydrogen atom, alkyl, haloalkyl or cycloalkyl;
$R^3$ is halogen, alkyl, haloalkyl, alkenyl, haloalkenyl, alkynyl, haloalkynyl, alkoxy, haloalkoxy or cycloalkyl;
$R^4$ is a hydrogen atom, alkyl, —C(O)R$^6$ or —SO$_2$R$^7$;
$R^5$ is a hydrogen atom or alkyl;
$R^6$ is alkyl, alkoxy or morpholino;
$R^7$ is alkyl; and
n is an integer of from 1 to 4.

The present invention further relates to the pyridazinone compound of the formula (I) or its salt, a herbicide containing it as an active ingredient, and a method for controlling undesired plants or inhibiting their growth, which comprises applying a herbicidally effective amount of the pyridazinone compound or its salt to the undesired plants or to a place where they grow.

Advantageous Effects of Invention

The pyridazinone compound of the formula (I) or its salt of the present invention realizes a remarkable improvement in the herbicidal activities against undesired plants (weeds) as compared with similar conventional compounds.

DESCRIPTION OF EMBODIMENTS

The halogen atom or halogen atom as a substituent in the formula (I) may be an atom of fluorine, chlorine, bromine or iodine. The number of halogen atoms as substituents may be 1 or at least 2, and in the case of at least 2, the respective halogen atoms may be the same or different from one another. Further, substitution positions of such halogen atoms may be any positions.

The alkyl or alkyl moiety in the formula (I) may, for example, be a linear or branched $C_1$-$C_{12}$ group, such as methyl, ethyl, n-propyl, isopropyl, n-butyl, isobutyl, sec-butyl, tert-butyl, n-pentyl, neopentyl, n-hexyl, n-heptyl, n-octyl, n-nonyl, n-decyl, n-undecyl or n-dodecyl.

The alkoxy or alkoxy moiety in the formula (I) may, for example, be a linear or branched $C_1$-$C_{12}$ group, such as methoxy, ethoxy, propoxy, isopropoxy, butoxy, pentyloxy, hexyloxy, heptyloxy, octyloxy, nonyloxy, decyloxy, undecyloxy or dodecyloxy.

The alkenyl or alkenyl moiety in the formula (I) may, for example, be a linear or branched $C_2$-$C_6$ group, such as vinyl, 1-propenyl, 2-propenyl, isopropenyl, 2-methyl-1-propenyl, 1-methyl-1-propenyl, 2-methyl-2-propenyl, 1-methyl-2-propenyl, 1-butenyl, 2-butenyl, 3-butenyl, 1-pentenyl, 2-pentenyl, 2-methyl-2-butenyl, 3-methyl-2-butenyl, 1-hexenyl or 2,3-dimethyl-2-butenyl.

The alkynyl or alkynyl moiety in the formula (I) may, for example, be a linear or branched $C_2$-$C_6$ group, such as ethynyl, 1-propynyl, 2-propynyl, 1-butynyl, 2-butynyl, 3-butynyl, 1-methyl-2-propynyl, 2-methyl-3-butynyl, 1-hexynyl, 2-hexynyl, 3-hexynyl, 4-hexynyl or 5-hexynyl.

The cycloalkyl or cycloalkyl moiety in the formula (I) may, for example, be a $C_3$-$C_7$ group, such as cyclopropyl, cyclobutyl, cyclopentyl, cyclohexyl or cycloheptyl.

The cycloalkyloxy or cycloalkyloxy moiety in the formula (I) may, for example, be a $C_3$-$C_7$ group, such as cyclopropyloxy, cyclobutyloxy, cyclopentyloxy, cyclohexyloxy or cycloheptyloxy.

The monocyclic aryl in the formula (I) may, for example, be phenyl. Further, the monocyclic heteroaryl may, for example, be a 3- to 6-membered heteroaryl containing one to four O, S or N, specifically, thienyl, furyl, pyrrolyl, oxazolyl, isoxazolyl, isoxazolinyl, thiazolyl, isothiazolyl, pyrazolyl, imidazolyl, 1,3,4-oxadiazolyl, 1,2,4-oxadiazolyl, 1,3,4-thiadiazolyl, 1,2,4-thiadiazolyl, 1,2,4-triazolyl, 1,2,3-triazolyl, 1,2,3-thiadiazolyl, 1,2,3,4-tetrazolyl, pyridyl, pyrimidyl, pyrazinyl, pyridazinyl, 1,3,5-triazinyl, 1,2,4-triazinyl, imidazolinyl, imidazolidinyl, pyrazolinyl or pyrazolidinyl.

The bicyclic aryl in the formula (I) may, for example, be naphthyl or indenyl. Further, the bicyclic heteroaryl may, for example, be a condensed heteroaryl of a 5- to 6-membered heterocyclic ring containing one or two O, S or N, and a benzene ring, specifically, benzothienyl, benzofuryl, indolyl, benzothiazolyl, benzoimidazolyl, benzoisoxazolyl, benzoisothiazolyl, indazolyl, benzoxazolyl, quinolyl, isoquinolyl, quinoxalinyl, phthalazinyl, cinnolinyl, quinazolinyl, naphthyridinyl, pyridopyrimidyl, pyridopyrazinyl, imidazolopyridyl, thiazolopyridyl, pyrazolopyrimidyl, imidazolopyrazinyl, imidazolopyridazinyl, triazolopyridyl, pyrazinopyrazinyl, pyrazinopyridazinyl, pyrimidopyridazinyl, pyrimidopyrimidyl, pyridopyridazinyl, pyrrolopyridyl, thienopyridyl, oxazolopyridyl, pyrazolopyridyl, isoxazolopyridyl, isothiazolopyridyl, pyrrolopyrimidyl, thienopyrimidyl, imidazolopyrimidyl, oxazolopyrimidyl, thiazolopyrimidyl, isoxazolopyrimidyl, isothiazolopyrimidyl, pyrrolopyrazinyl, thienopyrazinyl, oxazolopyrazinyl, thiazolopyrazinyl, pyrazolopyrazinyl, isoxazolopyrazinyl, isothiazolopyrazinyl, pyrrolopyridazinyl, thienopyridazinyl, oxazolopyridazinyl, thiazolopyridazinyl, pyrazolopyridazinyl, isoxazolopyridazinyl, isothiazolopyridazinyl, purinyl or pteridinyl.

In the formula (I), "which may be substituted by Z" means that when each group is substituted by Z, the number of substituent Z may be one or more, and in a case where the number of substituent may be two or more, such substituents may be the same or different. The substitution position(s) of such substituent(s) may be any position(s).

The salt of the pyridazinone compound of the formula (I) includes all kinds of salts so long as they are agriculturally acceptable, and, for example, alkali metal salts such as a sodium salt and a potassium salt; alkaline earth metal salts such as a magnesium salt and a calcium salt; amine salts such as a dimethylamine salt and a triethylamine salt; inorganic acid salts such as a hydrochloride, a perchlorate, a sulfate and a nitrate; and organic acid salts such as an acetate and a methanesulfonate, may be mentioned.

As the pyridazinone compounds of the formula (I), isomers such as diastereo isomers and optical isomers may sometimes be present, and the present invention includes the respective isomers and isomer mixtures. In this specification, isomers are described as a mixture unless otherwise specified. Further, in the present invention, various isomers other than the above-mentioned isomers are included within a range of common knowledge in this technical field. Further, depending upon the type of an isomer, it may have a chemical structure different from the above formula (I), but for those skilled in the art, it is sufficiently recognizable that such a chemical structure is in a relation of an isomer to the formula (I), and such an isomer is evidently within the scope of the present invention.

The pyridazinone compound of the formula (I) or its salt (hereinafter referred to as the compound of the present invention) may be produced by the following production process or in accordance with a usual method for producing a salt or the after-mentioned Preparation Examples. However, the method to obtain the compound of the present invention is not limited thereto.

[Production Process 1]

A compound of the formula (I-1) which is a compound of the present invention may be produced by reacting a compound represented by the formula (I-2) and a compound represented by the formula (II) in the presence of a base.

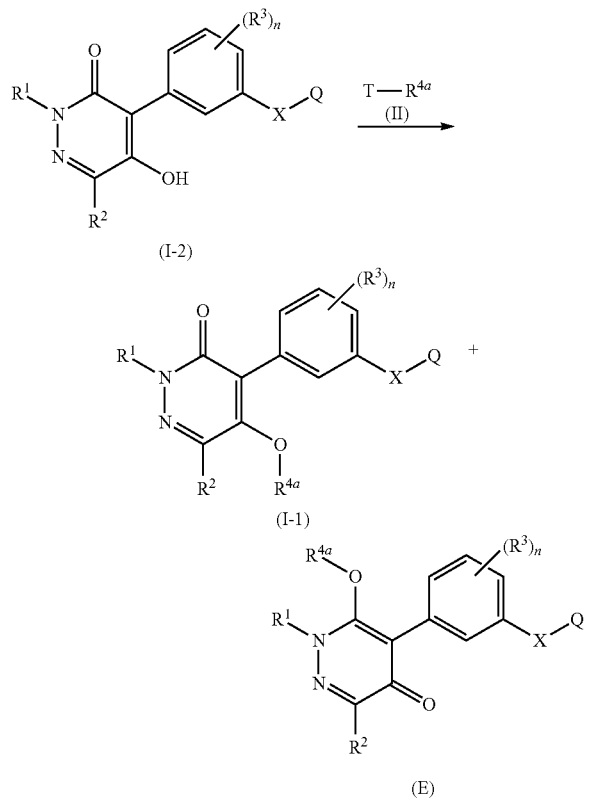

In the formulae, T is an atom of chlorine, bromine or iodine, $R^{4a}$ is alkyl, —C(O)$R^6$, —C(S)$R^6$, —S$R^7$, —SO$R^7$, —SO$_2R^7$, monocyclic arylalkyl which may be substituted by Z, alkoxyalkyl, —CH(J$^1$)OCOOJ$^2$, alkylcarbonylalkyl, monocyclic aryl which may be substituted by Z, monocyclic arylcarbonylalkyl which may be substituted by Z, alkenyl, alkoxyalkoxyalkyl, alkoxycarbonylalkyl, alkynyl, cyanoalkyl, haloalkoxyalkyl or dialkylaminoalkyl, and X, Q, $R^1$, $R^2$, $R^3$, $R^6$, $R^7$, Z, J$^1$, J$^2$ and n are as defined above.

The base used in this reaction may, for example, be an organic base such as triethylamine or pyridine. The amount of the base is usually from 0.5 to 10 molar equivalents, preferably from 1 to 5 molar equivalents to the compound of the formula (I-2).

This reaction is carried out usually in the presence of a solvent. The solvent is not particularly limited so long as it is inert to the reaction and may, for example, be an ether such as diethyl ether, dioxane, tetrahydrofuran (THF) or dimethoxyethane or a solvent mixture thereof.

The amount of the compound of the formula (II) used in this reaction is usually from 0.5 to 10 molar equivalents, preferably from 1 to 3 molar equivalents to the compound of the formula (I-2).

The reaction temperature of this reaction is usually from –30 to 180° C., preferably from –10 to 80° C. The reaction time of this reaction is usually from 10 minutes to 30 hours.

By this reaction, a mixture of the compound of the formula (I-1) and its isomer i.e. a compound represented by the formula (E) forms. The reaction mixture obtained by this reaction is, for example, mixed with water and extracted with an organic solvent, the obtained organic layer is dried, concentrated, purified by silica gel column chromatography, and the like, whereby the compound of the formula (I-1) can be isolated.

The compound of the formula (II) is a known compound or may be produced by a well-known method from a known compound.

[Production Process 2]

The compound of the formula (I-2) which is a compound of the present invention may be produced by reacting a compound represented by the formula (I-3) and morpholine.

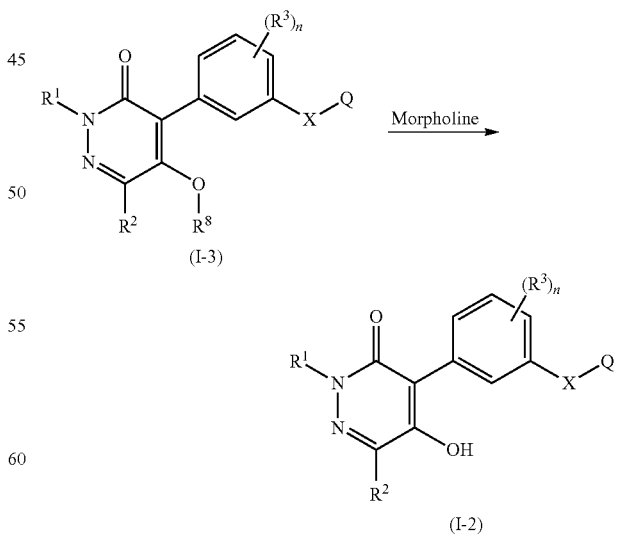

In the formulae, $R^8$ is alkyl or monocyclic arylalkyl which may be substituted by Z, such as $C_{1-3}$ alkyl or benzyl, and X, Q, $R^1$, $R^2$, $R^3$, Z and n are as defined above.

The amount of morpholine used in this reaction is usually from 1 to 20 molar equivalents to the compound of the formula (I-3).

The reaction temperature of this reaction is usually from 30 to 180° C., preferably from 50 to 130° C. The reaction time of this reaction is usually from 10 minutes to 30 hours.

Further, this reaction may be conducted under irradiation with microwaves, whereby the reaction may be promoted in some cases.

After completion of this reaction, for example, the reaction mixture is mixed with water, acidified with an acid and extracted with an organic solvent, and the obtained organic layer is dried, concentrated, purified by silica gel column chromatography, and the like, whereby the compound of the formula (I-2) can be isolated.

Further, the compound of the formula (I-2) may be produced, for example, in accordance with the method disclosed in e.g. Heterocycles, vol. 26, pages 1 to 4 (1987) or a method in accordance therewith.

[Production Process 3]

The compound of the formula (I-3) which is a compound of the present invention may be produced by reacting a compound represented by the formula (III) and a compound represented by the formula (IV) in the presence of a base or a catalyst.

is inert to the reaction and may, for example, be an aromatic hydrocarbon such as benzene, toluene or xylene; an ether such as diethyl ether, dioxane, THF or dimethoxyethane; an amide such as dimethylformamide (DMF); a sulfoxide such as dimethylsulfoxide (DMSO); a nitrile such as acetonitrile; a ketone such as acetone; or a solvent mixture thereof.

The amount of the compound of the formula (IV) used in this reaction is usually from 0.5 to 3 molar equivalents, preferably from 1 to 2 molar equivalents to the compound of the formula (III).

The reaction temperature of this reaction is usually from 0 to 200° C., preferably from 20 to 100° C. The reaction time of this reaction is usually from 10 minutes to 30 hours.

After completion of this reaction, for example, the reaction mixture is neutralized with an acid, mixed with water and extracted with an organic solvent, and the obtained organic layer is dried, concentrated, purified by silica gel column chromatography, and the like, whereby the compound of the formula (I-3) can be isolated.

The compound of the formula (IV) is a known compound, or may be produced by a well-known method from a known compound.

[Production Process 4]

The compound of the above formula (III) may be produced by reacting a compound represented by the formula (V) and an acid.

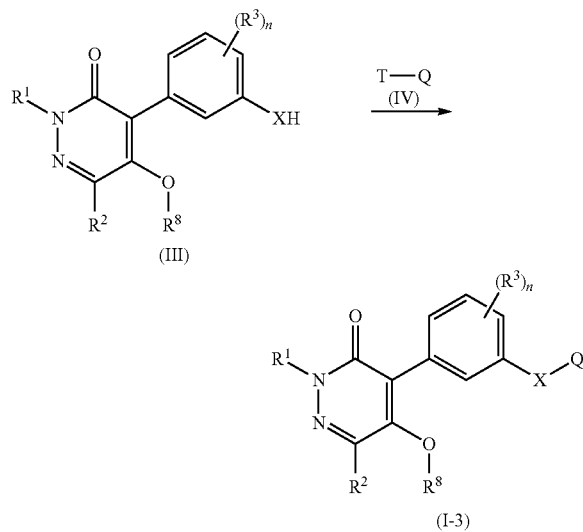

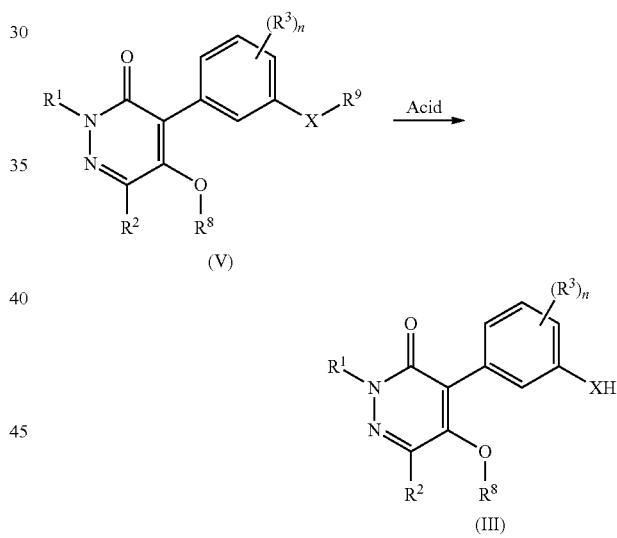

In the formulae, X, Q, $R^1$, $R^2$, $R^3$, $R^8$, T and n are as defined above.

The base used in this reaction may, for example, be a metal alkoxide such as potassium tert-butoxide; or an inorganic base such as potassium carbonate, cesium carbonate or sodium hydride. The amount of the base is usually from 1 to 10 molar equivalents, preferably from 1 to 3 molar equivalents to the compound of the formula (III).

The catalyst used in this reaction may, for example, be a palladium catalyst such as palladium(II) acetate, tetrakis(triphenylphosphine)palladium, tris(dibenzylideneacetone)dipalladium or [1,1'-bis(diphenylphosphino)ferrocene]palladium dichloride; or a copper catalyst such as copper chloride or copper iodide. The amount of the catalyst is usually from 0.001 to 0.5 molar equivalent, preferably from 0.01 to 0.2 molar equivalent to the compound of the formula (IV).

This reaction is carried out usually in the presence of a solvent. The solvent is not particularly limited so long as it In the formulae, $R^9$ is monocyclic arylalkyl which may be substituted by Z, such as benzyl or 4-methoxybenzyl, and X, $R^1$, $R^2$, $R^3$, $R^8$, Z and n are as defined above.

The acid used in this reaction may, for example, be trifluoroacetic acid. The amount of the acid is usually from 1 to 20 molar equivalents to the compound of the formula (V).

This reaction is carried out in the presence of a solvent as the case requires. The solvent is not particularly limited so long as it is inert to the reaction and may, for example, be an organic acid such as acetic acid or propionic acid; water; or a solvent mixture thereof.

The reaction temperature of this reaction is usually from 30 to 180° C., preferably from 50 to 130° C. The reaction time of this reaction is usually from 10 minutes to 30 hours.

After completion of this reaction, for example, the reaction mixture is mixed with water and extracted with an organic solvent, and the obtained organic layer is dried, concentrated, purified by silica gel column chromatography, and the like, whereby the compound of the formula (III) can be isolated.

[Production Process 5]

The compound of the formula (V) may be produced by reacting a compound represented by the formula (VI) and a compound represented by the formula (VII) or (VIII) in the presence of a base and a catalyst.

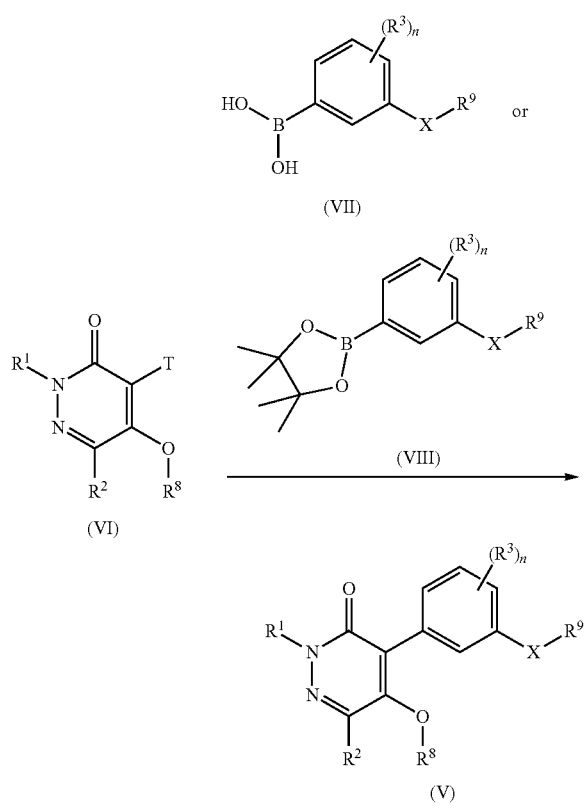

In the formulae, X, $R^1$, $R^2$, $R^3$, $R^8$, $R^9$, T and n are as defined above.

The base used in this reaction may, for example, be an inorganic base such as sodium carbonate, potassium carbonate, sodium hydrogen carbonate, cesium carbonate or potassium phosphate. The amount of the base is usually from 1 to 10 molar equivalents, preferably from 1 to 5 molar equivalents to the compound of the formula (VI).

The catalyst used in this reaction may, for example, be a palladium catalyst such as palladium(II) acetate, tetrakis(triphenylphosphine)palladium, tris(dibenzylideneacetone)dipalladium or [1,1'-bis(diphenylphosphino)ferrocene]palladium dichloride. The amount of the catalyst is usually from 0.001 to 0.5 molar equivalent, preferably from 0.01 to 0.2 molar equivalent to the compound of the formula (VI). Further, as the catalyst, a phase transfer catalyst may be used. The phase transfer catalyst used in this reaction may, for example, be a quaternary alkyl ammonium salt such as tetrabutylammonium bromide or tetrabutylammonium chloride. The amount of the phase transfer catalyst is usually from 0.001 to 1.0 molar equivalent, preferably from 0.01 to 0.7 molar equivalent to the compound of the formula (VI).

This reaction is carried out usually in the presence of a solvent. The solvent is not particularly limited so long as it is inert to the reaction and may, for example, be an aromatic hydrocarbon such as benzene or toluene; an alcohol such as methanol, ethanol or propanol; an ether such as diethyl ether, dioxane, THF or dimethoxyethane; a ketone such as acetone or methyl ethyl ketone; an amide such as DMF; a sulfoxide such as DMSO; water; or a solvent mixture thereof.

In this reaction, as the case requires, a ligand may be used. The ligand may, for example, be 2-dicyclohexylphosphino-2',6'-dimethoxybiphenyl. The amount of the ligand is usually from 0.002 to 1 molar equivalent, preferably from 0.02 to 0.4 molar equivalent to the compound of the formula (VI).

The amount of the compound of the formula (VII) or (VIII) used in this reaction is usually from 0.5 to 2 molar equivalents, preferably from 1 to 1.5 molar equivalents to the compound of the formula (VI).

The reaction temperature of this reaction is usually from 0 to 180° C., preferably from 30 to 150° C. The reaction time of this reaction is usually from 10 minutes to 100 hours.

After completion of this reaction, for example, the reaction mixture is mixed with water and extracted with an organic solvent, and the obtained organic layer is dried, concentrated, purified by silica gel column chromatography, and the like, whereby the compound of the formula (V) can be isolated.

The compound of the formula (VII) is a known compound or may be produced by a well-known method from a known compound.

The compound of the formula (VI) is a known compound or may be produced by a well-known method from a known compound. For example, the compound of the formula (VI) may be produced in accordance with the method disclosed in Journal of Heterocyclic Chemistry, vol. 33, pages 1579 to 1582 (1996) or a method in accordance therewith.

[Production Process 6]

The compound of the formula (VIII) may be produced by reacting a compound represented by the formula (IX) and a compound represented by the formula (X) in the presence of a base and a catalyst.

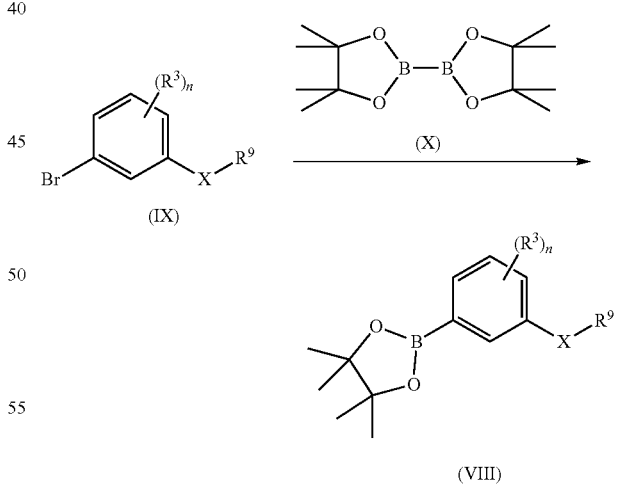

In the formulae, X, $R^3$, $R^9$ and n are as defined above.

The base used in this reaction may, for example, be an inorganic base such as sodium carbonate, potassium carbonate, sodium hydrogen carbonate, cesium carbonate, potassium phosphate or potassium acetate. The amount of the base is usually from 1 to 10 molar equivalents, preferably from 1 to 5 molar equivalents to the compound of the formula (IX).

The catalyst used in this reaction may, for example, be a palladium catalyst such as palladium(II) acetate, tetrakis(triphenylphosphine)palladium or tris(dibenzylideneacetone)dipalladium. The amount of the catalyst is usually from 0.001 to 0.5 molar equivalent, preferably from 0.01 to 0.2 molar equivalent to the compound of the formula (IX).

This reaction is carried out usually in the presence of a solvent. The solvent is not particularly limited so long as it is inert to the reaction and may, for example, be an aromatic hydrocarbon such as benzene or toluene; an alcohol such as methanol, ethanol or propanol; an ether such as diethyl ether, dioxane, THF or dimethoxyethane; a ketone such as acetone or methyl ethyl ketone; an amide such as DMF; a sulfoxide such as DMSO; water; or a solvent mixture thereof.

In this reaction, as the case requires, a ligand may be used. The ligand may, for example, be tricyclohexylphosphine or 2-dicyclohexylphosphino-2',6'-dimethoxybiphenyl. The amount of the ligand is usually from 0.002 to 1 molar equivalent, preferably from 0.02 to 0.4 molar equivalent to the compound of the formula (IX).

The amount of the compound of the formula (X) used in this reaction is usually from 0.5 to 2 molar equivalents, preferably from 1 to 1.5 molar equivalents to the compound of the formula (IX).

The reaction temperature of this reaction is usually from 0 to 180° C., preferably from 30 to 150° C. The reaction time of this reaction is usually from 10 minutes to 100 hours.

Further, this reaction may be conducted under irradiation with microwaves, whereby the reaction may be promoted in some cases.

After completion of this reaction, for example, the reaction mixture is mixed with water and extracted with an organic solvent, and the obtained organic layer is dried, concentrated, purified by silica gel column chromatography, and the like, whereby the compound of the formula (VIII) can be isolated.

[Production Process 7]

The compound of the formula (IX) may be produced by reacting a compound represented by the formula (XI) and a compound represented by the formula (XII) in the presence of a base and a catalyst.

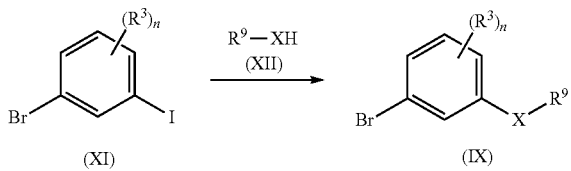

In the formulae, X, $R^3$, $R^9$ and n are as defined above.

The base used in this reaction may, for example, be an inorganic base such as sodium carbonate, potassium carbonate, sodium hydrogen carbonate, cesium carbonate or potassium phosphate; or an organic base such as triethylamine or diisopropylethylamine. The amount of the base is usually from 1 to 10 molar equivalents, preferably from 1 to 5 molar equivalents to the compound of the formula (XI).

The catalyst used in this reaction may, for example, be a palladium catalyst such as palladium(II) acetate, tetrakis(triphenylphosphine)palladium or tris(dibenzylideneacetone)dipalladium. The amount of the catalyst is usually from 0.001 to 0.5 molar equivalent, preferably from 0.01 to 0.2 molar equivalent to the compound of the formula (XI).

This reaction is carried out usually in the presence of a solvent. The solvent is not particularly limited so long as it is inert to the reaction and may, for example, be an aromatic hydrocarbon such as benzene or toluene; an alcohol such as methanol, ethanol or propanol; an ether such as diethyl ether, dioxane, THF or dimethoxyethane; a ketone such as acetone or methyl ethyl ketone; an amide such as DMF; a sulfoxide such as DMSO; water; or a solvent mixture thereof.

In this reaction, as the case requires, a ligand may be used. The ligand may, for example, be tricyclohexylphosphine, 2-dicyclohexylphosphino-2',6'-dimethoxybiphenyl or 4,5-bis(diphenylphosphino)-9,9-dimethylxanthene. The amount of the ligand is usually from 0.002 to 1 molar equivalent, preferably from 0.02 to 0.4 molar equivalent to the compound of the formula (XI).

The amount of the compound of the formula (XII) used in this reaction is usually from 0.5 to 2 molar equivalents, preferably from 1 to 1.5 molar equivalents to the compound of the formula (XI).

The reaction temperature of this reaction is usually from 0 to 180° C., preferably from 30 to 150° C. The reaction time of this reaction is usually from 10 minutes to 100 hours.

After completion of this reaction, for example, the reaction mixture is mixed with water and extracted with an organic solvent, and the obtained organic layer is dried, concentrated, purified by silica gel column chromatography, and the like, whereby the compound of the formula (IX) can be isolated.

The compound of the formula (XI) is a known compound or may be produced by a well-known method from a known compound.

The compound of the formula (XII) is a known compound.

[Production Process 8]

The compound of the formula (IX) may be produced by reacting a compound represented by the formula (XIII) and a compound represented by the formula (XIV) in the presence of a base.

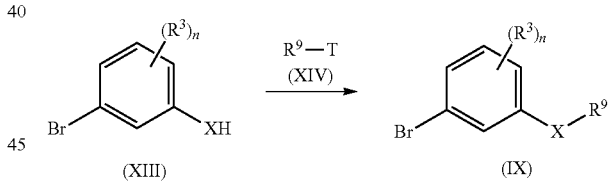

In the formulae, X, $R^3$, $R^9$, T and n are as defined above.

The base used in this reaction may, for example, be a metal alkoxide such as potassium tert-butoxide; or an inorganic base such as potassium carbonate, cesium carbonate or sodium hydride. The amount of the base is usually from 1 to 10 molar equivalents, preferably from 1 to 3 molar equivalents to the compound of the formula (XIII).

This reaction is carried out usually in the presence of a solvent. The solvent is not particularly limited so long as it is inert to the reaction and may, for example, be an aromatic hydrocarbon such as benzene, toluene or xylene; an ether such as diethyl ether, dioxane, THF or dimethoxyethane; an amide such as DMF; a sulfoxide such as DMSO; a nitrile such as acetonitrile; a ketone such as acetone; or a solvent mixture thereof.

The amount of the compound of the formula (XIV) used in this reaction is usually from 0.5 to 3 molar equivalents, preferably from 1 to 2 molar equivalents to the compound of the formula (XIII).

The reaction temperature of this reaction is usually from 0 to 200° C., preferably from 20 to 100° C. The reaction time of this reaction is usually from 10 minutes to 30 hours.

After completion of this reaction, for example, the reaction mixture is neutralized with an acid, mixed with water and extracted with an organic solvent, and the obtained organic layer is dried, concentrated, purified by silica gel column chromatography, and the like, whereby the compound of the formula (IX) can be isolated.

The compound of the formula (XIII) is a known compound or may be produced by a well-known method from a known compound.

The production processes for intermediates to be used for the production of the compounds of the present invention are not limited to the above-exemplified production processes, and any production process may be employed. Further, various starting materials are also not limited to the above-exemplified compounds, and any compounds may be used so long as they are compounds capable of producing the compounds of the present invention.

The compounds of the present invention are capable of controlling a wide range of undesired weeds such as annual weeds and perennial weeds, specifically, various noxious weed, for example, gramineae such as barnyardgrass (*Echinochloa crus-qalli* L., *Echinochloa orvzicola* vasing.), crabgrass (*Digitaria sanquinalis* L., *Digitaria ischaemum* Muhl., *Digitaria adscendens* Henr., *Digitaria microbachne* Henr., *Digitaria horizontalis* Willd.), green foxtail (*Setaria viridis* L.), giant foxtail (*Setaria faberi* Herrm.), yellow foxtail (*Setaria, lutescens* Hubb.), goosegrass (*Eleusine indica* L.), wild oat (*Avena fatua* L.), johnsongrass (*Sorghum halepense* L.), quackgrass (*Agropyron repens* L.), alexandergrass (*Brachiaria plantaginea*), guineagrass (*Panicum maximum* Jacq.), paragrass (*Panicum purpurascens*), smooth witchgrass (*Panicum dichotomiflorum*), sprangletop (*Leptochloa chinensis*), red sprangletop (*Leptochloa panicea*), annual bluegrass (*Poa annus* L.), black grass (*Alopecurus myosuroides* Huds., *Alopecurus aequalis* Sobol.), cholorado bluestem (*Agropyron tsukushiense* (Honda) Ohwi), broadleaf signalgrass (*Brachiaria platyphylla* Nash), southern sandbur (*Cenchrus echinatus* L.), italian ryegrass (*Lolium multiflorum* Lam.), rigid ryegrass (*Lolium rigidum* Gaud.), cheat grass (*Bromus tectorum* L.) and bermudagrass (*Cynodon dactylon* Pers.); cyperaceae such as rice flatsedge (*Cyperus iria* L.), purple nutsedge (*Cyperus rotundus* L.), yellow nutsedge (*Cyperus esculentus* L.), Japanese bulrush (*Scirpus luncoides*), flatsedge (*Cyperus serotinus*), smallflower umbrellaplant (*Cyperus difformis*), slender spikerush (*Eleocharis acicularis*), and water chestnut (*Eleocharis kuroguwai*); alismataceae such as Japanese ribbon waparo (*Sagittaria pygmaea*), arrow-head (*Sagittaria trifolia*), and narrowleaf waterplantain (*Alisma canaliculatum*); pontederiaceae such as *monochoria* (*Monochoria vaginalis*), and *monochoria* species (*Monochoria korsakowii*); linderniaceae such as false pimpernel (*Lindernia pyxidaria*); plantaginaceae such as abunome (*Dopatrium iunceum*); lythraceae such as toothcup (*Rotala india*), and red stem (*Ammannia multiflora*); elatinaceae such as long stem waterwort (*Elatine triandra* SCHK.); malvaceae such as velvetleaf (*Abutilon theophrasti* MEDIC), and prickly *sida* (*Sida spinosa* L.); compositae such as common cocklebur (*Xanthium strumarium* L.), common ragweed (*Ambrosia elatior* L.), thistle (*Breea setosa* (BIEB.) KITAM.), hairy galinsoga (*Galinsoga ciliata* Blake), wild chamomile (*Matricaria chamomilla* L.), henbit (*Lamium amplexicaule* L.), common dandelion (*Taraxacum officinale* weber), and horseweed (*Erigeron canadensis* L.); solanaceae such as black nightshade (*Solanum nigrum* L.), and jimsonweed (*Datura stramonium*); amaranthaceae such as slender amaranth (*Amaranthus viridis* L.), redroot pigweed (*Amaranthus retroflexus* L.), common lambsquarters (*Chenopodium album* L.), and mexican burningbush (*Kochia scoparia* Schrad.); polygonaceae such as pale smartweed (*Polygonum lapathifolium* L.), ladysthumb (*Polygonum persicaria* L.), wild buckwheat (*Polygonum convolvulus* L.), and knotweed (*Polygonum aviculare* L.); cruciferae such as flexuous bittercress (*Cardamine flexuosa* WITH.), shepherd's-purse (*Capsella bursapastoris* Medik.), and indian mustard (*Brassica juncea* Czern.); convolvulaceae such as tall morningglory (*Ipomoea purpurea* L.), field bindweed (*Convolvulus arvensis* L.), and ivyleaf morningglory (*Ipomoea hederacea* Jacq.); portulacaceae such as common purslane (*Portulaca oleracea* L.); fabaceae such as sicklepod (*Cassia obtusifolia* L.); caryophyllaceae such as common chickweed (*Stellaria media* L.); rubiaceae such as catchweed (*Galium spurium* L.); euphorbiaceae such as threeseeded copperleaf (*Acalypha australis* L.); and commelinaceae such as common dayflower (*Commelina communis* L.). Therefore, the compound of the present invention can be effectively used for selectively controlling noxious weeds or nonselectively controlling noxious weeds in cultivation of useful crops such as corn (*Zea mays* L.), soybean (*Glycine max* Merr.), cotton (*Gossypium* spp.), wheat (*Triticum aestivum* L.), rice (*Oryza sativa* L.), barley (*Hordeum vulgare* L.), rye (*Secale cereale* L.), oat (*Avena sativa* L.), sorgo (*Sorghum bicolor* Moench), rape (*Brassica napus* L.), sunflower (*Helianthus annuus* L.), sugar beet (*Beta vulgaris* L.), sugar cane (*Saccharum officinarum* L.), japanese lawngrass (*Zoysia japonica* stend), peanut (*Arachis hypogaea* L.), flax (*Linum usitatissimum* L.), tobacco (*Nicotiana tabacum* L.), and coffee (*Coffea* spp.).

The compound of the present invention may be mixed with various agricultural additives and applied in the form of various formulations such as dusts, granules, water dispersible granules, wettable powders, tablets, pills, capsules (including a formulation packaged by a water soluble film), water-based suspensions, oil-based suspensions, microemulsions, suspoemulsions, water soluble powders, emulsifiable concentrates, soluble concentrates or pastes. It may be formed into any formulation which is commonly used in this field, so long as the object of the present invention is thereby met.

The additives to be used for the formulation include, for example, a solid carrier such as diatomaceous earth, slaked lime, calcium carbonate, talc, white carbon, kaoline, bentonite, kaolinite, sericite, clay, sodium carbonate, sodium bicarbonate, mirabilite, zeolite or starch; a solvent such as water, toluene, xylene, solvent naphtha, dioxane, acetone, isophorone, methyl isobutyl ketone, chlorobenzene, cyclohexane, dimethyl sulfoxide, N,N-dimethylformamide, dimethylacetamide, N-methyl-2-pyrrolidone or an alcohol; an anionic surfactant or a spreader such as a salt of fatty acid, a benzoate, an alkylsulfosuccinate, a dialkylsulfosuccinate, a polycarboxylate, a salt of alkylsulfuric acid ester, an alkyl sulfate, an alkylaryl sulfate, an alkyl diglycol ether sulfate, a salt of alcohol sulfuric acid ester, an alkyl sulfonate, an alkylaryl sulfonate, an aryl sulfonate, a lignin sulfonate, an alkyldiphenyl ether disulfonate, a polystyrene sulfonate, a salt of alkylphosphoric acid ester, an alkylaryl phosphate, a styrylaryl phosphate, a salt of polyoxyethylene alkyl ether sulfuric acid ester, a polyoxyethylene alkylaryl ether sulfate, a salt of polyoxyethylene alkylaryl ether sulfuric acid ester, a polyoxyethylene alkyl ether phosphate, a salt of polyoxyethylene alkylaryl phosphoric acid ester, a salt of polyoxyethylene aryl ether phosphoric acid ester, a naphthalene sulfonate condensed with formaldehyde or an alkylnaphthalene sulfonate condensed with formaldehyde; a nonionic surfactant or a spreader such as a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, polyethylene glycol, a polyoxyethylene fatty acid ester, a polyoxyethylene sorbitan fatty acid ester, a polyoxyethylene glycerin fatty acid ester, a polyoxyethylene hydrogenated castor oil or a polyoxypropylene fatty acid ester; and a vegetable oil or mineral oil such as olive oil, kapok oil, castor oil, palm oil, camellia oil, coconut oil, sesame oil, corn oil, rice bran oil, peanut oil, cottonseed oil, soybean oil, rapeseed oil, linseed oil, tung oil or liquid paraffins. These additives may suitably be selected for use alone or in combination as a mixture of two or more of them, so long as the object of the present invention is met. Further, various additives commonly used, such as a filler, a thickener, an anti-settling agent, an anti-freezing agent, a dispersion stabilizer, a safener, an anti-mold agent, a bubble agent, a disintegrator and a binder, may be used. The mix ratio by weight of the compound of the present invention to such various additives may be from 0.1:99.9 to 95:5, preferably from 0.2:99.8 to 85:15 in weight ratio. The method for mixing the compound of the present invention and various additives is not particularly limited, and they may be suitably mixed in accordance with a well-known method.

The dose of the herbicide containing the compound of the present invention (a herbicidally effective amount of the compound of the present invention) cannot generally be defined, as it varies depending upon the weather conditions, the soil conditions, the type of the formulation, the type of the undesired plants to be controlled, the application season, etc. However, it is usually applied in an amount of the compound of the present invention (hereinafter referred to also as active ingredient amount) of preferably from 0.1 to 5,000 g, more preferably from 0.5 to 3,000 g, further preferably from 1 to 1,000 g, particularly preferably from 10 to 500 g, per hectare. The present invention includes such a method for controlling undesired plants, by such applications of the herbicide.

Further, the herbicide containing the compound of the present invention may be used alone or as a mixture or in combination with other agricultural chemicals, fertilizers, safeners or the like. When the herbicide is used as a mixture or in combination, more excellent effects or function may be obtained in some cases. Such other agricultural chemicals include, for example, a herbicide, a fungicide, an antibiotic, a plant hormone and an insecticide. Especially, with a mixed herbicidal composition having a compound of the present invention mixed with or used in combination with one or more active compounds of other herbicides, the range of weeds to be controlled, the time of application of the composition, the herbicidal activities, etc. may be improved to preferred directions. The compound of the present invention and the active compounds of other herbicides may separately be formulated so that they may be mixed for use at the time of application, or they may be formulated together. The present invention includes such a mixed herbicidal composition.

The mixing ratio of the compound of the present invention to the active compounds of other herbicides cannot generally be defined, since it varies depending upon the weather conditions, the soil conditions, the types of formulations, the application time, the application method, etc., but the other herbicides are mixed in an amount of preferably from 0.001 to 10,000 parts by weight, further preferably from 0.01 to 1,000 parts by weight per one type of the active compound, based on 1 part by weight of the compound of the present invention. Further, the dose for the application is such that the total amount of the active compounds is from 0.1 to 10,000 g, preferably from 0.2 to 5,000 g, more preferably from 10 to 3,000 g, per hectare. The present invention includes a method for controlling undesired weeds by application of such a mixed herbicidal composition.

Another herbicidally active compound includes, for example, the following compounds (1) to (12) (common names including ones under application for approval by ISO). Even when not specifically mentioned here, in a case where such compounds have salts, alkyl esters, etc., they are, of course, all included.

(1) Those which are believed to exhibit herbicidal effects by disturbing hormone activities of plants, such as a phenoxy compound such as 2,4-D, 2,4-D-butotyl, 2,4-D-butyl, 2,4-D-dimethylammonium, 2,4-D-diolamine, 2,4-D-ethyl, 2,4-D-2-ethylhexyl, 2,4-D-isobutyl, 2,4-D-isoctyl, 2,4-D-isopropyl, 2,4-D-isopropylammonium, 2,4-D-sodium, 2,4-D-isopropanolammonium, 2,4-D-trolamine, 2,4-DB, 2,4-DB-butyl, 2,4-DB-dimethylammonium, 2,4-DB-isoctyl, 2,4-DB-potassium, 2,4-DB-sodium, 2,4-D choline salt, dichlorprop, dichlorprop-butotyl, dichlorprop-dimethylammonium, dichlorprop-isoctyl, dichlorprop-potassium, dichlorprop-P, dichlorprop-P-dimethylammonium, dichlorprop-P-potassium, dichlorprop-P-sodium, MCPA, MCPA-butotyl, MCPA-dimethylammonium, MCPA-2-ethylhexyl, MCPA-potassium, MCPA-sodium, MCPA-thioethyl, MCPB, MCPB-ethyl, MCPB-sodium, mecoprop, mecoprop-butotyl, mecoprop-sodium, mecoprop-P, mecoprop-P-butotyl, mecoprop-P-dimethylammonium, mecoprop-P-2-ethylhexyl, mecoprop-P-potassium, naproanilide, clomeprop, or HIA-1; an aromatic carboxylic acid compound such as 2,3,6-TBA, dicamba, dicamba-butotyl, dicamba-diglycolamine, dicamba-dimethylammonium, dicamba-diolamine, dicamba-isopropylammonium, dicamba-potassium, dicamba-sodium, picloram, picloram-dimethylammonium, picloram-isoctyl, picloram-potassium, picloram-triisopropanolammonium, picloram-triisopropylammonium, picloram-trolamine, triclopyr, triclopyr-butotyl, triclopyr-triethylammonium, clopyralid, clopyralid-olamine, clopyralid-potassium, clopyralid-triisopropanolammonium, aminopyralid, aminocyclopyrachior, halauxifen, halauxifen-methyl, or DAS-534; and naptalam, naptalam-sodium, benazolin, benazolin-ethyl, quinclorac, quinmerac, diflufenzopyr, diflufenzopyr-sodium, fluroxypyr, fluroxypyr-2-butoxy-1-methylethyl, fluroxypyr-meptyl, chlorflurenol, chlorflurenol-methyl, or clacyfos.

(2) Those which are believed to exhibit herbicidal effects by inhibiting photosynthesis of plants, such as a urea compound such as chlorotoluron, diuron, fluometuron, linuron, isoproturon, metobenzuron, tebuthiuron, dimefuron, isouron, karbutilate, methabenzthiazuron, metoxuron, metoburomuron, monolinuron, neburon, siduron, terbumeton or trietazine; a triazine compound such as simazine, atrazine, atratone, simetryn, prometryn, dimethametryn, hexazinone, metribuzin, terbuthylazine, cyanazine, ametryn, cybutryne, terbutryn, propazine, metamitron, or prometon; a uracil compound such as bromacil, bromacil-lithium, lenacil or terbacil; an anilide compound such as propanil or cypromid; a carbamate compound such as swep, desmedipham or phenmedipham; a hydroxybenzonitrile compound such as bromoxynil, bromoxynil-octanoate, bromoxynil-heptanoate, ioxynil, ioxynil-octanoate, ioxynil-potassium or ioxynil-sodium; and pyridate, bentazone, bentazone-sodium, amicarbazone, methazole, pentanochlor or phenmedipham.

(3) Quaternary ammonium salt compound such as paraquat or diquat, which is believed to be converted to free radicals by itself to form active oxygen in the plant body and shows rapid herbicidal efficacy.

(4) Those which are believed to exhibit herbicidal effects by inhibiting chlorophyll biosynthesis of plants and abnormally accumulating a photosensitizing peroxide substance in the plant body, such as a diphenylether compound such as nitrofen, chlomethoxyfen, bifenox, acifluorfen, acifluorfen-sodium, fomesafen, fomesafen-sodium, oxyfluorfen, lactofen, aclonifen, ethoxyfen-ethyl, fluoroglycofen-ethyl or fluoroglycofen; a cyclic imide compound such as chlorphthalim, flumioxazin, flumiclorac, flumiclorac-pentyl, cinidon-ethyl, fluthiacet-methyl, or EK-5385; and oxadiargyl, oxadiazon, sulfentrazone, carfentrazone-ethyl, thidiazimin, pentoxazone, azafenidin, isopropazole, pyraflufen-ethyl, benzfendizone, butafenacil, saflufenacil, fluazolate, profluazol, flufenpyr-ethyl, bencarbazone, tiafenacil, pyrachlonil, trifludimoxazin, HNPC-B4047, IR-6396, EK-5439, EK-5498, SYN-523, or a compound disclosed in WO2008/008763 (FMC CORPORATION).

(5) Those which are believed to exhibit herbicidal effects characterized by bleaching activities by inhibiting chromogenesis of plants such as carotenoids, such as a pyridazinone compound such as norflurazon, chloridazon or metflurazon; a pyrazole compound such as pyrazolynate, pyrazoxyfen, benzofenap, topramezone, pyrasulfotole or tolpyralate; and amitrole, fluridone, flurtamone, diflufenican, methoxyphenone, clomazone, sulcotrione, mesotrione, tembotrione, tefuryltrione, fenquinotrione, cyclopyrimorate, isoxaflutole, difenzoquat, difenzoquat-metilsulfate, isoxachlortole, benzobicyclon, bicyclopyron, picolinafen, beflubutamid, ketospiradox, ketospiradox-potassium, or a compound disclosed in JP2012-2571 (Sumitomo Chemical).

(6) Those which are believed to exhibit herbicidal effects by inhibiting a lipid biosynthesis of plants, such as an aryloxyphenoxypropionic acid compound such as diclofop-methyl, diclofop, pyriphenop-sodium, fluazifop-butyl, fluazifop, fluazifop-P, fluazifop-P-butyl, haloxyfop-methyl, haloxyfop, haloxyfop-etotyl, haloxyfop-P, haloxyfop-P-methyl, quizalofop-ethyl, quizalofop-P, quizalofop-P-ethyl, quizalofop-P-tefuryl, cyhalofop-butyl, fenoxaprop-ethyl, fenoxaprop-P, fenoxaprop-P-ethyl, metamifop-propyl, metamifop, clodinafop-propargyl, clodinafop, propaquizafop, HNPC-A8169 or SYP-1924; a cyclohexanedione compound such as alloxydim-sodium, alloxydim, clethodim, sethoxydim, tralkoxydim, butroxydim, tepraloxydim, profoxydim or cycloxydim, and a phenylpyrazoline compound such as pinoxaden.

(7) Those which are believed to exhibit herbicidal effects by inhibiting an amino acid biosynthesis of plants, such as a sulfonylurea compound such as chlorimuron-ethyl, chlorimuron, sulfometuron-methyl, sulfometuron, primisulfuron-methyl, primisulfuron, bensulfuron-methyl, bensulfuron, chlorsulfuron, metsulfuron-methyl, metsulfuron, cinosulfuron, pyrazosulfuron-ethyl, pyrazosulfuron, flazasulfuron, rimsulfuron, nicosulfuron, imazosulfuron, flucetosulfuron, cyclosulfamuron, prosulfuron, flupyrsulfuron-methyl-sodium, flupyrsulfuron, triflusulfuron-methyl, triflusulfuron, halosulfuron-methyl, halosulfuron, thifensulfuron-methyl, thifensulfuron, ethoxysulfuron, oxasulfuron, ethametsulfuron, ethametsulfuron-methyl, iodosulfuron, iodosulfuron-methyl-sodium, sulfosulfuron, triasulfuron, tribenuron-methyl, tribenuron, tritosulfuron, foramsulfuron, trifloxysulfuron, trifloxysulfuron-sodium, mesosulfuron-methyl, mesosulfuron, orthosulfamuron, amidosulfuron, azimsulfuron, propyrisulfuron, metazosulfuron, methiopyrsulfuron, monosulfuron-methyl, orsosulfuron, iofensulfuron or iofensulfuron-sodium; a triazolopyrimidinesulfonamide compound such as flumetsulam, metosulam, diclosulam, cloransulam-methyl, florasulam, penoxsulam or pyroxsulam; an imidazolinone compound such as imazapyr, imazapyr-isopropylammonium, imazethapyr, imazethapyr-ammonium, imazaquin, imazaquin-ammonium, imazamox, imazamox-ammonium, imazamethabenz, imazamethabenz-methyl or imazapic; a pyrimidinylsalicylic acid compound such as pyrithiobac-sodium, bispyribac-sodium, pyriminobac-methyl, pyribenzoxim, pyriftalid, pyrimisulfan, or triafamone; a sulfonylaminocarbonyltriazolinone compound such as flucarbazone, flucarbazone-sodium, propoxycarbazone-sodium, propoxycarbazone, or thiencarbazone-methyl; and glyphosate, glyphosate-sodium, glyphosate-potassium, glyphosate-ammonium, glyphosate-diammonium, glyphosate-isopropylammonium, glyphosate-trimesium, glyphosate-sesquisodium, glufosinate, glufosinate-ammonium, glufosinate-P, glufosinate-P-ammonium, glufosinate-P-sodium, bilanafos, bilanafos-sodium or cinmethylin.

(8) Those which are believed to exhibit herbicidal effects by inhibiting cell mitoses of plants, such as a dinitroaniline compound such as trifluralin, oryzalin, nitralin, pendimethalin, ethalfluralin, benfluralin, prodiamine, butralin or dinitramine; an amide compound such as bensulide, napropamide, napropamide-M, propyzamide or pronamide; an organic phosphorus compound such as amiprofos-methyl, butamifos, anilofos or piperophos; a phenyl carbamate compound such as propham, chlorpropham, barban or carbetamide; a cumylamine compound such as daimuron, cumyluron, bromobutide or methyldymron; and asulam, asulam-sodium, dithiopyr, thiazopyr, chlorthal-dimethyl, chlorthal, diphenamid, flamprop-M-methyl, flamprop-M, or flamprop-M-isopropyl.

(9) Those which are believed to exhibit herbicidal effects by inhibiting protein biosynthesis or lipid biosynthesis of plants, such as a chloroacetamide compound such as alachlor, metazachlor, butachlor, pretilachlor, metolachlor, S-metolachlor, thenylchlor, pethoxamid, acetochlor, propachlor, dimethenamide, dimethenamide-P, propisochlor or dimethachlor; a thiocarbamate compound such as molinate, dimepiperate, pyributicarb, EPTC, butylate, vernolate, pebulate, cycloate, prosulfocarb, esprocarb, thiobencarb, diallate, tri-allate or orbencarb; and etobenzanid, mefenacet, flufenacet, tridiphane, cafenstrole, fentrazamide, oxaziclomefone, indanofan, benfuresate, pyroxasulfone, fenoxasulfone, methiozolin, dalapon, dalapon-sodium, TCA-sodium or trichloroacetic acid.

(10) Those which are believed to exhibit herbicidal effects by inhibiting a cellulose biosynthesis of plants, such as dichlobenil, triaziflam, indaziflam, flupoxam, or isoxaben.

(11) MSMA, DSMA, CMA, endothall, endothall-dipotassium, endothall-sodium, endothall-mono(N,N-dimethylalkylammonium), ethofumesate, sodium chlorate, pelargonic acid, nonanoic acid, fosamine, fosamine-ammonium, ipfencarbazone, aclolein, ammonium sulfamate, borax, chloroacetic acid, sodium chloroacetate, cyanamide, methylarsonic acid, dimethylarsinic acid, sodium dimethylarsinate, dinoterb, dinoterb-ammonium, dinoterb-diolamine, dinoterb-acetate, DNOC, ferrous sulfate, flupropanate, flupropanate-sodium, mefluidide, mefluidide-diolamine, metam, metam-ammonium, metam-potassium, metam-sodium, methyl isothiocyanate, pentachlorophenol, sodium pentachlorophenoxide, pentachlorophenol laurate, quinoclamine, sulfuric acid, urea sulfate, xanthinosin, herbimycin, unguinol, metatyrosine, sarmentine, thaxtomin A, mevalocidin, alpha-limonene, pyribambenz-propyl, pyribambenz-isopropyl, JS-913, KHG-23844, H-9201, SIOC-0163, SIOC-0171, SIOC-0172, SIOC-0285, SIOC-0426, SIOC-H-057, ZJ-0166, ZJ-1835, ZJ-0453, ZJ-0777, ZJ-0862, a compound disclosed in WO2008/096398 (Kumiai Chemical).

(12) Those which are believed to exhibit herbicidal effects by being parasitic on plants, such as *Xanthomonas campestris, Epicoccosirus nematosorus, Epicoccosirus nematosperus, Exserohilum monoseras*, or *Drechsrela monoceras*.

One or more compounds may properly be selected from among the above compounds which are active compounds of other herbicides. The active compounds of other herbicides are not limited to the above-exemplified compounds.

EXAMPLES

Now, the present invention will be described in further detail with reference to Examples, but it should be understood that the present invention is by no means restricted to such Examples. Firstly, Preparation Examples for the compounds of the present invention will be described.

Preparation Example 1

Preparation of 4-(5-((3-chloro-5-(trifluoromethyl)pyridin-2-yl)thio)-2-methylphenyl)-5-methoxy-2,6-dimethylpyridazin-3(2H)-one (after-mentioned compound No. 1-32)

(1) Under a nitrogen atmosphere, diisopropylethylamine (1.2 mL) was added to a mixed solution of 2-bromo-4-iodo-1-methylbenzene (1.0 g), (4-methoxyphenyl)methanethiol (520 mg), tris(dibenzylideneacetone)dipalladium (80 mg), 4,5-bis(diphenylphosphino)-9,9-dimethylxanthene (100 mg) and 1,4-dioxane (10 mL), followed by reaction under reflux for 1 hour. The resulting reaction mixture was cooled, mixed with water and extracted twice with ethyl acetate (30 mL). The resulting organic layer was washed with a brine and dried over anhydrous sodium sulfate, the solvent was distilled off under reduced pressure, and the obtained residue was purified by column chromatography (heptane:ethyl acetate=20:1, volume ratio, the same applies hereinafter) to obtain (3-bromo-4-methylphenyl) (4-methoxybenzyl)sulfane (1.07 g, yield: 98%) as a brown oil. NMR spectrum data of this product are as follows.

$^1$H NMR (300 MHz, CDCl$_3$): δ ppm=2.35 (3H, s), 3.79 (3H, s), 4.04 (2H, s), 6.83 (2H, d, J=8.7 Hz), 7.08-7.21 (4H, m), 7.48 (1H, d, J=0.6 Hz)

(2) Under a nitrogen atmosphere, a mixed solution of (3-bromo-4-methylphenyl) (4-methoxybenzyl)sulfane (1.07 g), bis(pinacolato)diboron (1.26 g), tris(dibenzylideneacetone)dipalladium (120 mg), tricyclohexylphosphine (150 mg), potassium acetate (490 mg) and 1,4-dioxane (15 ml) was reacted at 120° C. for 7 hours. The reaction mixture was cooled, an insoluble solid was removed by Celite, and the solid matter was washed with ethyl acetate. The solvent was distilled off under reduced pressure, and the obtained residue was purified by column chromatography (heptane:ethyl acetate=20:1) to obtain 2-(5-((4-methoxybenzyl)thio)-2-methylphenyl)-4,4,5,5-tetramethyl-1,3,2-dioxaborolane (1.07 g, yield: 87%) as a white solid. NMR spectrum data of this purified product are as follows.

$^1$H NMR (300 MHz, CDCl$_3$): δ ppm=1.38 (12H, s), 2.48 (3H, s), 3.77 (3H, s), 4.03 (2H, s), 6.80 (2H, d, J=8.4 Hz), 7.04 (1H, d, J=8.1 Hz), 7.17-7.27 (3H, m), 7.76 (1H, dd, J=1.5 Hz, J=6.6 Hz)

(3) A mixed solution of 2-(5-((4-methoxybenzyl)thio)-2-methylphenyl)-4,4,5,5-tetramethyl-1,3,2-dioxaborolane (381 mg), 4-bromo-5-methoxy-2,6-dimethylpyridazin-3(2H)-one (200 mg), tetrakis(triphenylphosphine)palladium (40 mg), sodium carbonate (200 mg), tetrabutylammonium bromide (144 mg), 1,4-dioxane (6 ml) and water (4 mL) was reacted at 120° C. for 45 minutes. The reaction mixture was cooled, mixed with water and extracted twice with ethyl acetate (20 ml). The resulting organic layer was washed with a brine and dried over anhydrous sodium sulfate, the solvent was distilled off under reduced pressure, and the obtained residue was purified by column chromatography (heptane:ethyl acetate=1:1) to obtain 5-methoxy-4-(5-((4-methoxybenzyl)thio)-2-methylphenyl)-2,6-dimethylpyridazin-3(2H)-one (275 mg, yield: 81%) as a white solid. NMR spectrum data of this purified product are as follows.

$^1$H NMR (300 MHz, CDCl$_3$): δ ppm=2.16 (3H, s), 2.27 (3H, s), 3.24 (3H, s), 3.68 (3H, s), 3.77 (3H, s), 4.03 (2H, s), 6.79 (2H, d, J=8.7 Hz), 7.15-7.26 (5H, m)

(4) 5-methoxy-4-(5-((4-methoxybenzyl)thio)-2-methylphenyl)-2,6-dimethylpyridazin-3(2H)-one (275 mg) was dissolved in trifluoroacetic acid (2 ml) and reacted at 60° C. for 3 hours. The reaction mixture was cooled, and the solvent was distilled off under reduced pressure to obtain 4-(5-mercapto-2-methylphenyl)-5-methoxy-2,6-dimethylpyridazin-3(2H)-one (190 mg, yield: 99%) as a brown solid.

(5) A mixed solution of 4-(5-mercapto-2-methylphenyl)-5-methoxy-2,6-dimethylpyridazin-3(2H)-one (190 mg) obtained in the above step (4), 2,3-dichloro-5-(trifluoromethyl)pyridine (223 mg), cesium carbonate (336 mg) and dimethylformamide (5 ml) was reacted at 60° C. for 3 hours. The reaction mixture was cooled, mixed with water and extracted twice with ethyl acetate (20 ml). The resulting organic layer was washed with a brine and dried over anhydrous sodium sulfate, the solvent was distilled off under reduced pressure, and the obtained residue was purified by column chromatography (heptane:ethyl acetate=3:2) to obtain the desired product (122 mg, yield: 39%) as a white solid. NMR spectrum data of the purified product are as follows.

$^1$H NMR (300 MHz, CDCl$_3$): δ ppm=2.24 (3H, s), 2.30 (3H, s), 3.53 (3H, s), 3.73 (3H, s), 7.36-7.38 (2H, m), 7.48 (1H, dd, J=2.1 Hz, J=8.4 Hz), 7.76 (1H, dd, J=0.6 Hz, J=2.1 Hz), 8.33 (1H, dd, J=0.9 Hz, J=1.8 Hz)

Preparation Example 2

Preparation of 4-(5-((3-chloro-5-(trifluoromethyl)pyridin-2-yl)thio)-2-methylphenyl)-5-hydroxy-2,6-dimethylpyridazin-3(2H)-one (after-mentioned compound No. 1-2)

4-(5-((3-chloro-5-(trifluoromethyl)pyridin-2-yl)thio)-2-methylphenyl)-5-methoxy-2,6-dimethylpyridazin-3(2H)-one (122 mg) was dissolved in morpholine (2 ml), sealed in a tube and reacted under irradiation with microwaves at 140° C. for 50 minutes. After completion of the reaction, excess morpholine was distilled off, the residue was acidified with acetic acid, and the aqueous layer was extracted twice with ethyl acetate (10 ml). The resulting organic layer was dried over sodium sulfate, the solvent was distilled off under reduced pressure, and the obtained residue was purified by column chromatography (heptane:ethyl acetate=1:1) to obtain the desired product (51 mg, yield: 43%) as a white solid. This product had a melting point of from 99 to 102° C., and its NMR spectrum data are as follows.

$^1$H NMR (300 MHz, CDCl$_3$): δ ppm=2.24 (3H, s), 2.30 (3H, s), 3.73 (3H, s), 7.36-7.48 (3H, m), 7.79 (1H, d, J=1.8 Hz), 8.32 (1H, dd, J=0.9 Hz, J=1.8 Hz)

Typical examples of the compounds of the present invention are shown in Tables 1 to 3. These compounds may be prepared in accordance with the above Preparation Examples or Production Processes. In Tables 1 to 3, No. represents compound No., Me a methyl group, Et an ethyl group, Pr a n-propyl group, i-Pr an isopropyl group, n-Bu a n-butyl group, t-Bu a tert-butyl group, c-Pr a cyclopropyl group, c-Hex a cyclohexyl group, Ph a phenyl group, and Bn a benzyl group, respectively. Further, "2,6-(Me)$_2$" in Tables means that methyl groups as substituents are on 2- and 6-positions, respectively, and the same applies hereinafter.

The numerical values described in the column "physical properties" in Tables 1 to 3 represent melting points (° C.), and of compounds with NMR in the column "physical properties", $^1$H-NMR spectrum data are shown in Table 4.

TABLE 1

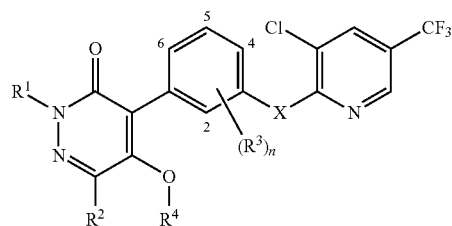

| No. | R$^1$ | R$^2$ | R$^3$ | R$^4$ | X | Physical properties |
|---|---|---|---|---|---|---|
| 1-1 | Me | Me | 6-Me | H | O | 102-105 |
| 1-2 | Me | Me | 6-Me | H | S | 99-102 |
| 1-3 | Me | Me | 6-Et | H | O | 94-96 |
| 1-4 | Me | Me | 6-Et | H | S | 109-111 |
| 1-5 | Me | Me | 6-Pr | H | O | |
| 1-6 | Me | Me | 6-i-Pr | H | O | |
| 1-7 | Me | Me | 6-t-Bu | H | O | |
| 1-8 | Me | Me | 6-CF$_3$ | H | O | |
| 1-9 | Me | Me | 6-c-Pr | H | O | |
| 1-10 | Me | Me | 6-OMe | H | O | 133 |
| 1-11 | Me | Me | 6-Cl | H | O | |
| 1-12 | Me | Me | 2-Me | H | O | 190 |
| 1-13 | Me | Me | 2,6-(Me)$_2$ | H | O | 90 |
| 1-14 | Me | Me | 4,6-(Me)$_2$ | H | O | 94 |
| 1-15 | Me | Me | 4-Me | H | O | |
| 1-16 | Me | Me | 6-Pr | H | S | |
| 1-17 | Me | Me | 6-i-Pr | H | S | |
| 1-18 | Me | Me | 6-t-Bu | H | S | |
| 1-19 | Me | Me | 6-CF$_3$ | H | S | |
| 1-20 | Me | Me | 6-c-Pr | H | S | |
| 1-21 | Me | Me | 6-OMe | H | S | |
| 1-22 | Me | Me | 6-Cl | H | S | |
| 1-23 | Me | Me | 2-Me | H | S | |
| 1-24 | Me | Me | 2,6-(Me)$_2$ | H | S | |
| 1-25 | Me | Me | 4,6-(Me)$_2$ | H | S | |
| 1-26 | Me | Me | 4-Me | H | S | |
| 1-27 | Me | Me | 6-Me | Me | O | NMR |
| 1-28 | Me | Me | 6-Et | Me | O | NMR |
| 1-29 | Me | Me | 2-Me | Me | O | NMR |
| 1-30 | Me | Me | 6-Pr | Me | O | |
| 1-31 | Me | Me | 6-i-Pr | Me | O | |
| 1-32 | Me | Me | 6-Me | Me | S | NMR |
| 1-33 | Me | Me | 6-Et | Me | S | |
| 1-34 | Me | Me | 6-Pr | Me | S | |
| 1-35 | Me | Me | 6-i-Pr | Me | S | |
| 1-36 | Me | Me | 6-t-Bu | Me | O | |
| 1-37 | Me | Me | 6-CF$_3$ | Me | O | |
| 1-38 | Me | Me | 6-t-Bu | Me | S | |
| 1-39 | Me | Me | 6-CF$_3$ | Me | S | |
| 1-40 | Me | Me | 6-Me | COMe | O | NMR |
| 1-41 | Me | Me | 6-Me | COOEt | O | NMR |
| 1-42 | Me | Me | 6-Me | COMe | S | 127-130 |
| 1-43 | Me | Me | 6-Me | COOEt | S | |
| 1-44 | Me | Me | 2-Me | COMe | O | 118 |
| 1-45 | Me | Me | 6-Et | COMe | O | 138 |
| 1-46 | Me | Me | 6-Et | COMe | S | 174 |
| 1-47 | Me | Me | 6-Me | COEt | O | |
| 1-48 | Me | Me | 6-Et | COEt | O | |
| 1-49 | Me | Me | 6-Me | COi-Pr | O | |
| 1-50 | Me | Me | 6-Et | COi-Pr | O | |

TABLE 1-continued

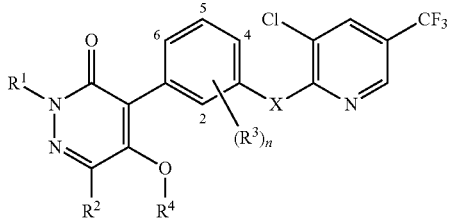

| No. | R¹ | R² | R³ | R⁴ | X | Physical properties |
|---|---|---|---|---|---|---|
| 1-51 | Me | Me | 6-Me | COt-Bu | O | |
| 1-52 | Me | Me | 6-Et | COt-Bu | O | |
| 1-53 | Me | Me | 6-Me | COOMe | O | |
| 1-54 | Me | Me | 6-Et | COOMe | O | |
| 1-55 | Me | Me | 6-Me | COOEt | O | |
| 1-56 | Me | Me | 6-Et | COOEt | O | |
| 1-57 | Me | Me | 6-Me | COOi-Pr | O | |
| 1-58 | Me | Me | 6-Et | COOi-Pr | O | |
| 1-59 | Me | Me | 6-Me | COOt-Bu | O | NMR |
| 1-60 | Me | Me | 6-Et | COOt-Bu | O | |
| 1-61 | Me | Me | 6-Me | 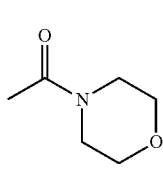 | O | |
| 1-62 | Me | Me | 6-Me | SO₂Me | O | 60 |
| 1-63 | Me | Me | 6-Et | 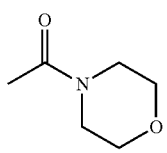 | O | |
| 1-64 | Me | Me | 6-Et | SO₂Me | O | |
| 1-65 | Et | Me | 6-Me | H | O | 97 |
| 1-66 | Et | Me | 6-Et | H | O | |
| 1-67 | i-Pr | Me | 6-Me | H | O | |
| 1-68 | i-Pr | Me | 6-Et | H | O | |
| 1-69 | Me | Me | 6-Et | COOEt | S | |
| 1-70 | Me | Me | 6-Me | COEt | S | |
| 1-71 | Me | Me | 6-Et | COEt | S | |
| 1-72 | Me | Me | 6-Me | COi-Pr | S | |
| 1-73 | Me | Me | 6-Et | COi-Pr | S | |
| 1-74 | Me | Me | 6-Me | COt-Bu | S | |
| 1-75 | Me | Me | 6-Et | COt-Bu | S | |
| 1-76 | Me | Me | 6-Me | COOMe | S | |
| 1-77 | Me | Me | 6-Et | COOMe | S | |
| 1-78 | Me | Me | 6-Me | COOEt | S | |
| 1-79 | Me | Me | 6-Et | COOEt | S | |
| 1-80 | Me | Me | 6-Me | COOi-Pr | S | |
| 1-81 | Me | Me | 6-Et | COOi-Pr | S | |
| 1-82 | Me | Me | 6-Me | COOt-Bu | S | |
| 1-83 | Me | Me | 6-Et | COOt-Bu | S | |
| 1-84 | Me | Me | 6-Me | 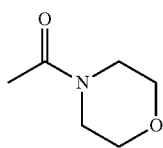 | S | |
| 1-85 | Me | Me | 6-Me | SO₂Me | S | |

TABLE 1-continued

| No. | R¹ | R² | R³ | R⁴ | X | Physical properties |
|---|---|---|---|---|---|---|
| 1-86 | Me | Me | 6-Et | (acetyl morpholine group) | S | |
| 1-87 | Me | Me | 6-Et | SO₂Me | S | |
| 1-88 | Et | Me | 6-Me | H | S | |
| 1-89 | Et | Me | 6-Et | H | S | |
| 1-90 | i-Pr | Me | 6-Me | H | S | |
| 1-91 | i-Pr | Me | 6-Et | H | S | |
| 1-92 | Me | Me | 6-Et | H | NMe | |
| 1-93 | Me | Me | 6-Et | Me | NMe | |
| 1-94 | Me | H | 6-Me | H | O | |
| 1-95 | Me | H | 6-Et | H | O | 184 |
| 1-96 | Me | H | 6-Me | Me | O | |
| 1-97 | Me | H | 6-Et | Me | O | |
| 1-98 | Me | Et | 6-Me | H | O | NMR |
| 1-99 | Me | Et | 6-Et | H | O | |
| 1-100 | Me | Et | 6-Me | Me | O | NMR |
| 1-101 | Me | Et | 6-Et | Me | O | |
| 1-102 | Me | i-Pr | 6-Me | H | O | |
| 1-103 | Me | i-Pr | 6-Et | H | O | |
| 1-104 | Me | i-Pr | 6-Me | Me | O | |
| 1-105 | Me | i-Pr | 6-Et | Me | O | |
| 1-106 | Me | t-Bu | 6-Me | H | O | |
| 1-107 | Me | t-Bu | 6-Et | H | O | |
| 1-108 | Me | t-Bu | 6-Me | Me | O | |
| 1-109 | Me | t-Bu | 6-Et | Me | O | |
| 1-110 | Me | H | 6-Me | H | S | |
| 1-111 | Me | H | 6-Et | H | S | |
| 1-112 | Me | H | 6-Me | Me | S | |
| 1-113 | Me | H | 6-Et | Me | S | |
| 1-114 | Me | Et | 6-Me | H | S | |
| 1-115 | Me | Et | 6-Et | H | S | |
| 1-116 | Me | Et | 6-Me | Me | S | |
| 1-117 | Me | Et | 6-Et | Me | S | |
| 1-118 | Me | i-Pr | 6-Me | H | S | |
| 1-119 | Me | i-Pr | 6-Et | H | S | |
| 1-120 | Me | i-Pr | 6-Me | Me | S | |
| 1-121 | Me | i-Pr | 6-Et | Me | S | |
| 1-122 | Me | t-Bu | 6-Me | H | S | |
| 1-123 | Me | t-Bu | 6-Et | H | S | |
| 1-124 | Me | t-Bu | 6-Me | Me | S | |
| 1-125 | Me | t-Bu | 6-Et | Me | S | |
| 1-126 | Me | Me | 6-c-Pr | Me | O | |
| 1-127 | Me | Me | 6-c-Pr | COMe | O | |
| 1-128 | Me | Me | 6-c-Pr | Me | S | |
| 1-129 | Me | Me | 6-c-Pr | COMe | S | |
| 1-130 | Me | Me | 6-Me | CH(Me)OCOOMe | O | NMR |
| 1-131 | Me | Me | 6-Me | CH(Me)OCOOEt | O | NMR |
| 1-132 | Me | Me | 6-Me | CH₂OMe | O | NMR |
| 1-133 | Me | Me | 6-Me | CH(Me)OCOOi-Pr | O | NMR |
| 1-134 | Me | Me | 6-Me | CH₂OCH₂CH₂OMe | O | 105 |
| 1-135 | Me | Me | 6-Me | COn-Bu | O | NMR |
| 1-136 | Me | Me | 6-Me | (acetyl dimethylpyrazole group) | O | NMR |

TABLE 1-continued

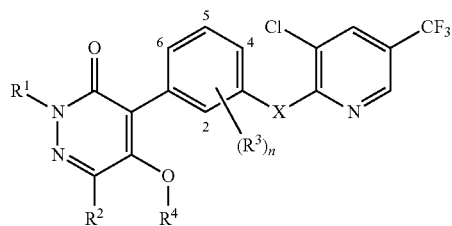

| No. | R¹ | R² | R³ | R⁴ | X | Physical properties |
|---|---|---|---|---|---|---|
| 1-137 | Me | Et | 6-Me | COMe | O | NMR |
| 1-138 | Me | Et | 6-Me | CH₂OMe | O | NMR |
| 1-139 | Me | Et | 6-Me | CH(Me)OCOOMe | O | NMR |
| 1-140 | Me | CF₃ | 6-Me | Me | O | NMR |
| 1-141 | Me | CF₃ | 6-Me | H | O | NMR |
| 1-142 | Me | CF₃ | 6-Me | COMe | O | NMR |
| 1-143 | Me | Me | 6-Me | H | NMe | 187-188 |
| 1-144 | Me | Me | 6-Me | H | NH | 199-202 |
| 1-145 | Me | Me | 6-Me | COMe | NMe | 147 |
| 1-146 | Me | Me | 6-Me | COMe | NH | 204-205 |
| 1-147 | Me | Me | 6-Me | Me | NMe | NMR |
| 1-148 | Me | Me | 6-Me | Me | NH | NMR |
| 1-149 | Me | Me | 6-c-Pr | H | O | 85-89 |
| 1-150 | Me | Me | 6-c-Pr | COMe | O | 109-112 |
| 1-151 | Me | Me | 4,6-(Me)₂ | CH(Me)OCOOMe | O | 45 |
| 1-152 | Me | Me | 4,6-(Me)₂ | COMe | O | 129 |
| 1-153 | Me | Me | H | H | O | 168 |
| 1-154 | Me | Me | 4-NO₂, 6-Me | H | O | 54 |
| 1-155 | Me | Me | 4-NO₂, 6-Me | COMe | O | 63 |
| 1-156 | Me | Me | 4-NH₂, 6-Me | COMe | O | 48 |
| 1-157 | Et | H | 6-Me | H | O | 184 |
| 1-158 | Me | Me | 4-Et, 6-Me | H | O | 98 |
| 1-159 | Me | Me | 4-Et, 6-Me | COMe | O | 144 |
| 1-160 | Me | Me | 4-COMe, 6-Me | H | O | 55 |
| 1-161 | Me | Me | 4-COMe, 6-Me | COMe | O | 62 |
| 1-162 | Me | H | 6-OCF₃ | H | O | NMR |
| 1-163 | Me | Me | 6-OCF₃ | H | O | 93 |
| 1-164 | Me | Me | 6-OCF₃ | COMe | O | 103 |
| 1-165 | Et | Me | 6-Me | COMe | O | 40 |
| 1-166 | c-Pr—CH₂— | H | 2-Me | H | O | 113 |
| 1-167 | CH₂=CHCH₂— | H | 6-Me | H | O | 79 |
| 1-168 | Me | Me | 6-OH | H | O | 96 |
| 1-169 | MeCOCH₂— | H | 6-Me | H | O | 172 |
| 1-170 | c-Pr—CH₂— | H | 2-Me | COMe | O | NMR |
| 1-171 | Me | H | 6-Me | COMe | O | NMR |
| 1-172 | 4-MeO—Bn— | H | 6-Me | H | O | 88 |
| 1-173 | Et | H | 6-Et | H | O | 164 |
| 1-174 | Et | H | 6-Et | COMe | O | 77 |
| 1-175 | MeOCH₂— | H | 6-Me | H | O | 73 |
| 1-176 | MeOCH₂— | H | 6-Me | COMe | O | NMR |
| 1-177 | Pr | H | 6-Me | H | O | 57 |
| 1-178 | Me | H | 6-Cl | H | O | 90 |
| 1-179 | Me | H | 6-CF₃ | H | O | 94 |
| 1-180 | MeOCH₂CH₂— | H | 6-Me | H | O | 67 |
| 1-181 | Et | H | 6-Me | COMe | O | NMR |
| 1-182 | MeOCH₂CH₂— | H | 6-Me | COMe | O | NMR |
| 1-183 | Me S CH₂— | Me | 6-Me | H | O | 68 |
| 1-184 | Me | H | 6-Cl | COMe | O | 120 |
| 1-185 | MeOOCCH₂— | Me | 6-Me | Me | O | NMR |
| 1-186 | MeOOCCH₂— | Me | 6-Me | COMe | O | |
| 1-187 | Me S CH₂— | Me | 6-Me | COMe | O | NMR |
| 1-188 | HOOCCH₂— | Me | 6-Me | H | O | 140-143 |

TABLE 2

| No. | R¹ | R² | R³ | R⁴ | X | Q | Physical properties |
|---|---|---|---|---|---|---|---|
| 2-1 | Me | Me | 6-Me | H | O | 3-F,5-Cl,2-Me-pyridin-yl | |
| 2-2 | Me | Me | 6-Me | H | O | 3-Cl,5-CN,2-Me-pyridin-yl | 121-124 |
| 2-3 | Me | Me | 6-Me | H | O | 5-CF₃,2-Me-pyridin-yl | 99-101 |
| 2-4 | Me | Me | 6-Me | H | O | 3-F,5-CN,2-Me-pyridin-yl | |
| 2-5 | Me | Me | 6-Me | H | O | 3-F,5-CF₃,2-Me-pyridin-yl | NMR |
| 2-6 | Me | Me | 6-Me | H | O | 3-F,5-NO₂,2-Me-pyridin-yl | |
| 2-7 | Me | Me | 6-Me | H | O | 6-Cl,3-Me-quinoxalin-yl | 202-204 |
| 2-8 | Me | Me | 6-Me | H | O | 6-Cl,2-Me-benzoxazol-yl | NMR |
| 2-9 | Me | Me | 6-Me | H | O | 2-Me-benzothiazol-yl | |
| 2-10 | Me | Me | 6-Me | H | O | 6-Cl,2-Me-benzothiazol-yl | NMR |
| 2-11 | Me | Me | 6-Me | H | O | 3-F,4-Me,5-CN-phenyl | NMR |

TABLE 2-continued

| No. | R¹ | R² | R³ | R⁴ | X | Q | Physical properties |
|---|---|---|---|---|---|---|---|
| 2-12 | Me | Me | 6-Me | H | O | 3,5-dichloro-4-methylphenyl | 105-106 |
| 2-13 | Me | Me | 6-Me | H | O | 3-chloro-4-methyl-5-(trifluoromethyl)phenyl | NMR |
| 2-14 | Me | Me | 6-Et | H | O | 5-chloro-3-fluoro-2-methylpyridin-4-yl | NMR |
| 2-15 | Me | Me | 6-Et | H | O | 5-chloro-6-methylpyridin-3-yl with CN | |
| 2-16 | Me | Me | 6-Et | H | O | 6-methyl-5-(trifluoromethyl)pyridin-3-yl | |
| 2-17 | Me | Me | 6-Et | H | O | 5-fluoro-6-methylpyridin-3-yl with CN | |
| 2-18 | Me | Me | 6-Et | H | O | 5-fluoro-6-methyl-3-(trifluoromethyl)pyridin-2-yl | |
| 2-19 | Me | Me | 6-Et | H | O | 7-chloro-3-methylquinoxalin-2-yl | |
| 2-20 | Me | Me | 6-Et | H | O | 6-chloro-2-methylbenzoxazol-2-yl | |
| 2-21 | Me | Me | 6-Et | H | O | 2-methylbenzothiazol-2-yl | |
| 2-22 | Me | H | 6-Et | H | O | 6-chloro-2-methylbenzothiazol-2-yl | |

TABLE 2-continued

| No. | R¹ | R² | R³ | R⁴ | X | Q | Physical properties |
|---|---|---|---|---|---|---|---|
| 2-23 | Me | H | 6-Et | H | O | 3-F, 4-Me, C₆H₃-CN | |
| 2-24 | Me | H | 6-Et | H | O | 2,5-diCl, 4-Me-C₆H₂ | |
| 2-25 | Me | H | 6-Et | H | O | 2-Cl, 4-Me, 5-CF₃-C₆H₂ | |
| 2-26 | Et | Me | 6-Me | H | O | 3-F, 2-Me, 5-CF₃-pyridyl | |
| 2-27 | Et | Me | 6-Et | H | O | 3-Cl, 2-Me, 5-CN-pyridyl | |
| 2-28 | i-Pr | Me | 6-Me | H | O | 3-F, 2-Me, 5-CF₃-pyridyl | |
| 2-29 | i-Pr | Me | 6-Et | H | O | 3-Cl, 2-Me, 5-CN-pyridyl | |
| 2-30 | Me | Me | 6-Me | H | S | 3-F, 2-Me, 5-CF₃-pyridyl | |
| 2-31 | Me | Me | 6-Me | H | S | 3-Cl, 2-Me, 5-CN-pyridyl | |
| 2-32 | Me | Me | 6-Me | H | S | 2-Me, 5-CF₃-pyridyl | |
| 2-33 | Me | Me | 6-Me | H | S | 3-F, 2-Me, 5-CN-pyridyl | |

TABLE 2-continued
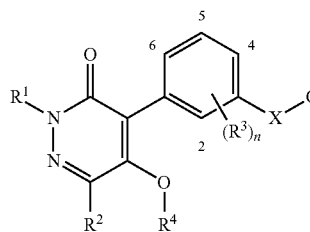
| No. | R¹ | R² | R³ | R⁴ | X | Q | Physical properties |
|---|---|---|---|---|---|---|---|
| 2-34 | Me | Me | 6-Me | H | S | 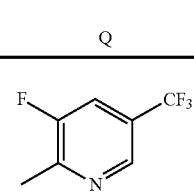 | |
| 2-35 | Me | Me | 6-Me | H | S | 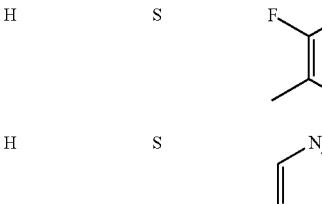 | |
| 2-36 | Me | Me | 6-Me | H | S | 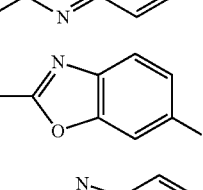 | |
| 2-37 | Me | Me | 6-Me | H | S | 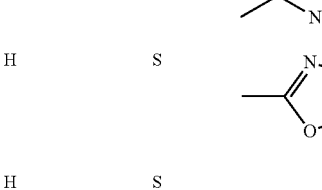 | |
| 2-38 | Me | Me | 6-Me | H | S | 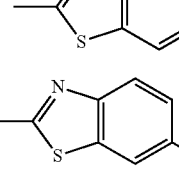 | |
| 2-39 | Me | Me | 6-Me | H | S | 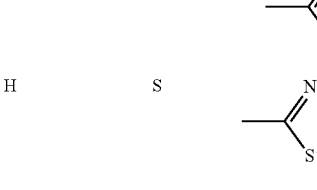 | |
| 2-40 | Me | Me | 6-Me | H | S | 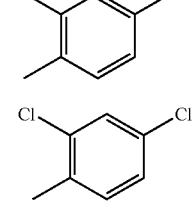 | |
| 2-41 | Me | Me | 6-Me | H | S | 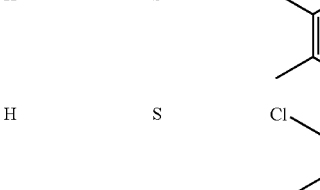 | |
| 2-42 | Me | Me | 6-Me | H | S | 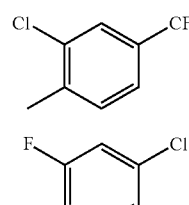 | |
| 2-43 | Me | Me | 6-Et | H | S | 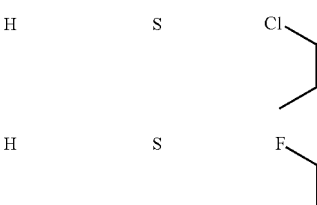 | |
| 2-44 | Me | Me | 6-Et | H | S | 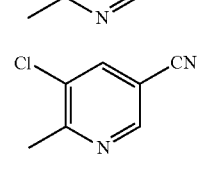 | |

TABLE 2-continued

Structure: pyridazinone core with R¹ on N, R² at position, OR⁴ group, and phenyl ring bearing (R³)ₙ and X-Q substituent (positions 2,4,5,6 labeled)

| No. | R¹ | R² | R³ | R⁴ | X | Q | Physical properties |
|---|---|---|---|---|---|---|---|
| 2-45 | Me | Me | 6-Et | H | S | 2-methyl-5-(trifluoromethyl)pyridin-yl | |
| 2-46 | Me | Me | 6-Et | H | S | 5-fluoro-6-methyl-3-cyanopyridin-yl | |
| 2-47 | Me | Me | 6-Et | H | S | 5-fluoro-6-methyl-3-(trifluoromethyl)pyridin-yl | |
| 2-48 | Me | Me | 6-Et | H | S | 6-chloro-3-methylquinoxalin-2-yl | |
| 2-49 | Me | Me | 6-Et | H | S | 6-chloro-2-methylbenzoxazol-yl | |
| 2-50 | Me | Me | 6-Et | H | S | 2-methylbenzothiazol-yl | |
| 2-51 | Me | H | 6-Et | H | S | 6-chloro-2-methylbenzothiazol-yl | |
| 2-52 | Me | H | 6-Et | H | S | 3-fluoro-4-methyl-benzonitrile-yl | |
| 2-53 | Me | H | 6-Et | H | S | 2,5-dichloro-4-methylphenyl | |
| 2-54 | Me | H | 6-Et | H | S | 2-chloro-4-(trifluoromethyl)-methylphenyl | |
| 2-55 | Et | Me | 6-Me | H | S | 3-fluoro-2-methyl-5-(trifluoromethyl)pyridin-yl | |

TABLE 2-continued
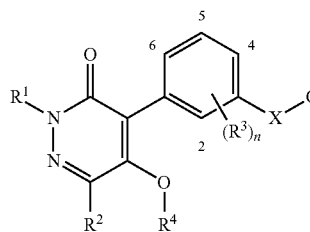
| No. | R¹ | R² | R³ | R⁴ | X | Q | Physical properties |
|---|---|---|---|---|---|---|---|
| 2-56 | Et | Me | 6-Et | H | S | 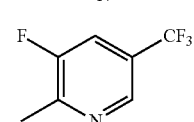 | |
| 2-57 | i-Pr | Me | 6-Me | H | S | 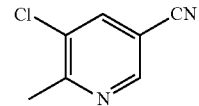 | |
| 2-58 | i-Pr | Me | 6-Et | H | S | 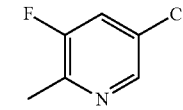 | |
| 2-59 | Me | Me | 6-Me | COMe | O | 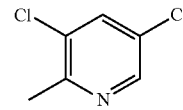 | 157 |
| 2-60 | Me | Me | 6-Me | COMe | O | 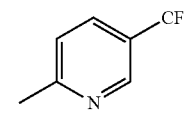 | 170 |
| 2-61 | Me | Me | 6-Me | COMe | O | 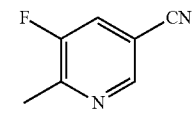 | NMR |
| 2-62 | Me | Me | 6-Me | COMe | O | 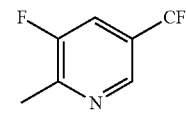 | |
| 2-63 | Me | Me | 6-Me | COMe | O | 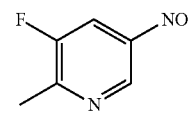 | 143-144 |
| 2-64 | Me | Me | 6-Me | COMe | O | 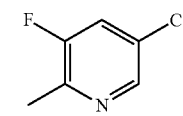 | |
| 2-65 | Me | Me | 6-Et | COMe | O | 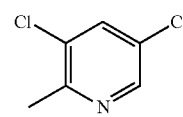 | |
| 2-66 | Me | Me | 6-Et | COMe | O |  | |

TABLE 2-continued
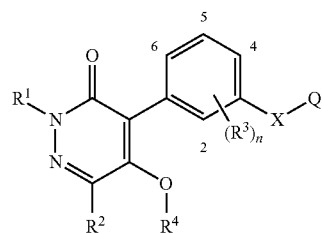
| No. | R¹ | R² | R³ | R⁴ | X | Q |
|---|---|---|---|---|---|---|
| 2-67 | Me | Me | 6-Et | COMe | O | 5-CF₃, 2-Me pyridine |
| 2-68 | Me | Me | 6-Et | COMe | O | 3-F, 2-Me, 5-CN pyridine |
| 2-69 | Me | Me | 6-Et | COMe | O | 3-F, 2-Me, 5-CF₃ pyridine |
| 2-70 | Me | Me | 6-Et | COMe | O | 3-F, 2-Me, 5-NO₂ pyridine |
| 2-71 | Me | Me | 6-Me | COMe | S | 3-F, 2-Me, 5-Cl pyridine |
| 2-72 | Me | Me | 6-Me | COMe | S | 3-Cl, 2-Me, 5-CN pyridine |
| 2-73 | Me | Me | 6-Me | COMe | S | 5-CF₃, 2-Me pyridine |
| 2-74 | Me | Me | 6-Me | COMe | S | 3-F, 2-Me, 5-CN pyridine |
| 2-75 | Me | Me | 6-Me | COW | S | 3-F, 2-Me, 5-CF₃ pyridine |
| 2-76 | Me | Me | 6-Me | COMe | S | 3-F, 2-Me, 5-NO₂ pyridine |

TABLE 2-continued

| No. | R¹ | R² | R³ | R⁴ | X | Q | Physical properties |
|---|---|---|---|---|---|---|---|
| 2-77 | Me | Me | 6-Et | COMe | S | 3-F, 5-Cl, 6-Me pyridine | |
| 2-78 | Me | Me | 6-Et | COMe | S | 3-Cl, 5-CN, 6-Me pyridine | |
| 2-79 | Me | Me | 6-Et | COMe | S | 5-CF₃, 6-Me pyridine | |
| 2-80 | Me | Me | 6-Et | COMe | S | 3-F, 5-CN, 6-Me pyridine | |
| 2-81 | Me | Me | 6-Et | COMe | S | 3-F, 5-CF₃, 6-Me pyridine | |
| 2-82 | Me | Me | 6-Et | COMe | S | 3-F, 5-NO₂, 6-Me pyridine | |
| 2-83 | Me | Me | 6-Me | H | O | 3-Br, 5-CF₃, 6-Me pyridine | 179 |
| 2-84 | Me | Me | 6-Me | H | O | 3-CF₃, 5-CF₃, 6-Me pyridine | 188-189 |
| 2-85 | Me | Me | 6-Me | H | O | 3-Cl, 2-Me, 6-CF₃ pyridine | 224-225 |
| 2-86 | Me | Me | 6-Me | H | O | 3-Cl, 2-Me, 5-CHO pyridine | NMR |

TABLE 2-continued
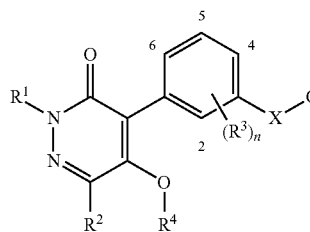
| No. | R¹ | R² | R³ | R⁴ | X | Q | Physical properties |
|---|---|---|---|---|---|---|---|
| 2-87 | Me | Me | 6-Me | H | O | 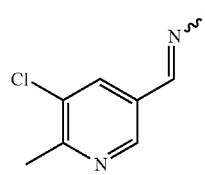 | 137-139 |
| 2-88 | Me | Me | 6-Me | H | O | 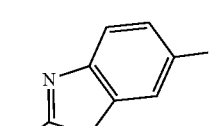 | NMR |
| 2-89 | Me | Et | 6-Me | H | O | 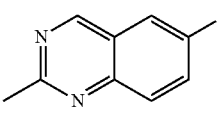 | NMR |
| 2-90 | Me | Me | 6-Me | H | O | 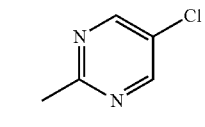 | 120-122 |
| 2-91 | Me | Me | 6-Me | H | O | 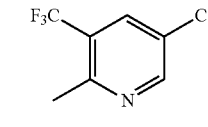 | NMR |
| 2-92 | Me | Me | 6-Me | H | O | 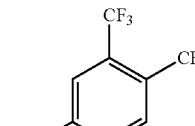 | 109-110 |
| 2-93 | Me | Me | 6-Me | H | O | 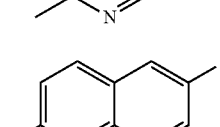 | 96-98 |
| 2-94 | Me | Me | 6-Me | H | O | 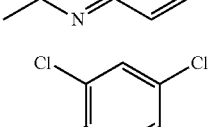 | 132-134 |
| 2-95 | Me | Me | 6-Me | H | O | 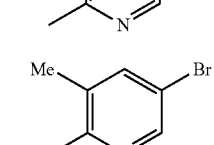 | 104-105 |
| 2-96 | Me | Me | 6-Me | H | O |  | 104-106 |

TABLE 2-continued

| No. | R¹ | R² | R³ | R⁴ | X | Q | Physical properties |
|---|---|---|---|---|---|---|---|
| 2-97 | Me | Me | 6-Me | H | O | 3-Cl-2-Me-pyridin-4-yl | 86-87 |
| 2-98 | Me | Me | 6-Me | H | O | 3-Cl-2-Me-4-CF₃-pyridin-5-yl | 120-122 |
| 2-99 | Me | Me | 6-Me | H | O | 3-Cl-2-Me-5-NO₂-pyridin-4-yl | 105-108 |
| 2-100 | Me | Me | 6-Me | H | O | 4-CF₃-5-Me-6-CF₃-pyridin-3-yl | NMR |
| 2-101 | Me | Me | 6-Me | H | O | 3-Cl-2-Me-5-Br-pyridin-4-yl | 166-168 |
| 2-102 | Me | Me | 6-Me | H | O | 3-Cl-2-Me-5-Me-pyridin-4-yl | 102-105 |
| 2-103 | Me | Me | 6-Me | H | O | 3-Me-6-CF₃-pyridazin-4-yl | NMR |
| 2-104 | Me | Me | 6-Me | H | O | 2-Me-benzoxazol-? | NMR |
| 2-105 | Me | Me | 6-Me | H | O | 5-Cl-2-Me-benzoxazol-? | NMR |

TABLE 2-continued
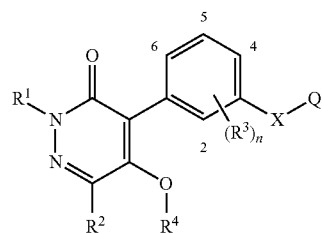
| No. | R¹ | R² | R³ | R⁴ | X | Q | Physical properties |
|---|---|---|---|---|---|---|---|
| 2-106 | Me | Me | 6-Me | H | O | (2-methylbenzimidazol-1-yl, N-Me) | 116-121 |
| 2-107 | Me | Me | 6-Me | H | O | (2-methyl-5-CF₃-thiazolo[5,4-b]pyridin-yl) | 113-118 |
| 2-108 | Me | Me | 6-Me | H | O | (2-methylquinolin-yl) | 105-108 |
| 2-109 | Me | Me | 6-Me | H | O | (2,4-dimethylquinolin-yl) | 223-224 |
| 2-110 | Me | Me | 6-Me | H | O | (1-methylisoquinolin-yl) | 108-112 |
| 2-111 | Me | Me | 6-Me | H | O | (3-methylisoquinolin-yl) | 110-112 |
| 2-112 | Me | Me | 6-Me | H | O | (3-methylquinolin-yl) | NMR |
| 2-113 | Me | Me | 6-Me | H | O | (4-methyl-1,8-naphthyridin-yl) | 132-133 |

TABLE 2-continued

| No. | R¹ | R² | R³ | R⁴ | X | Q | Physical properties |
|---|---|---|---|---|---|---|---|
| 2-114 | Me | Me | 6-Me | COMe | O | 2-Cl,4-CF₃-phenyl | 142 |
| 2-115 | Me | Me | 6-Me | COMe | O | 3-Br,5-CF₃-pyridin-2-yl | NMR |
| 2-116 | Me | Me | 6-Me | COMe | O | 3-CF₃,5-CF₃-pyridin-2-yl | NMR |
| 2-117 | Me | Me | 6-Me | COMe | O | 3-Cl,6-CF₃-pyridin-2-yl | NMR |
| 2-118 | Me | Me | 6-Me | COMe | O | 4-CF₃-phenyl | NMR |
| 2-119 | Me | Me | 6-Me | COMe | O | 2,4-diCl-phenyl | 148-149 |
| 2-120 | Me | Me | 6-Me | COMe | O | 3-F,4-CN-phenyl | NMR |
| 2-121 | Me | Me | 6-Me | COMe | O | 2-Me-5-CF₃-oxazolo[5,4-b]pyridinyl | 186-187 |
| 2-122 | Me | Et | 6-Me | COMe | O | 2-Me-6-Cl-benzoxazolyl | 166-168 |
| 2-123 | Me | Me | 6-Me | COMe | O | 2-Me-6-Br-quinazolinyl | 207-208 |

TABLE 2-continued

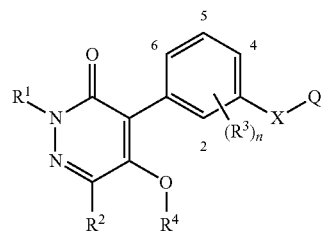

| No. | R¹ | R² | R³ | R⁴ | X | Q | Physical properties |
|---|---|---|---|---|---|---|---|
| 2-124 | Me | Me | 6-Me | COMe | O | 5-Cl-2-Me-pyrimidin-2-yl | 193 |
| 2-125 | Me | Me | 6-Me | COMe | O | 3-CF₃-5-Cl-6-Me-pyridin-2-yl | NMR |
| 2-126 | Me | Me | 6-Me | COMe | O | 3,4-bis(CF₃)-6-Me-pyridin-2-yl | NMR |
| 2-127 | Me | Me | 6-Me | COMe | O | 6-Br-2-Me-quinolin-2-yl | 170-171 |
| 2-128 | Me | Me | 6-Me | COMe | O | 3,5-diCl-6-Me-pyridin-2-yl | 166 |
| 2-129 | Me | Me | 6-Me | COMe | O | 3-Me-5-Br-6-Me-pyridin-2-yl | NMR |
| 2-130 | Me | Me | 6-Me | COMe | O | 3-Cl-6-Me-pyridin-2-yl | 173 |
| 2-131 | Me | Me | 6-Me | COMe | O | 3-Cl-4-CF₃-6-Me-pyridin-2-yl | 140 |
| 2-132 | Me | Me | 6-Me | COMe | O | 6-Cl-2-Me-benzothiazol-2-yl | 143-144 |
| 2-133 | Me | Me | 6-Me | COMe | O | 3-Cl-5-NO₂-6-Me-pyridin-2-yl | NMR |

TABLE 2-continued
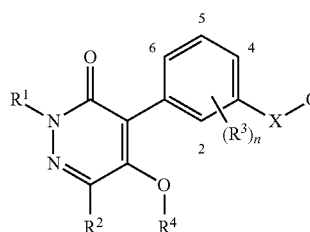
| No. | R¹ | R² | R³ | R⁴ | X | Q | Physical properties |
|---|---|---|---|---|---|---|---|
| 2-134 | Me | Me | 6-Me | COMe | O | 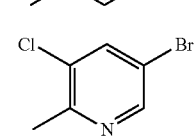 | NMR |
| 2-135 | Me | Me | 6-Me | COMe | O | 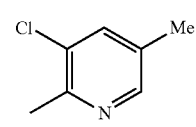 | NMR |
| 2-136 | Me | Me | 6-Me | COMe | O | 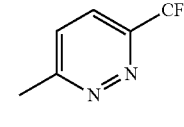 | 179-180 |
| 2-137 | Me | Me | 6-Me | COMe | O | 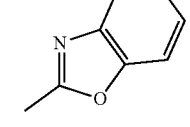 | 160-161 |
| 2-138 | Me | Me | 6-Me | COMe | O | 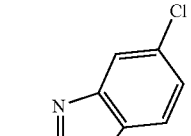 | 191-192 |
| 2-139 | Me | Me | 6-Me | COMe | O | 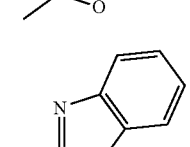 | 149-152 |
| 2-140 | Me | Me | 6-Me | COMe | O | 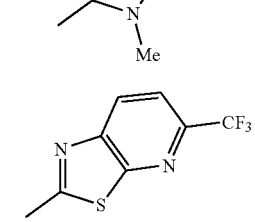 | 202 |
| 2-141 | Me | Me | 6-Me | COMe | O | 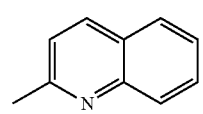 | 137-141 |
| 2-142 | Me | Me | 6-Me | COMe | O |  | 127-129 |

TABLE 2-continued
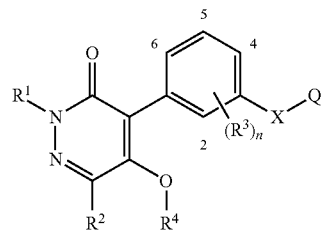
| No. | R¹ | R² | R³ | R⁴ | X | Q | Physical properties |
|---|---|---|---|---|---|---|---|
| 2-143 | Me | Me | 6-Me | COMe | O | 2-Me, 4-Me quinoline | 167-168 |
| 2-144 | Me | Me | 6-Me | COMe | O | 1-Me isoquinoline | 198-199 |
| 2-145 | Me | Me | 6-Me | COMe | O | 3-Me isoquinoline | 143 |
| 2-146 | Me | Me | 6-Me | COMe | O | 3-Me quinoline | 147 |
| 2-147 | Me | Me | 6-Me | COMe | O | 4-Me quinoline | 207-208 |
| 2-148 | Me | Me | 6-Me | COMe | O | N-OC(O)Me on (5-Cl,6-Me)pyridyl-CH= | 181-182 |
| 2-149 | Me | Me | 6-Me | CH₂OMe | O | N-OCH₂OMe on (5-Cl,6-Me)pyridyl-CH= | NMR |
| 2-150 | Me | Me | 6-Et | H | O | 2-Me-6-Cl benzothiazole | 95-99 |

TABLE 2-continued

| No. | R¹ | R² | R³ | R⁴ | X | Q | Physical properties |
|---|---|---|---|---|---|---|---|
| 2-151 | Me | Me | 6-Me | H | O | 2-methyl-6-methyl-benzothiazol-5-yl | 115 |
| 2-152 | Me | Me | 6-Me | COMe | O | 2-methyl-6-methyl-benzothiazol-5-yl | 157 |
| 2-153 | Me | Me | 6-Me | H | O | 2-methyl-6-methoxy-benzothiazol-5-yl | 94 |
| 2-154 | Me | Me | 6-Me | COMe | O | 2-methyl-6-methoxy-benzothiazol-5-yl | 146 |
| 2-155 | Me | Me | 6-Me | H | O | 2-methyl-6-fluoro-benzothiazol-5-yl | 198 |
| 2-156 | Me | Me | 6-Me | H | O | 2-methyl-6-bromo-benzothiazol-5-yl | 123 |
| 2-157 | Me | Me | 6-Me | COMe | O | 2-methyl-6-fluoro-benzothiazol-5-yl | 188 |
| 2-158 | Me | Me | 6-Me | COMe | O | 2-methyl-6-bromo-benzothiazol-5-yl | 147 |
| 2-159 | Me | Me | 6-Et | COMe | O | 2-methyl-6-chloro-benzoxazol-5-yl | 163 |
| 2-160 | Me | H | 6-Et | COMe | O | 2-methyl-6-chloro-benzoxazol-5-yl | NMR |
| 2-161 | Me | Me | 6-Et | H | O | 2-methyl-5-chloro-benzoxazol-6-yl | 86-90 |

TABLE 2-continued

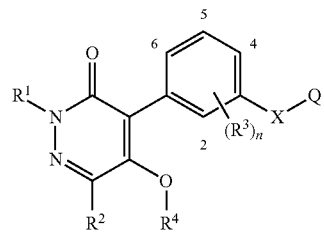

| No. | R¹ | R² | R³ | R⁴ | X | Q | Physical properties |
|---|---|---|---|---|---|---|---|
| 2-162 | Me | Me | 6-Et | H | O | 5-Cl-2-methylbenzoxazol-2-yl | 176 |
| 2-163 | Me | H | 6-Me | H | O | 6-Cl-2-methylbenzoxazol-2-yl | 250 |
| 2-164 | Me | H | 6-Me | COMe | O | 6-Cl-2-methylbenzoxazol-2-yl | NMR |
| 2-165 | Me | Me | 6-Et | H | O | 2-methylbenzoxazol-2-yl | 95 |
| 2-166 | Me | Me | 6-Et | H | O | 2-methylbenzoxazol-2-yl | 147 |
| 2-167 | Et | H | 6-Me | H | O | 6-Cl-2-methylbenzoxazol-2-yl | 239 |
| 2-168 | Ph | H | 6-Me | H | O | 6-Cl-2-methylbenzoxazol-2-yl | 234 |
| 2-169 | Et | H | 6-Me | COMe | O | 6-Cl-2-methylbenzoxazol-2-yl | 131 |
| 2-170 | Ph | H | 6-Me | COMe | O | 6-Cl-2-methylbenzoxazol-2-yl | 63 |
| 2-171 | i-Pr | H | 6-Me | H | O | 6-Cl-2-methylbenzoxazol-2-yl | 229 |
| 2-172 | i-Pr | H | 6-Me | COMe | O | 6-Cl-2-methylbenzoxazol-2-yl | NMR |

TABLE 2-continued
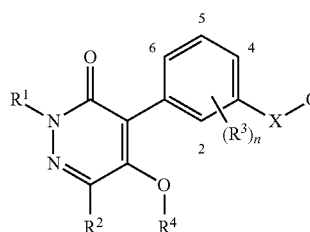
| No. | R¹ | R² | R³ | R⁴ | X | Q | Physical properties |
|---|---|---|---|---|---|---|---|
| 2-173 | Me | H | 6-Me | H | O | 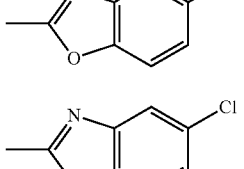 | 99 |
| 2-174 | Me | H | 6-Me | COMe | O | 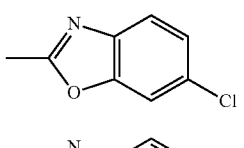 | 114 |
| 2-175 | Me | Me | 6-OCF₃ | H | O | 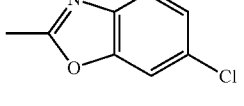 | 92 |
| 2-176 | Et | Me | 6-Me | H | O | 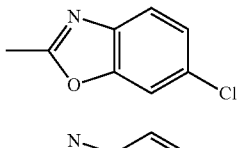 | 92 |
| 2-177 | Et | Me | 6-Me | COMe | O | 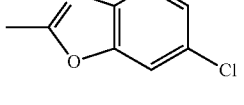 | 138 |
| 2-178 | Me | H | 6-Me | CH(Me)OCOOMe | O | 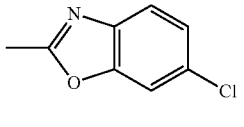 | 40-42 |
| 2-179 | CHF₂CH₂— | H | 6-Me | H | O | 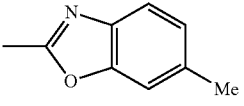 | 210 |
| 2-180 | Me | H | 6-Me | H | O | 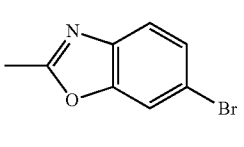 | 186-189 |
| 2-181 | Me | H | 6-Me | H | O | 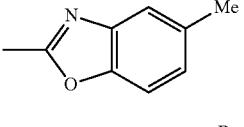 | 250 |
| 2-182 | Me | H | 6-Me | H | O | 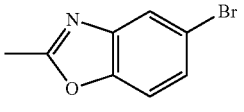 | 140 |
| 2-183 | Me | H | 6-Me | H | O |  | 105 |

TABLE 2-continued

| No. | R¹ | R² | R³ | R⁴ | X | Q | Physical properties |
|---|---|---|---|---|---|---|---|
| 2-184 | Me | H | 6-Me | H | O | 2-methyl-5-fluoro-benzoxazole | 210 |
| 2-185 | Me | H | 6-Me | H | O | 2-methyl-7-chloro-benzoxazole | 150 |
| 2-186 | c-Pr—CH₂— | H | 6-Me | H | O | 2-methyl-6-chloro-benzoxazole | 211 |
| 2-187 | Me | Me | 6-Et | H | O | methyl 5-chloro-6-methyl-nicotinate | 183 |
| 2-188 | Me | Me | 6-Et | H | O | 5-chloro-6-methyl-N,N-diethyl-nicotinamide | 55 |
| 2-189 | Me | Me | 6-Et | COMe | O | methyl 5-chloro-6-methyl-nicotinate | 138 |
| 2-190 | Me | Me | 6-Et | COMe | O | 5-chloro-6-methyl-N,N-diethyl-nicotinamide | NMR |
| 2-191 | Me | Me | 6-Me | H | O | 3-chloro-2-methyl-5-(methylsulfonyl)pyridine | 140 |
| 2-192 | Ph | H | 6-Me | COMe | O | 2-methyl-6-chloro-benzoxazole | 63 |

TABLE 2-continued

| No. | R¹ | R² | R³ | R⁴ | X | Q | Physical properties |
|---|---|---|---|---|---|---|---|
| 2-193 | Me | Me | 6-Me | H | O | 6-methyl-2-chloro-imidazo[1,2-b]pyridazine | NMR |
| 2-194 | Me | Me | 6-Me | H | O | 5-methyl-2-(trifluoromethyl)pyrazine | NMR |
| 2-195 | Me | Me | 6-Me | COMe | O | 5-methyl-2-(trifluoromethyl)pyrazine | NMR |
| 2-196 | Me | Me | 6-Me | H | O | 2-methyl-5-chloro-thiazole | 149-150 |
| 2-197 | Me | Me | 6-Me | COMe | O | 2-methyl-5-chloro-thiazole | 137-138 |
| 2-198 | Me | Me | 6-Me | H | O | 6-methyl-2-chloro-pyrido[3,2-d]pyrimidine | NMR |
| 2-199 | Me | Me | 6-Me | COMe | O | 6-methyl-2-chloro-pyrido[3,2-d]pyrimidine | 183-185 |
| 2-200 | Me | Me | 6-Me | Me | O | 3-methyl-2,7-dichloro-pyrido[2,3-b]pyrazine | 229-230 |
| 2-201 | Me | Me | 6-Me | Me | O | 2-methyl-pyrido[3,2-d]pyrimidine | |
| 2-202 | Me | Me | 6-Me | Me | O | 2-methyl-6-chloro-1,5-naphthyridine | |

TABLE 2-continued

| No. | R¹ | R² | R³ | R⁴ | X | Q | Physical properties |
|---|---|---|---|---|---|---|---|
| 2-203 | Me | Me | 6-Me | Me | O | [6-chloro-[1,2,4]triazolo[1,5-a]pyridin-2-yl with methyl] | |
| 2-204 | Me | Me | 6-Me | Me | O | [chloro-methyl pyrido-pyrazine] | |
| 2-205 | Me | Me | 6-Me | Me | O | [6-chloro-2-methyl-imidazo[1,2-a]pyridine] | 173-175 |

TABLE 3

| No. | R¹ | R² | R³ | R⁴ | X | Physical properties |
|---|---|---|---|---|---|---|
| 3-1 | Me | Me | 6-Me | H | O | 202-204 |
| 3-2 | Me | Me | 6-Me | H | S | |
| 3-3 | Me | Me | 6-Et | H | O | |
| 3-4 | Me | Me | 6-Et | H | S | |
| 3-5 | Me | Me | 6-Pr | H | O | |
| 3-6 | Me | Me | 6-i-Pr | H | O | |
| 3-7 | Me | Me | 6-t-Bu | H | O | |
| 3-8 | Me | Me | 6-CF₃ | H | O | |
| 3-9 | Me | Me | 6-c-Pr | H | O | |
| 3-10 | Me | Me | 6-OMe | H | O | |
| 3-11 | Me | Me | 6-Cl | H | O | |
| 3-12 | Me | Me | 2-Me | H | O | |
| 3-13 | Me | Me | 2,6-(Me)₂ | H | O | |
| 3-14 | Me | Me | 4,6-(Me)₂ | H | O | |
| 3-15 | Me | Me | 4-Me | H | O | |
| 3-16 | Me | Me | 6-Pr | H | S | |
| 3-17 | Me | Me | 6-i-Pr | H | S | |
| 3-18 | Me | Me | 6-t-Bu | H | S | |
| 3-19 | Me | Me | 6-CF₃ | H | S | |
| 3-20 | Me | Me | 6-c-Pr | H | S | |
| 3-21 | Me | Me | 6-OMe | H | S | |
| 3-22 | Me | Me | 6-Cl | H | S | |

TABLE 3-continued

| No. | R¹ | R² | R³ | R⁴ | X | Physical properties |
|---|---|---|---|---|---|---|
| 3-23 | Me | Me | 2-Me | H | S | |
| 3-24 | Me | Me | 2,6-(Me)₂ | H | S | |
| 3-25 | Me | Me | 4,6-(Me)₂ | H | S | |
| 3-26 | Me | Me | 4-Me | H | S | |
| 3-27 | Me | Me | 6-Me | Me | O | NMR |
| 3-28 | Me | Me | 6-Et | Me | O | |
| 3-29 | Me | Me | 2-Me | Me | O | |
| 3-30 | Me | Me | 6-Pr | Me | O | |
| 3-31 | Me | Me | 6-i-Pr | Me | O | |
| 3-32 | Me | Me | 6-Me | Me | S | |
| 3-33 | Me | Me | 6-Me | COMe | O | 192 |
| 3-34 | Me | Et | 6-Me | H | O | 164-168 |
| 3-35 | Me | Me | 6-Me | COOEt | O | NMR |
| 3-36 | Me | Me | 6-Me | COn-Bu | O | 112-113 |
| 3-37 | Me | Me | 6-Me | COc-Pr | O | NMR |
| 3-38 | Me | Me | 6-Me | COPh | O | 200-201 |
| 3-39 | Me | Me | 6-Me | (4-acetylmorpholine) | O | NMR |
| 3-40 | Me | Me | 6-Me | CH₂OMe | O | NMR |
| 3-41 | Me | Me | 6-Me | CH₂Ph | O | 128 |
| 3-42 | Me | Me | 6-Me | COt-Bu | O | 178-180 |
| 3-43 | Me | Me | 6-Me | (1,3-dimethyl-1H-pyrazol-4-yl)carbonyl | O | NMR |
| 3-44 | Me | Me | 6-Me | CH(Me)OCOOMe | O | NMR |
| 3-45 | Me | Me | 6-Me | COCH₂OMe | O | 168-169 |
| 3-46 | Me | Me | 6-Me | COCH₂CH₂COOMe | O | NMR |
| 3-47 | Me | Me | 6-Me | COCH₂Ph | O | NMR |
| 3-48 | Me | Me | 6-Me | COCH₂OPh | O | NMR |
| 3-49 | Me | Me | 6-Me | COCH=CH₂ | O | NMR |
| 3-50 | Me | Me | 6-Me | COCH₂CH₂SMe | O | 164-165 |
| 3-51 | Me | Me | 6-Me | (pyridin-2-yl)carbonyl | O | 172-175 |
| 3-52 | Me | Me | 6-Me | COCF₃ | O | NMR |
| 3-53 | Me | Me | 6-Me | COCH₂t-Bu | O | 146 |
| 3-54 | Me | Me | 6-Me | COCH=CHCl | O | NMR |
| 3-55 | Me | Me | 6-Me | COOCH₂CH₂OMe | O | NMR |
| 3-56 | Me | Me | 6-Me | COSPr | O | NMR |
| 3-57 | Me | Me | 6-Me | (4-fluorophenyl) carbonate | O | NMR |

TABLE 3-continued

| No. | R¹ | R² | R³ | R⁴ | X | Physical properties |
|---|---|---|---|---|---|---|
| 3-58 | Me | Me | 6-Me | COOCH$_2$CH=CH$_2$ | O | NMR |
| 3-59 | Me | Me | 6-Me | COOCH$_2$CH$_2$Cl | O | NMR |
| 3-60 | Me | Me | 6-Me | COOi-Pr | O | NMR |
| 3-61 | Me | Me | 6-Me | (menthyl acetate group) | O | NMR |
| 3-62 | Me | Me | 6-Me | CSOPh | O | NMR |
| 3-63 | Me | Me | 6-Me | CSSPh | O | NMR |
| 3-64 | Me | Me | 6-Me | COOCH$_2$C≡CH | O | NMR |
| 3-65 | Me | Me | 6-Me | CON(Me)$_2$ | O | NMR |
| 3-66 | Me | Me | 6-Me | CON(Me)Ph | O | 166-167 |
| 3-67 | Me | Me | 6-Me | CSN(Me)$_2$ | O | NMR |
| 3-68 | Me | Me | 6-Me | SO$_2$Et | O | 187-188 |
| 3-69 | Me | Me | 6-Me | SO$_2$CF$_3$ | O | 167-168 |
| 3-70 | Me | Me | 6-Me | SO$_2$c-Pr | O | 197-198 |
| 3-71 | Me | Me | 6-Me | SO$_2$(4-Me—Ph) | O | NMR |
| 3-72 | Me | Me | 6-Me | CH$_2$COMe | O | 186-187 |
| 3-73 | Me | Me | 6-Me | CH$_2$COPh | O | 168 |
| 3-74 | Me | Me | 6-Me | CH$_2$CH=CH$_2$ | O | 119 |
| 3-75 | Me | Me | 6-Me | CH$_2$OCH$_2$CH$_2$OMe | O | NMR |
| 3-76 | Me | Me | 6-Me | CH(Me)OCOOc-Hex | O | NMR |
| 3-77 | Me | Me | 6-Me | CH$_2$C≡CH | O | 162-164 |
| 3-78 | Me | Me | 6-Me | CH$_2$CN | O | 165 |
| 3-79 | Me | Me | 6-Me | COCOOEt | O | NMR |
| 3-80 | Me | Me | 6-Me | COCH$_2$c-Hex | O | NMR |
| 3-81 | Me | Me | 6-Me | CH$_2$OCH$_2$CH$_2$Cl | O | NMR |
| 3-82 | Me | Me | 6-Me | COC≡CH | O | NMR |
| 3-83 | Me | Me | 6-Me | COCH$_2$CH$_2$CH$_2$Cl | O | 130-131 |
| 3-84 | Me | Me | 6-Me | COCH$_2$NMe$_2$ | O | 141-142 |
| 3-85 | Me | Me | 6-Me | COCH$_2$CN | O | |
| 3-86 | Me | Me | 6-Me | COCH$_2$OCH$_2$OMe | O | |
| 3-87 | Me | Me | 6-Me | COOCH(Me)Cl | O | NMR |
| 3-88 | Me | Me | 6-Me | COOCH$_2$CH$_2$OCH$_2$c-Pr | O | |
| 3-89 | Me | Me | 6-Me | COOCH$_2$CH$_2$OCH$_2$CH$_2$OEt | O | |
| 3-90 | Me | Me | 6-Me | COOCH$_2$CH$_2$OCH$_2$Ph | O | NMR |
| 3-91 | Me | Me | 6-Me | COOCH$_2$CH$_2$OCH$_2$CH=CH$_2$ | O | |
| 3-92 | Me | Me | 6-Me | COOCH$_2$CH$_2$OCH$_2$CH$_2$SMe | O | |
| 3-93 | Me | Me | 6-Me | COOCH$_2$CH$_2$OCH$_2$CH$_2$F | O | |
| 3-94 | Me | Me | 6-Me | COOCH$_2$CH$_2$OCH$_2$CF$_3$ | O | |
| 3-95 | Me | Me | 6-Me | (pyridylmethoxyethyl acetate group) | O | |
| 3-96 | Et | Me | 6-Me | H | O | 103 |
| 3-97 | Et | Me | 6-Me | COMe | O | 173 |
| 3-98 | Me | Me | 6-Me | COOCH$_2$CH$_2$OCH$_2$CH$_2$OMe | O | NMR |
| 3-99 | Me | Me | 6-Me | COOCH$_2$CH$_2$OCH=CH$_2$ | O | NMR |
| 3-100 | Me | Me | 6-Me | COOCH$_2$CH$_2$SMe | O | NMR |
| 3-101 | Me | Me | 6-Me | COOCH$_2$CH$_2$c-r | O | NMR |
| 3-102 | Me | Me | 6-Me | COOCH$_2$CH(Me)$_2$ | O | NMR |
| 3-103 | Me | Me | 6-Me | COOC(Me)=CH$_2$ | O | 122 |

TABLE 3-continued

| No. | R¹ | R² | R³ | R⁴ | X | Physical properties |
|---|---|---|---|---|---|---|
| 3-104 | Me | Me | 6-Me | 3-acetylfuran | O | 185-186 |
| 3-105 | Me | Me | 6-Me | 2-acetylthiophene | O | NMR |
| 3-106 | Me | Me | 6-Me | 3-acetylpyridine | O | NMR |
| 3-107 | Me | Me | 6-Me | 4-acetylpyridine | O | 217 |
| 3-108 | Me | Me | 6-Me | COOCH$_2$OCH$_2$CH$_2$On-Bu | O | NMR |
| 3-109 | Me | Me | 6-Me | 2-acetylfuran | O | 207-208 |
| 3-110 | Me | Me | 6-Me | 3-acetylthiophene | O | NMR |

TABLE 4

| No. | 1H-NMR δ ppm (Solvent: CDCl$_3$) |
|---|---|
| 1-27 | $^1$H NMR (300 MHz, CDCl$_3$): δ ppm = 2.22(3H, s), 2.27(3H, s), 3.47(3H, s), 3.73(3H, s), 7.03(1H, d, J = 2.4 Hz), 7.13(1H, dd, J = 2.4 Hz, J = 8.4 Hz), 7.34(1H, d, J = 8.1 Hz), 7.95(1H, d, J = 2.1 Hz), 8.23(1H, dd, J = 0.9 Hz, J = 2.1 Hz). |
| 1-28 | $^1$H NMR (300 MHz, CDCl$_3$): δ ppm = 2.22(3H, t, J = 7.5 Hz), 2.26(3H, s), 2.46-2.65(2H, m), 3.49(3H, s), 3.74(3H, s), 7.00(1H, d, J = 2.4 Hz), 7.19(1H, dd, J = 2.7 Hz, J = 8.4 Hz), 7.40(1H, d, J = 8.4 Hz), 7.95(1H, dd, J = 0.6 Hz, J = 2.1 Hz), 8.23(1H, dd, J = 0.9 Hz, J = 1.8 Hz). |
| 1-29 | $^1$H NMR (300 MHz, CDCl$_3$): δ ppm = 1.96(3H, s), 2.29(3H, s), 3.44(3H, s), 3.68(3H, s), 7.14-7.20(2H, m), 7.32(1H, dd, J = 0.6 Hz, J = 8.1 Hz), 7.98(1H, dd, J = 0.3 Hz, J = 2.1 Hz), 8.21(1H, dd, J = 0.9 Hz, J = 2.1 Hz). |
| 1-32 | $^1$H NMR (300 MHz, CDCl$_3$): δ ppm = 2.24(3H, s), 2.30(3H, s), 3.53(3H, s), 3.73(3H, s), 7.36-7.38(2H, m), 7.48(1H, dd, J = 2.1 Hz, J = 8.4 Hz), 7.76(1H, dd, J = 0.6 Hz, J = 2.1 Hz), 8.33(1H, dd, J = 0.9 Hz, J = 1.8 Hz). |
| 1-40 | $^1$H NMR (300 MHz, CDCl$_3$): δ ppm = 2.07(3H, s), 2.21(3H, s), 2.25(3H, s), 3.82(3H, s), 6.89(1H, d, J = 2.4 Hz), 7.11(1H, dd, J = 2.7 Hz, J = 8.4 Hz), 7.33(1H, d, J = 8.4 Hz), 7.96(1H, d, J = 2.1 Hz), 8.21(1H, dd, J = 0.9 Hz, J = 2.1 Hz). |
| 1-41 | $^1$H NMR (300 MHz, CDCl$_3$): δ ppm = 1.26(3H, t, J = 7.2 Hz), 2.22(3H, s), 2.31(3H, s), 3.82(3H, s), 4.12(2H, q, J = 7.2 Hz), 6.95(1H, d, J = 2.7 Hz), 7.13(1H, d, J = 2.4 Hz, J = 8.4 Hz), 7.33(1H, d, J = 8.4 Hz), 7.95(1H, d, J = 2.1 Hz), 8.23(1H, dd, J = 1.2 Hz, J = 2.4 Hz). |

TABLE 4-continued

| No. | 1H-NMR δ ppm (Solvent: CDCl₃) |
|---|---|
| 1-59 | ¹H NMR (500 MHz, CDCl₃): δ ppm = 1.33(9H, s), 2.21(3H, s), 2.29(3H, s), 3.80(3H, s), 6.94(1H, d, J = 3.0 Hz) , 7.10(1H, dd, J = 2.5 Hz, J = 8.5 Hz), 7.31(1H, d, J = 8.5 Hz), 7.93(1H, d, J = 2.5 Hz), 8.22(1H, d, J = 1.0 Hz). |
| 1-98 | ¹H NMR (500 MHz, CDCl₃): δ ppm = 1.24(3H, t, J = 7.5 Hz), 2.20(3H, s), 2.68(2H, q, J = 7.5 Hz), 3.74(3H, s), 6.68(1H, br. s), 7.00(1H, d, J = 2.5 Hz), 7.13(1H, d, J = 8.0 Hz), 7.40(1H, d, J = 8.0 Hz), 7.97(1H, d, J = 2.0 Hz), 8.19(1H, s). |
| 1-100 | ¹H NMR (500 MHz, CDCl₃): δ ppm = 1.21(3H, t, J = 7.5 Hz), 2.23(3H, s), 2.64(3H, s), 3.45(3H, s), 7.03(1H, d, J = 3.0 Hz), 7.12(1H, dd, J = 2.5 Hz, J = 8.5 Hz), 7.33(1H, d, J = 8.5 Hz), 7.94(1H, d, J = 1.5 Hz), 8.22(1H, s). |
| 1-130 | ¹H NMR (500 MHz, CDCl₃): δ ppm = 1.27-1.30(3H, m), 2.14-2.25(3H, m), 2.26-2.34(3H, m), 3.60-3.76(6H, m), 5.65-5.83(1H, m), 6.92-7.20(2H, m), 7.35-7.39(1H, m), 7.95(1H, br. s), 8.17-8.22(1H, m). |
| 1-131 | ¹H NMR (500 MHz, CDCl₃): δ ppm = 1.22-1.36(6H, m), 2.15-2.25(3H, m), 2.26-2.35(3H, m), 3.74-3.76(3H, m), 4.10-4.19(2H, m), 5.65-5.84(1H, m), 6.92-7.20(2H, m), 7.34-7.39(1H, m), 7.94(1H, br. s), 8.17-8.19(1H, m). |
| 1-132 | ¹H NMR (500 MHz, CDCl₃): δ ppm = 2.23(3H, s), 2.34(3H, s), 3.31(3H, s), 3.75(3H, s), 4.60(1H, d, J = 6.0 Hz), 4.71(1H, d, J = 6.5 Hz),7.01(1H, d, J = 2.5 Hz), 7.10(1H, dd, J = 2.5 Hz, J = 8.5 Hz), 7.33(1H, d, J = 8.5 Hz), 7.94(1H, d, J = 2.5 Hz), 8.20(1H, s). |
| 1-133 | ¹H NMR (500 MHz, CDCl₃): δ ppm = 1.22-1.29(9H, m), 2.15-2.24(3H, br. s), 2.26-2.36(3H, m), 3.74-3.76(6H, m), 4.71-4.83(1H, m), 5.64-5.86(1H, m), 6.92-7.20(2H, m), 7.35-7.39(1H, m), 7.94(1H, br. s), 8.17(1H, br. s). |
| 1-135 | ¹H NMR (500 MHz, CDCl₃): δ ppm = 0.81(3H, t, J = 7.5 Hz), 1.11-1.19(2H, m), 1.36-1.45(2H, m), 2.19(3H, s), 2.23(3H, s), 2.25-2.32(2H, m), 3.80(3H, s), 6.88(1H, d, J = 3.0 Hz), 7.10(1H, m), 7.31(1H, d, J = 8.5 Hz), 7.94(1H, d, J = 1.5 Hz), 8.19(1H, d, J = 1.0 Hz). |
| 1-136 | ¹H NMR (500 MHz, CDCl₃): δ ppm = 2.22(3H, s), 2.24-2.26 (6H, m), 3.81(3H, s), 3.83(3H, s), 6.91(1H, d, J = 3.0 Hz), 7.03 (1H, dd, J = 2.5 Hz, J = 8.5 Hz), 7.28(1H, d, J = 9.0 Hz), 7.74 (1H, s), 7.91-7.94(2H, m). |
| 1-137 | ¹H NMR (500 MHz, CDCl₃): δ ppm = 1.23(3H, t, J = 7.5 Hz), 2.04(3H, s), 2.20(3H, s), 2.56(2H, q, J = 7.5 Hz), 3.82(3H, s), 6.88(1H, d, J = 2.5 Hz), 7.09(1H, dd, J = 2.5 Hz, J = 8.0 Hz), 7.32(1H, d, J = 8.5 Hz), 7.94(1H, d, J = 2.5 Hz), 8.19(1H, s). |
| 1-138 | ¹H NMR (500 MHz, CDCl₃): δ ppm = 1.26(3H, m), 2.23(3H, s), 2.71(2H, m), 3.32(3H, s), 3.76(3H, s), 4.58(1H, d, J = 5.5 Hz) 4.69(1H, d, J = 6.0 Hz), 7.02(1H, s), 7.10(1H, dd, J = 2.5 Hz, J = 8.5 Hz), 7.33(1H, d, J = 8.511z), 7.94(1H, d, J = 2.5 Hz), 8.21(1H, s). |
| 1-139 | ¹H NMR (500 MHz, CDCl₃): δ ppm = 1.15-1.29(6H, m), 2.14-2.34(3H, m), 2.53-2.73(2H, m), 3.69-3.72(3H, m), 3.75-3.77(3H, m), 5.66-5.84(1H, m), 6.92-7.21(2H, m), 7.34-7.39(1H, m), 7.94-7.95(1H, m), 8.17-8.20(1H, m). |
| 1-140 | ¹H NMR (500 MHz, CDCl₃): δ ppm = 2.25(3H, s), 3.51(3H, s), 3.82(3H, s), 7.06(1H, d, J = 2.5 Hz), 7.18(1H, d, J = 8.5 Hz), 7.37(1H, d, J = 8.5 Hz), 7.96(1H, d, J = 2.0 Hz), 8.22(IH, s). |
| 1-141 | ¹H NMR (500 MHz, CDCl₃): δ ppm = 2.23(3H, s), 3.83(3H, s), 7.02(1H, d, J = 3.0 Hz), 7.17(1H, dd, J = 2.5 Hz, J = 8.5 Hz), 7.45(1H, d, J = 8.5 Hz), 7.99-8.00(2H, m), 8.17(1H, d, J = 1.5 Hz). |
| 1-142 | ¹H NMR (500 MHz, CDCl₃): δ ppm = 2.05(3H, s), 2.22(3H, s), 3.90(3H, s), 6.93(1H, d, J = 2.5 Hz), 7.13(1H, dd, J = 2.5 Hz, J = 8.5 Hz), 7.34(1H, d, J = 8.5 Hz), 7.96(1H, d, J = 2.0 Hz), 8.19(1H, s). |
| 1-147 | ¹H NMR (500 MHz, CDCl₃): δ ppm = 2.17(3H, s), 2.26(3H, s), 3.44(3H, s), 3.47(3H, s), 3.71(3H, s), 6.87(1H, d, J = 2.5 Hz), 6.99(1H, dd, J = 2.0 Hz, J = 8.0 Hz), 7.22(1H, d, J = 8.0 Hz), 7.66(1H, d, J = 2.0 Hz), 8.45(1H, s). |
| 1-148 | ¹H NMR (500 MHz, CDCl₃): δ ppm = 2.18(3H, s), 2.29(3H, s), 3.45(3H, s), 3.76(3H, s), 7.20(1H, br. s), 7.25-7.38(2H, m), 7.67-7.74(2H, m), 8.34(1H, d, J = 1.0 Hz). |
| 1-162 | ¹H NMR (300 MHz, CDCl₃): δ ppm = 3.74(3H, s), 7.19-7.26 (2H, m), 7.42(1H, dd, J = 1.2 Hz, J = 7.5 Hz), 7.72(1H, s), 8.00(1H, d, J = 2.1 Hz), 8.09(1H, dd, J = 1.2 Hz, J = 2.1 Hz). |
| 1-170 | ¹H NMR (300 MHz, CDCl₃): δ ppm - 0.55-0.58(4H, m), 1.33-1.41(1H, m), 2.10(3H, s), 2.22(3H, s), 4.03-4.16(2H, m), 6.94(1H, d, J = 2.7 Hz), 7.11(1H, dd, J = 2.1 Hz, J = 8.4 Hz), 7.34(1H, d, J = 8.4 Hz), 7.76(1H, s), 7.96(1H, d, J = 2.1 Hz), 8.22(1H, dd, J = 1.2 Hz, J = 2.1 Hz). |
| 1-171 | ¹H NMR (300 MHz, CDCl₃): δ ppm = 1.21(3H, t, J = 8.4 Hz), 2.15(3H, s), 2.40-2.60(2H, m), 3.82(3H, s), 6.88(1H, d, J = 2.7 Hz), 7.18(1H, dd, J = 2.1 Hz, J = 8.4 Hz), 7.40(1H, d, J = 8.4 Hz), 7.75(1H, s), 7.96(1H, d, J = 2.1 Hz), 8.23(1H, dd, J = 1.2 Hz, J= 2.1 Hz). |
| 1-176 | ¹H NMR (500 MHz, CDCl₃): δ ppm = 2.07(3H, s), 2.20(3H, s), 3.50(3H, s), 5.46-5.50(2H, m), 6.90(1H, s), 7.11(1H, dd, J = 2.1 Hz, J = 8.4 Hz), 7.32(1H, d, J = 8.4 Hz), 7.79(1H, s), 7.95(1H, s), 8.20(1H, s). |
| 1-181 | ¹H NMR (500 MHz, CDCl₃): δ ppm = 1.40(3H, t, J = 8.4 Hz), 2.09(3H, s), 2.20(3H, s), 4.20-4.32(2H, m), 6.91(1H, s), 7.12(1H, dd, J = 2.1 Hz, J = 8.4 Hz), 7.33(1H, d, J = 8.4 Hz), 7.75(1H, s), 7.95(1H, s), 8.20(1H, s). |
| 1-182 | ¹H NMR (500 MHz, CDCl₃): δ ppm = 2.07(3H, s), 2.20(3H, s), 3.37(3H, s), 3.78-3.81(2H, m), 4.38-4.45(2H, m), 6.90(1H, s), 7.11(1H, dd, J = 2.1 Hz, J = 8.4 Hz), 7.34(1H, d, J = 8.4 Hz), 7.77(1H, s), 7.95(1H, s). |
| 1-185 | ¹H NMR (500 MHz, CDCl₃): δ ppm = 2.18(3H, s), 3.76(3H, s), 3.88(3H, s), 4.83-4.95(2H, m), 7.01(1H, s), 7.11(1H, d, J = 8.0 Hz), 7.31(1H, d, J = 8.0 Hz), 7.91(1H, s), 7.95(1H, s), 8.25(1H, s). |
| 1-187 | ¹H NMR (500 MHz, CDCl₃): δ ppm = 2.10(3H, s), 2.21(3H, s), 2.30(3H, s), 5.20(1H, d, J = 13.0 Hz), 5.27(1H, d, J = 13.0 Hz), 6.90(1H, s), 7.11(1H, d, J = 8.0 Hz), 7.33(1H, d, J = 8.0 Hz), 7.78(1H, s), 7.96(1H, s), 8.20(1H, s). |
| 2-5 | ¹H NMR (500 MHz, CDCl₃): δ ppm = 2.22(3H, s), 2.32(3H, s), 3.75(3H, s), 6.59(1H, br. s), 7.02(1H, d, J = 2.5 Hz), 7.17(1H, dd, J = 2.5 Hz, J = 8.0 Hz), 7.43(1H, d, J = 8.5 Hz), 7.69(1H, d, J = 8.5 Hz), 8.12(1H, s). |
| 2-8 | ¹H NMR (500 MHz, CDCl₃): δ ppm = 2.22(3H, s), 2.32(3H, s), 3.74(3H, s), 7.17(1H, br. s), 7.22-7.24(2H, m), 7.31-7.34(1H, m,) 7.42-7.45(2H, m). |
| 2-10 | ¹H NMR (500 MHz, CDCl₃): δ ppm = 2.21(3H, s), 2.31(3H, s), 3.73(3H, s), 7.17(1H, d, J = 3.0 Hz), 7.25-7.26(2H, m), 7.30-7.33(1H, m) 7.40(1H, d, J = 8.0 Hz), 7.50(1H, d, J = 8.5 Hz), 7.64(1H, d, J = 1.0 Hz). |
| 2-11 | ¹H NMR (500 MHz, CDCl₃): δ ppm = 2.18(3H, s), 2.32(3H, s), 3.74(3H, s), 5.54(1H, br. s), 6.90(1H, d, J = 2.5 Hz), 7.04-7.08(2H, m), 7.36-7.40(2H, m), 7.45(1H, dd, J = 2.0 Hz, J = 10.0 Hz). |
| 2-13 | ¹H NMR (500 MHz, CDCl₃): δ ppm = 2.17(3H, s), 2.31(3H, s), 3.72(3H, s), 5.73(1H, br. s), 6.86(1H, d, J = 3.0 Hz), 7.00-7.04(2H, m), 7.36(1H, d, J = 8.0 Hz), 7.40-7.44(1H, m), 7.69(1H, d, J = 2.5 Hz). |
| 2-14 | ¹H NMR (500 MHz, CDCl₃): δ ppm = 2.20(3H, s), 2.30(3H, s), 3.74(3H, s), 6.97(1H, s), 7.11(1H, dd, J = 2.5 Hz, J = 8.5 Hz), 7.18(1H, br. s), 7.39(1H, d, J = 8.5 Hz), 7.52(1H, dd, J = 1.5 Hz, J = 9.0 Hz), 7.78(1H, s). |
| 2-61 | ¹H NMR (500 MHz, CDCl₃): δ ppm = 2.06(3H, s), 2.19(3H, 5), 2.24(3H, s), 3.80(3H, s), 6.86(1H, d, J = 3.0 Hz), 6.98(1H, d, J = 8.5 Hz), 7.08(1H, dd, J = 2.5 Hz, J = 8.5 Hz), 7.31(1H, d, J = 8.0 Hz), 7.86(1H, dd, J = 2.5 Hz, J = 8.5 Hz), 8.38(1H, s). |
| 2-86 | ¹H NMR (500 MHz, CDCl₃): δ ppm = 2.23(3H, s), 2.32(3H, s), 3.76(3H, s), 6.59(1H, br. s), 7.03(1H, d, J = 2.5 Hz), 7.16-7.20(1H, m,) 7.44(1H, d, J = 8.5 Hz), 8.23(1H, d, J = 2.0 Hz), 8.39(1H, d, J = 2.0 Hz), 9.94(1H, s). |
| 2-88 | ¹H NMR (500 MHz, CDCl₃): δ ppm = 2.16(3H, s), 2.31(3H, s), 3.73(3H, s), 5.76(1H, br. s), 6.87(1H, d, J = 3.0 Hz), 7.01-7.06(3H, m), 7.35(1H, d, J = 9.0 Hz), 7.53-7.55(2H, m). |
| 2-89 | ¹H NMR (500 MHz, CDCl₃): δ ppm = 1.25(3H, t, J = 7.5 Hz), 2.23(3H, s), 2.69(2H, q, J = 7.5 Hz), 3.75(3H, s), 7.21-7.24(2H, m), 7.30-7.33(2H, m), 7.43-7.45(2H, m). |
| 2-91 | ¹H NMR (500 MHz, CDCl₃): δ ppm = 2.21(3H, s), 2.31(3H, s), 3.74(3H, s), 6.57(1H, br. s), 7.01(1H, d, J = 2.5 Hz), 7.15(1H, dd, J = 2.5 Hz, J = 8.0 Hz), 7.40(1H, d, J = 8.0 Hz), 8.46(2H, s). |
| 2-100 | ¹H NMR (500 MHz, CDCl₃): δ ppm = 2.17(3H, s), 2.29(3H, s), 3.70(3H, s), 6.19(1H, br. s), 6.98(1H, d, J = 3.0 Hz), 7.05-7.07(1H, m), 7.38(1H, d, J = 8.0 Hz), 7.87(1H, s), 8.41(1H, s). |
| 2-103 | ¹H NMR (500 MHz, CDCl₃): δ ppm = 2.24(3H, s), 2.30(3H, s), 3.74(3H, s), 7.04(1H, d, J = 2.0 Hz), 7.13(1H, d, J = 8.0 Hz), 7.42-7.44(2H, m), 7.84(1H, d, J = 9.5 Hz). |
| 2-104 | ¹H NMR (500 MHz, CDCl₃): δ ppm = 2.28(3H, s), 2.31(3H, s), 3.74(3H, s), 7.19(1H, d, J = 3.0 Hz), 7.23-7.28(3H, m), 7.35-7.39(1H, m), 7.41-7.44(2H, m). |

TABLE 4-continued

| No. | 1H-NMR δ ppm (Solvent: CDCl$_3$) |
|---|---|
| 2-105 | $^1$H NMR (500 MHz, CDCl$_3$): δ ppm = 2.22(3H, s), 2.31(3H, s), 3.74(3H, s), 7.18-7.22(2H, m), 7.25-7.30(1H, m), 7.33-7.37(2H, m), 7.42(1H, d, J = 8.5 Hz), 7.98(1H, br. s). |
| 2-112 | $^1$H NMR (500 MHz, CDCl$_3$): δ ppm = 2.05(3H, s), 2.38(3H, s), 3.74(3H, s), 6.76(1H, dd, J = 2.5 Hz, J = 8.5 Hz), 6.94(1H, d, J = 8.5 Hz), 7.00 (1H, d, J = 3.0 Hz), 7.51-7.54(1H, m), 7.61-7.64(1H, m), 7.66-7.69(2H, m), 8.01(1H, d, J = 8.0 Hz), 8.22(1H, d, J = 3.0 Hz). |
| 2-115 | $^1$H NMR (500 MHz, CDCl$_3$): δ ppm = 2.06(3H, s), 2.20(3H, s), 2.24(3H, s), 3.80(3H, s), 6.87(1H, d, J = 2.5 Hz), 7.09(1H, dd, J = 2.5 Hz, J = 8.5 Hz), 7.32(1H, d, J = 8.5 Hz), 8.11(1H, d, J = 2.0 Hz), 8.23(1H, s). |
| 2-116 | $^1$H NMR (500 MHz, CDCl$_3$): δ ppm = 2.05(3H, s), 2.20(3H, s), 2.25(3H, s), 3.80(3H, s), 6.89(1H, d, J = 3.0 Hz), 7.10(1H, dd, J = 2.5 Hz, J = 8.5 Hz), 7.33(1H, d, J = 8.5 Hz), 8.17(1H, d, J = 1.5 Hz), 8.47(1H, s). |
| 2-117 | $^1$H NMR (500 MHz, CDCl$_3$): δ ppm = 1.98(3H, s), 2.18(3H, s), 2.24(3H, s), 3.80(3H, s), 6.89(1H, d, J = 2.5 Hz), 7.10(1H, dd, J = 2.5 Hz, J = 8.5 Hz), 7.28-7.32(2H, m), 7.87(1H, d, J = 8.0 Hz). |
| 2-118 | $^1$H NMR (500 MHz, CDCl$_3$): δ ppm = 2.03(3H, s), 2.17(3H, s), 2.37(3H, s), 3.80(3H, s), 6.79(1H, d, J = 2.5 Hz), 6.98-7.05(3H, m), 7.25-7.30(1H, m), 7.52-7.55(2H, m). |
| 2-120 | $^1$H NMR (500 MHz, CDCl$_3$): δ ppm = 2.02(3H, s), 2.17(3H, s), 2.24(3H, s), 3.80(3H, s), 6.76(1H, d, J = 2.5 Hz), 6.96-7.02(2H, m), 7.29(1H, d, J = 8.5 Hz), 7.35(1H, d, J = 8.5 Hz), 7.44(1H, dd, J = 2.0 Hz, J = 10.0 Hz). |
| 2-125 | $^1$H NMR (500 MHz, CDCl$_3$): δ ppm = 2.05(3H, s), 2.19(3H, s), 2.24(3H, s), 3.80(3H, s), 6.85(1H, d, J = 2.5 Hz), 7.08(1H, dd, J = 2.5 Hz, J = 8.0 Hz), 7.30(1H, d, J = 8.0 Hz), 7.93(1H, d, J = 3.0 Hz), 8.15(1H, d, J = 3.0 Hz). |
| 2-126 | $^1$H NMR (500 MHz, CDCl$_3$): δ ppm = 2.05(3H, s), 2.20(3H, s), 2.25(3H, s), 3.81(3H, s), 6.87(1H, d, J = 3.0 Hz), 7.08(1H, dd, J = 2.5 Hz, J = 8.0 Hz), 7.32-7.34(2H, m), 8.53(1H, s). |
| 2-129 | $^1$H NMR (500 MHz, CDCl$_3$): δ ppm = 2.07(3H, s), 2.17(3H, s), 2.24(3H, s), 2.29(3H, s), 3.80(3H, s), 6.78(1H, d, J = 2.5 Hz), 7.03(1H, dd, J = 2.0 Hz, J = 8.5 Hz), 7.27(1H, d, J = 8.0 Hz), 7.60(1H, d, J = 2.0 Hz), 7.92(1H, d, J = 2.0 Hz). |
| 2-133 | $^1$H NMR (500 MHz, CDCl$_3$): δ ppm = 2.06(3H, s), 2.21(3H, s), 2.25(3H, s), 3.81(3H, s), 6.89(1H, d, J = 2.5 Hz), 7.10(1H, dd, J = 2.0 Hz, J = 8.5 Hz), 7.34(1H, d, J = 8.5 Hz), 8.54(1H, d, J = 2.5 Hz), 8.81(1H, d, J = 2.5 Hz). |
| 2-134 | $^1$H NMR (500 MHz, CDCl$_3$): δ ppm = 2.04(3H, s), 2.20(3H, s), 2.27(3H, s), 3.80(3H, s), 6.83(1H, d, J = 2.5 Hz), 7.07(1H, dd, J = 2.5 Hz, J = 8.0 Hz), 7.35(1H, d, J = 8.0 Hz), 7.90(1H, s), 8.35(1H, s). |
| 2-135 | $^1$H NMR (500 MHz, CDCl$_3$): δ ppm = 2.05(3H, s), 2.17(3H, s), 2.24(3H, s), 3.80(3H, s), 6.84(1H, d, J = 2.0 Hz), 7.07(1H, dd, J = 2.0 Hz, J = 8.0 Hz), 7.29(1H, d, J = 8.0 Hz), 7.86(1H, d, J = 2.5 Hz), 7.98(1H, d, J = 2.5 Hz). |
| 2-149 | $^1$H NMR (500 MHz, CDCl$_3$): δ ppm = 2.24(3H, s), 2.34(3H, s), 3.31(1H, s), 3.47(3H, s), 3.74(3H, s), 4.58-4.61(1H, m), 4.70-4.73(1H, m), 5.17(2H, s), 6.99-7.03(1H, m), 7.10-7.15(1H, m), 7.30-7.36(1H, m), 7.94(1H, s), 8.08(1H, s), 8.15(1H, m). |
| 2-160 | $^1$H NMR (300 MHz, CDCl$_3$): δ ppm = 1.21(3H, t, J = 8.4 Hz), 2.16(3H, s), 2.62-2.39(2H, m), 3.85(3H, s), 7.11(1H, s), 7.23-7.27(1H, m), 7.35-7.44(4H, m), 7.77(1H, s). |
| 2-164 | $^1$H NMR (300 MHz, CDCl$_3$): δ ppm = 2.13(3H, s), 2.26(3H, s), 3.85(3H, s), 7.15(1H, s), 7.22-7.26 (1H, m), 7.26-7.37(3H, m), 7.44(1H, d, J = 2.1 Hz), 7.77(1H, s). |
| 2-172 | $^1$H NMR (300 MHz, CDCl$_3$): δ ppm = 1.39-1.43(6H, m), 2.08(3H, s), 2.20(3H, s), 5.32(1H, q, J = 6.6 Hz), 7.15(1H, s), 7.22-7.37(4H, m), 7.41(1H, d, J = 2.1 Hz), 7.82(1H, s). |
| 2-190 | $^1$H NMR (300 MHz, CDCl$_3$): δ ppm = 1.15-1.28(9H, m), 2.06(3H, s), 2.24(3H, s), 2.38-2.60(2H, m), 3.36-3.50(4H, m), 3.81(3H, s), 6.84(1H, d, J = 2.7 Hz), 7.17(1H, dd, J = 2.7 Hz, J = 8.7 Hz), 7.38(1H, d, J = 8.7 Hz), 7.81(1H, d, J = 1.8 Hz), 8.01(1H, d, J = 2.4 Hz). |
| 2-193 | $^1$H NMR (300 MHz, CDCl$_3$): δ ppm = 2.21(3H, s), 2.32(3H, s), 3.73(3H, s), 6.88(1H, d, J = 10.0 Hz), 7.01(1H, d, J = 2.5 Hz), 7.12(1H, dd, J = 2.3 Hz, J = 8.3 Hz), 7.36(1H, d, J = 8.5 Hz), 7.54(1H, d, J = 10.0 Hz). |
| 2-194 | $^1$H NMR (500 MHz, CDCl$_3$): δ ppm = 2.23(3H, s), 2.32(3H, s), 3.75(3H, s), 6.42(1H, brs), 7.02(1H, d, J = 3.0 Hz), 7.15(1H, dd, J = 2.3 Hz, 1 = 8.3 Hz), 7.44(1H, d, J = 7.0 Hz), 8.37(1H, d, J = 8.5 Hz), 8.53(1H, s). |
| 2-195 | $^1$H NMR (500 MHz, CDCl$_3$): δ ppm = 2.05(311, s), 2.20(3H, s), 2.20(3H, s), 3.81(3H, s), 6.89(1H, d, J = 2.5 Hz), 7.10(1H, dd, J = 2.3 Hz, J = 7.5 Hz), 7.34(1H, d, J = 8.0 Hz), 8.38(1H, s), 8.46(1H, s). |
| 2-198 | $^1$H NMR (500 MHz, CDCl$_3$): δ ppm 2.25(3H, s), 2.32(3H, s), 3.76(3H, s), 6.26(1H, brs), 7.13(1H, d, J = 3.0 Hz), 7.46(1H, d, J = 8.5 Hz), 8.3(1H, d, J = 8.3 Hz), 7.70(1H, d, J = 8.5 Hz), 8.05(1H, d, J = 8.0 Hz), 9.40(1H, s). |
| 3-27 | $^1$H NMR (500 MHz, CDCl$_3$): δ ppm = 2.26(6H, br. s), 3.55(3H, s), 3.76(3H, s), 7.10(1H, d, J = 2.5 Hz), 7.18-7.21 (1H, m), 7.35-7.37(1H, m), 7.58-7.59(2H, m), 8.04(1H, s), 8.68(1H, s). |
| 3-35 | $^1$H NMR (500 MHz, CDCl$_3$): δ ppm = 1.14(3H, t, J = 7.5 Hz), 2.23(3H, s), 2.36(3H, s), 3.82(3H, s), 4.11(2H, m), 7.06(1H, d, J = 2.5 Hz), 7.22(1H, dd, J = 2.5 Hz, J = 8.5 Hz), 7.34(1H, d, J = 8.0 Hz), 7.60(1H, dd, J = 2.0 Hz, J = 8.5 Hz), 7.73(1H, d, J = 9.5 Hz), 8.03(1H, d, J = 2.5 Hz), 8.65(1H, s). |
| 3-37 | $^1$H NMR (500 MHz, CDCl$_3$): δ ppm = 0.78-0.92(4H, m), 1.59-1.63(1H, m), 2.21(3H, s), 2.25(3H, s), 3.80(3H, s), 7.00(1H, d, J = 3.0 Hz), 7.21(1H, dd, J = 2.5 Hz, J = 8.5 Hz), 7.34(1H, d, J = 8.5 Hz), 7.59(1H, dd, J = 2.0 Hz, J = 9.5 Hz), 7.70(1H, d, J = 8.5 Hz), 8.03(1H, d, J = 2.5 Hz), 8.65(1H, s). |
| 3-39 | $^1$H NMR (500 MHz, CDCl$_3$): δ ppm = 2.22(3H, s), 2.30(3H, s), 3.31-3.46(4H, m), 3.81(3H, s), 7.06(1H, br. s), 7.23-7.25(1H, m), 7.34(1H, d, J = 8.5 Hz), 7.60(1H, dd, J = 2.0 Hz, J = 9.0 Hz), 7.72(1H, d, J = 9.0 Hz), 8.04(1H, d, J = 2.0 Hz), 8.65(1H, s). |
| 3-40 | $^1$H NMR (500 MHz, CDCl$_3$): δ ppm = 2.26(3H, s), 2.34(3H, s), 3.34(3H, s), 3.75(3H, s), 4.63(1H, d, J = 5.5 Hz), 4.85(1H, d, J = 5.5 Hz), 7.09(1H, d, J = 2.5 Hz), 7.18(1H, dd, J = 2.0 Hz, J = 8.0 Hz), 7.36(1H, d, J = 8.5 Hz), 7.57-7.63(2H, m), 8.03(1H, d, J = 2.0 Hz), 8.68(1H, s). |
| 3-43 | $^1$H NMR (500 MHz, CDCl$_3$): δ ppm = 2.24(3H, s), 2.26(3H, s), 2.27(3H, s), 3.75(3H, s), 3.83(3H, s), 7.04(1H, d, J = 2.0 Hz), 7.12(1H, dd, J = 2.5 Hz, J = 8.5 Hz), 7.29(1H, d, J = 8.5 Hz), 7.52(1H, d, J = 9.0 Hz), 7.56-7.59(1H, m), 7.74(1H, s), 8.02(1H, d, J = 2.5 Hz), 8.58(1H, s). |
| 3-44 | $^1$H NMR (500 MHz, CDCl$_3$): δ ppm = 1.09-1.31(3H, m), 2.17-2.25(3H, m), 2.26-2.37(3H, m), 3.66-3.77(6H, m), 5.67-5.93(1H, m), 7.02-7.31(2H, m), 7.36-7.42(1H, m), 7.54-7.59(2H, m), 8.04(1H, d, J = 1.0 Hz), 8.68(1H, s). |
| 3-46 | $^1$H NMR (500 MHz, CDCl$_3$): δ ppm = 2.21(3H, s), 2.26(3H, s), 2.38-2.49(2H, m), 2.60(2H, br.t, J = 6.5 Hz), 3.62(3H, s), 3.81(3H, s), 6.98(1H, d, J = 3.0 Hz), 7.18-7.21(1H, m), 7.34(1H, d, J = 8.5 Hz), 7.59(1H, d, J = 9.0 Hz), 7.66(1H, d, J = 9.0 Hz), 8.04(1H, d, J = 2.5 Hz), 8.67(1H, s). |
| 3-47 | $^1$H NMR (500 MHz, CDCl$_3$): δ ppm = 2.13(6H, s), 3.58(1H, d, J = 15.0 Hz), 3.64(1H, d, J = 15.0 Hz), 3.79(3H, s), 6.99-7.01(3H, m), 7.19-7.30(5H, m), 7.49-7.55(2H, m), 8.03(1H, d, J = 1.5 Hz), 8.67(1H, s). |
| 3-48 | $^1$H NMR (500 MHz, CDCl$_3$): δ ppm = 2.20(3H, s), 2.24(3H, s), 3.82(3H, s), 4.64(2H, s), 6.57-6.59(2H, m), 6.96(1H, t, J = 8.0 Hz), 7.04(1H, d, J = 2.0 Hz), 7.18-7.25(3H, m), 7.39(1H, d, J = 8.0 Hz), 7.44-7.48(2H, m), 8.01(1H, d, J = 1.5 Hz), 8.68(1H, s). |
| 3-49 | $^1$H NMR (500 MHz, CDCl$_3$): δ ppm = 2.23(3H, s), 2.24(3H, s), 3.82(3H, s), 5.90(1H, d, J = 11.0 Hz), 6.06(1H, dd, J = 11.0 Hz, J = 17.0 Hz), 6.40(1H, d, J = 17.0 Hz), 7.00(1H, d, J = 2.5 Hz), 7.18(1H, dd, J = 2.5 Hz, J = 8.0 Hz), 7.32(1H, d, J = 8.5 Hz), 7.59(1H, dd, J = 2.5 Hz, J = 9.0 Hz), 7.68(1H, d, J = 9.0 Hz), 8.03(1H, d, J = 1.5 Hz), 8.63(1H, s). |
| 3-52 | $^1$H NMR (500 MHz, CDCl$_3$): δ ppm = 2.22(3H, s), 2.29(3H, s), 3.85(3H, s), 7.00(1H, d, J = 2.0 Hz), 7.23(1H, dd, J = 2.5 Hz, J = 8.0 Hz), 7.36(1H, d, J = 8.5 Hz), 7.60(1H, dd, J = 2.0 Hz, J = 9.0 Hz), 7.67(1H, d, J = 9.0 Hz), 8.03(1H. d, J = 2.5 Hz), 8.67(1H, s). |
| 3-54 | $^1$H NMR (500 MHz, CDCl$_3$): δ ppm = 2.23(3H, s), 2.26(3H, s), 3.82(3H, s), 6.15(1H, d, J = 9.0 Hz), 6.75(1H, d, J = 9.0 Hz), 7.01(1H, d, J = 2.0 Hz), 7.19(1H, dd, J = 2.5 Hz, J = 8.5 Hz), 7.33(1H, d, J = 8.5 Hz), 7.59(1H, dd, J = 2.5 Hz, J = 9.0 Hz), 7.68(1H, d, J = 9.0 Hz), 8.03(1H, d, J = 2.0 Hz), 8.64(1H, s). |
| 3-55 | $^1$H NMR (500 MHz, CDCl$_3$): δ ppm = 2.22(3H, s), 2.30(3H, s), 3.27(3H, s), 3.43-3.47(2H, m), 3.81(3H, s), 4.18-4.22(2H, m), 7.07(1H, d, J = 2.5 Hz), 7.23(1H, d, J = 2.5 Hz, J = 8.5 Hz), 7.34(1H, d, J = 8.5 Hz), 7.60(1H, dd, J = 2.0 Hz, J = 9.0 Hz), 7.74(1H, d, J = 8.5 Hz), 8.03(1H, d, J = 2.0 Hz), 8.65(1H, s). |
| 3-56 | $^1$H NMR (500 MHz, CDCl$_3$): δ ppm = 0.84(3H, t, J = 7.5 Hz), 1.44-1.51(2H, m), 2.22(3H, s), 2.28(3H, s), 2.66-2.75(2H, m), |

TABLE 4-continued

| No. | 1H-NMR δ ppm (Solvent: CDCl₃) |
|---|---|
|  | 3.81(3H, s), 7.04(1H, d, J = 2.5 Hz), 7.22(1H, dd, J = 2.5 Hz, J = 8.5 Hz), 7.33(1H, d, J = 8.5 Hz), 7.59(1H, dd, J = 2.0 Hz, J = 8.5 Hz), 7.74(1H, d, J = 9.0 Hz), 8.03(1H, d, J = 2.0 Hz), 8.65(1H, s). |
| 3-57 | ¹H NMR (500 MHz, CDCl₃): δ ppm = 2.24(3H, s), 2.38(3H, s), 3.83(3H, s), 6.81-6.84(2H, m), 6.89-6.99(2H, m), 7.13(1H, d, J = 2.5 Hz), 7.28(1H, dd, J = 2.5 Hz, J = 8.5 Hz), 7.39(1H, d, J = 8.5 Hz), 7.48(2H, br. s), 8.02(1H, s), 8.67(1H, s). |
| 3-58 | ¹H NMR (500 MHz, CDCl₃): δ ppm = 2.22(3H, s), 2.30(3H, s), 3.81(3H, s), 4.49-4.56(2H, m), 5.15-5.18(2H, m), 5.67-5.76(1H, m), 7.06(1H, d, J = 2.5 Hz), 7.23(1H, dd, J = 2.5 Hz, J = 8.5 Hz), 7.34(1H, d, J = 8.0 Hz), 7.59(1H, d, J = 9.0 Hz), 7.72(1H, d, J = 8.5 Hz), 8.03(1H, d, J = 2.5 Hz), 8.65(1H, s). |
| 3-59 | ¹H NMR (500 MHz, CDCl₃): δ ppm = 2.23(3H, s), 2.32(3H, s), 3.46-3.52(2H, m), 3.82(3H, s), 4.28(2H, t, J = 5.5 Hz), 7.07(1H, d, J = 2.5 Hz), 7.23-7.25(1H, m), 7.35(1H, d, J = 8.5 Hz), 7.60(1H, dd, J = 2.0 Hz, J = 9.0 Hz), 7.73(1H, d, J = 8.5 Hz), 8.04(1H, d, J = 2.0 Hz), 8.65(1H, s). |
| 3-60 | ¹H NMR (500 MHz, CDCl₃): δ ppm = 1.11(3H, d, J = 6.0 Hz), 1.14(3H, d, J = 6.5 Hz), 2.23(3H, s), 2.31(3H, s), 3.81(3H, s), 4.70-4.78(1H, m), 7.07(1H, d, J = 2.0 Hz), 7.22(1H, dd, J = 3.0 Hz, J = 8.0 Hz), 7.33(1H, d, J = 8.5 Hz), 7.59(1H, dd, J = 2.0 Hz, J = 8.5 Hz), 7.73(1H, d, J = 8.5 Hz), 8.03(1H, d, J = 2.0 Hz), 8.64(1H, s). |
| 3-61 | ¹H NMR (500 MHz, CDCl₃): δ ppm = 0.59-0.98(13H, m), 1.23-1.39(2H, m), 1.51-1.86(3H, m), 2.22-2.23(3H, m), 2.30(3H, s), 3.82(3H, s), 4.37-4.45(1H, m), 7.07-7.11(1H, m), 7.20-7.25(1H, m), 7.32(1H, d, J = 8.0 Hz), 7.57-7.61(1H, m), 7.75(1H, d, J = 9.0 Hz), 8.03(1H, d, J = 2.5 Hz), 8.64(1H, s). |
| 3-62 | ¹H NMR (500 MHz, CDCl₃): δ ppm = 2.25(3H, s), 2.30(3H, s), 3.84(3H, s), 6.83-6.85(2H, m), 7.15(1H, d, J = 2.0 Hz), 7.23-7.30(4H, m), 7.38(1H, d, J = 8.5 Hz), 7.47(1H, dd, J = 2.5 Hz, J = 8.5 Hz), 7.53(1H, d, J = 8.5 Hz), 8.02(1H, d, J = 2.5 Hz), 8.68(1H, s). |
| 3-63 | ¹H NMR (500 MHz, CDCl₃): δ ppm = 2.04(3H, s), 2.24(3H, s), 3.80(3H, s), 6.96(1H, br. s), 7.26-7.38(6H, m), 7.40-7.44(1H, m), 7.54(1H, dd, J = 2.5 Hz, J = 9.0 Hz), 7.66(1H, d, J = 9.0 Hz), 8.04(1H, d, J = 2.5 Hz), 8.70(1H, s). |
| 3-64 | ¹H NMR (500 MHz, CDCl₃): δ ppm = 2.23(3H, s), 2.31(3H, s), 2.50(1H, t, J = 2.5 Hz), 3.82(3H, s), 4.57-4.64(2H, m), 7.05(1H, d, J = 3.0 Hz), 7.22(1H, d, J = 8.0 Hz), 7.34(1H, d, J = 8.5 Hz), 7.60(1H, dd, J = 2.5 Hz, J = 8.5 Hz), 7.74(1H, d, J = 9.0 Hz), 8.03(1H, d, J = 2.5 Hz), 8.65(1H, s). |
| 3-65 | ¹H NMR (500 MHz, CDCl₃): δ ppm = 2.23(3H, s), 2.28(3H, s), 2.76(3H, s), 2.77(3H, s), 3.80(3H, s), 7.05(1H, d, J = 2.0 Hz), 7.20(1H, dd, J = 2.5 Hz, J = 8.5 Hz), 7.33(1H, d, J = 8.5 Hz), 7.60(1H, dd, J = 2.5 Hz, 1 = 9.0 Hz), 7.68(1H, d, J = 9.0 Hz), 8.04(1H, d, J = 2.5 Hz), 8.64(1H, s). |
| 3-67 | ¹H NMR (500 MHz, CDCl₃): δ ppm = 2.20-2.33(6H, m), 2.97-3.03(3H, m), 3.13-3.24(3H, m), 3.81-3.83(3H, m), 6.96-7.33(3H, m), 7.58-7.73(2H, m), 8.04-8.05(1H, m), 8.64-8.65(1H, m). |
| 3-71 | ¹H NMR (500 MHz, CDCl₃): δ ppm = 1.98(3H, s), 2.40(3H, s), 2.53(3H, s), 3.78(3H, s), 6.98(1H, d, J = 8.0 Hz), 7.06-7.12(4H, m), 7.50-7.52(2H, m), 7.58(1H, dd, J = 2.0 Hz, J = 8.5 Hz), 7.69(1H, d, J = 9.0 Hz), 8.05(1H, d, J = 2.0 Hz), 8.66(1H, s). |
| 3-75 | ¹H NMR (500 MHz, CDCl₃): δ ppm = 2.26(3H, s), 2.33(3H, s), 3.33(3H, s), 3.47(2H, t, J = 4.0 Hz), 3.60-3.67(2H, m), 3.75(3H, s), 4.72(1H, d, J = 6.0 Hz), 4.93(1H, d, J = 6.0 Hz), 7.09(1H, br. s), 7.17-7.19(1H, m), 7.35(1H, d, J = 8.5 Hz), 7.56-7.59(1H, m), 7.66(1H, d, J = 9.0 Hz), 8.03(1H, d, J = 2.5 Hz), 8.67(1H, s). |
| 3-76 | ¹H NMR (500 MHz, CDCl₃): δ ppm = 1.17-1.55(9H, m), 1.67-1.91(4H, m), 2.16-2.23(3H, m), 2.25-2.38(3H, m), 3.74-3.76(3H, m), 4.39-4.57(1H, m), 5.67-5.96(1H, m), 7.01-7.25(2H, m), 7.31-7.41(1H, m), 7.53-7.58(2H, in), 8.03-8.04(1H, m), 8.67-8.68(1H, m). |
| 3-79 | ¹H NMR (500 MHz, CDCl₃): δ ppm = 1.27(3H, t, J = 7.0 Hz), 2.24(3H, s), 2.29(3H, s), 3.83(3H, s), 4.22-4.34(2H, m), 7.05(1H, d, J = 2.5 Hz), 7.22(1H, dd, J = 2.0 Hz, J = 9.0 Hz), 7.34(1H, d, J = 8.5 Hz), 7.60(1H, dd, J = 2.0 Hz, J = 8.5 Hz), 7.75(1H, d, J = 8.5 Hz), 8.03(1H, d, J = 2.0 Hz), 8.65(1H, s). |
| 3-80 | ¹H NMR (500 MHz, CDCl₃): δ ppm = 0.70-0.82(2H, m), 0.97-1.17(4H, m), 1.38-1.41(2H, m), 1.52-1.58(3H, m), 2.19(2H, dd, J = 2.0 Hz, J = 6.5 Hz), 2.21(3H, s), 2.23(3H, s), 3.80(3H, s), 7.03(1H, d, J = 2.5 Hz), 7.21(1H, dd, J = 2.0 Hz, J = 9.0 Hz), 7.32(1H, d, J = 8.0 Hz), 7.60(1H, dd, J = 2.0 Hz, J = 8.5 Hz), 7.70(1H, d, J = 9.0 Hz), 8.03(1H, d, J = 2.5 Hz), 8.65(1H, s). |
| 3-81 | ¹H NMR (500 MHz, CDCl₃): δ ppm = 2.26(3H, s), 2.33(3H, s), 3.52-3.59(2H, m), 3.73(2H, t, J = 6.0 Hz), 3.75(3H, s), 4.73(1H, d, J = 6.0 Hz), 4.96(1H, d, J = 6.0 Hz), 7.10(1H, d, J = 2.5 Hz), 7.20(1H, dd, J = 2.5 Hz, J = 8.5 Hz), 7.37(1H, d, J = 8.5 Hz), 7.59(1H, d, J = 2.5 Hz, J = 9.0 Hz), 7.65(1H, d, J = 9.0 Hz), 8.04(1H, d, J = 2.0 Hz), 8.68(1H, s). |
| 3-82 | ¹H NMR (500 MHz, CDCl₃): δ ppm = 2.22(3H, s), 2.28(3H, s), 3.00(1H, s), 3.82(3H, s), 7.02(1H, d, J = 2.5 Hz), 7.23(1H, dd, J = 2.5 Hz, J = 8.5 Hz), 7.36(1H, d, J = 8.5 Hz), 7.59(1H, dd, J = 2.5 Hz, J = 8.5 Hz), 7.74(1H, d, J = 9.0 Hz), 8.03(1H, d, J = 2.5 Hz), 8.66(1H, s). |
| 3-87 | ¹H NMR (500 MHz, CDCl₃): δ ppm = 1.69-1.73(3H, m), 2.22-2.23(3H, m), 2.31-2.32(3H, m), 3.82-3.83(3H, m), 6.18-6.25(1H, m), 7.04-7.06(1H, m), 7.21-7.24(1H, m), 7.33-7.36(1H, m), 7.59-7.62(1H, m), 7.72-7.76(1H, m), 8.03-8.04(1H, m), 8.64-8.54(1H, m). |
| 3-90 | ¹H NMR (500 MHz, CDCl₃): δ ppm = 2.22(3H, s), 2.28(3H, s), 3.48-3.56(2H, m), 3.81(3H, s), 4.18-4.26(2H, m), 4.43(2H, s), 7.08(1H, d, J = 2.5 Hz), 7.18-7.33(7H, m), 7.55(1H, dd, J = 2.5 Hz, J = 9.5 Hz), 7.72(1H, d, J = 9.5 Hz), 8.02(1H, d, J = 2.0 Hz), 8.60(1H, s). |
| 3-98 | ¹H NMR (500 MHz, CDCl₃): δ ppm = 2.22(3H, s), 2.30(3H, s), 3.33(1H, m), 3.45-3.48(2H, m), 3.50-3.53(2H, m), 3.54-3.57(2H, m), 3.81(3H, s), 4.19-4.22(2H, m), 7.07(1H, d, J = 2.5 Hz), 7.21-7.24(1H, m), 7.34(1H, d, J = 8.0 Hz), 7.59-7.62(1H, m), 7.74(1H, d, J = 9.0 Hz), 8.03(1H, d, J = 2.5 Hz), 8.65(1H, s). |
| 3-99 | ¹H NMR (500 MHz, CDCl₃): δ ppm = 2.23(3H, s), 2.31(3H, s), 3.72(2H, t, J = 4.5 Hz), 3.81(3H, s), 4.00(1H, dd, J = 2.5 Hz, J = 7.0 Hz), 4.07-4.11(1H, m), 4.26-4.29(2H, in), 6.34(1H, dd, J = 7.0 Hz, J = 14.0 Hz), 7.07(1H, d, J = 2.0 Hz), 7.22(1H, dd, J = 2.0 Hz, J = 8.5 Hz), 7.34(1H, d, J = 9.0 Hz), 7.59(1H, dd, J = 2.0 Hz, J = 9.0 Hz), 7.73(1H, d, J = 9.5 Hz), 8.03(1H, d, J = 2.5 Hz), 8.65(1H, s). |
| 3-100 | ¹H NMR (500 MHz, CDCl₃): δ ppm = 2.01(3H, s), 2.23(3H, s), 2.32(3H, s), 2.47-2.59(2H, m), 3.82(3H, s), 4.20(2H, t, J = 7.0 Hz), 7.07(1H, d, J = 2.5 Hz), 7.23-7.25(1H, m), 7.34(1H, d, J = 8.5 Hz), 7.60(1H, dd, J = 2.0 Hz, J = 9.5 Hz), 7.74(1H, d, J = 9.0 Hz), 8.03(1H, d, J = 2.5 Hz), 8.65(1H, s). |
| 3-101 | ¹H NMR (500 MHz, CDCl₃): δ ppm = [−0.06]−[0.03](2H, m), 0.34-0.39(2H, m), 0.47-0.55(1H, m), 1.38(2H, q, J = 6.5 Hz), 2.23(3H, s), 2.30(3H, s), 3.80(3H, s), 4.10-4.15(2H, m), 7.07(1H, d, J = 2.5 Hz), 7.22(1H, d, J = 2.5 Hz, J = 8.5 Hz), 7.33(1H, d, J = 8.0 Hz), 7.59(1H, dd, J = 2.5 Hz, J = 9.0 Hz), 7.74(1H, d, J = 8.5 Hz), 8.03(1H, d, J = 2.5 Hz), 8.64(1H, s). |
| 3-102 | ¹H NMR (500 MHz, CDCl₃): δ ppm = 0.78(6H, d, J = 7.5 Hz), 1.77-1.85(1H, m), 2.23(3H, s), 2.30(3H, s), 3.81(3H, s), 3.84(2H, d, J = 6.0 Hz), 7.07(1H, d, J = 3.0 Hz), 7.21-7.24(1H, m), 7.33(1H, d, J = 8.5 Hz), 7.59(1H, dd, J = 2.5 Hz, J = 8.5 Hz), 7.73(1H, d, J = 8.5 Hz), 8.03(1H, d, J = 2.0 Hz), 8.64(1H, s). |
| 3-105 | ¹H NMR (500 MHz, CDCl₃): δ ppm = 2.27(3H, s), 2.29(3H, s), 3.84(3H, s), 7.04-7.06(1H, m), 7.08(1H, d, J = 2.5 Hz), 7.10-7.13(1H, m), 7.28(1H, d, J = 8.5 Hz), 7,49(1H, d, J = 9.0 Hz), 7.54(1H, d, J = 2.5 Hz), 7.55-7.58(1H, m), 7.77(1H, dd, J = 1.0 Hz, J = 4.0 Hz), 8.10(1H, d, J = 2.0 Hz), 8.58(1H, s). |
| 3-106 | ¹H NMR (500 MHz, CDCl₃): δ ppm = 2.27(3H, s), 2.29(3H, s), 3.86(3H, s), 7.07(1H, d, J = 2.5 Hz), 7.10(1H, d, J = 2.5 Hz, J = 8.5 Hz), 7.28(1H, d, J = 8.5 Hz), 7.29-7.33(1H, m), 7.45(1H, d, J = 9.5 Hz), 7.55(1H, dd, J = 2.0 Hz, J = 9.5 Hz), 8.01(1H, d, J = 2.0 Hz), 8.13-8.16(1H, m), 8.59(1H, s), 8.76(1H, dd, H = 1.5 Hz, J = 5.0 Hz), 9.11(1H, d, J = 2.0 Hz). |
| 3-108 | ¹H NMR (500 MHz, CDCl₃): δ ppm = 0.88(3H, t, J = 7.0 Hz), 1.28-1.33(2H, m), 1.48-1.53(2H, m), 2.22(3H, s), 2.25(3H, s), 3.35-3.49(6H, m), 3.82(3H, s), 4.16(2H, d, J = 2.5 Hz), 7.00(1H, d, J = 2.5 Hz), 7.19(1H, dd, J = 2.5 Hz, J = 9.0 Hz), 7.33(1H, d, J = 9.0 Hz), 7.60(1H, dd, J = 2.5 Hz, J = 9.0 Hz), 7.73(1H, d, J = 9.0 Hz), 8.04(1H, d, J = 2.5 Hz), 8.66(1H, s). |
| 3-110 | ¹H NMR (500 MHz, CDCl₃): δ ppm = 2.26(3H, s), 2.28(3H, s), 3.84(3H, s), 7.07(1H, d, J = 2.0 Hz), 7.11(1H, dd, J = 2.5 Hz, J = 8.5 Hz), 7.25-7.29(2H, m), 7.39-7.41(1H, m), 7.49(1H, d, J = 8.5 Hz), 7.55(1H, dd, J = 2.5 Hz, J = 8.5 Hz), 8.02(1H, d, J = 2.5 Hz), 8.09-8.10(1H, m), 8.59(1H, s). |

Now, Test Examples of the present invention are described.

Test Example 1

Upland field soil was put into a 1/300,000 hectare pot, and seeds of various plants were sown. When the respective plants reached predetermined leaf stage ((1) barnyardgrass (*Echinochloa crus-qalli* L.): 0.5 to 2.9 leaf stage, (2) crabgrass (*Digitaria sanquinalis* L.): 0.5 to 3.0 leaf stage, (3) green foxtail (*Setaria viridis* L.): 0.5 to 3.2 leaf stage, (4) wild oat (*Avena fatua* L.): 0.4 to 1.2 leaf stage, (5) italian ryegrass (*Lolium multiflorum* Lam.): 0.4 to 2.0 leaf stage, (6) redroot pigweed (*Amaranthus retroflexus* L.): cotyledon stage to 2.2 leaf stage, (7) rice (*Oryza sativa* L.): 0.2 to 2.7 leaf stage, (8) corn (*Zea mays* L.): 1.7 to 3.6 leaf stage, (9) wheat (*Triticum aestivum* L.): 1.3 to 2.3 leaf stage, (10) soybean (*Glycine max* Merr.); primary leaf stage), wettable powders or emulsifiable concentrates of the compounds of the present invention prepared in accordance with a conventional preparation method, were weighed so as to achieve the prescribed active ingredient amounts, and diluted with water in an amount corresponding to 1,000 liters per 1 hectare (containing 0.1 vol % of an agricultural spreader (surfactant WK manufactured by MARUWA BIO-CHEMICAL Co., Ltd.)), and the spray solutions thus prepared were applied for foliar treatment by a small sprayer.

On the 14th day after the application, the state of growth of the respective plants was visually observed, and the herbicidal effect was evaluated by a growth inhibition rate (%) of 0 (equivalent to the non-treated area) to 100 (complete kill). The results are shown in Table 5.

TABLE 5

| Compound No. | Active ingredient amount g/ha | Growth inhibition rate (%) | | | | | | | | |
|---|---|---|---|---|---|---|---|---|---|---|
| | | Barnyardgrass | Crabgrass | Green foxtail | Wild oat | Italian ryegrass | Redroot pigweed | Rice | Corn | Wheat | Soybean |
| 1-1 | 31 | 100 | 95 | 99 | 98 | 98 | 10 | 80 | 90 | 65 | 0 |
| 1-2 | 31 | 100 | 99 | 99 | 95 | 99 | 0 | 10 | 95 | 20 | 0 |
| 1-3 | 31 | 100 | 99 | 100 | 98 | 98 | 0 | 75 | 99 | 15 | 15 |
| 1-4 | 31 | 99 | 95 | 100 | 99 | 95 | 10 | 20 | 93 | 10 | 35 |
| 1-10 | 31 | 70 | 90 | 90 | 20 | 0 | 0 | 0 | 60 | 0 | 20 |
| 1-13 | 31 | 100 | 95 | 100 | 75 | 70 | 0 | 40 | 88 | 20 | 0 |
| 1-14 | 31 | 98 | 93 | 98 | 95 | 85 | 0 | 80 | 70 | 0 | 0 |
| 1-40 | 31 | 100 | 99 | 100 | 98 | 100 | 40 | 80 | 100 | 93 | 10 |
| 1-41 | 31 | 100 | 99 | 100 | 99 | 100 | 10 | 80 | 98 | 98 | 0 |
| 1-42 | 31 | 100 | 100 | 100 | 100 | 100 | 10 | 88 | 100 | 100 | 10 |
| 1-45 | 31 | 100 | 100 | 100 | 100 | 100 | 10 | 99 | 100 | 99 | 10 |
| 1-46 | 31 | 100 | 100 | 100 | 100 | 99 | 30 | 80 | 98 | 98 | 0 |
| 1-59 | 31 | 100 | 100 | 100 | 99 | 98 | 0 | 40 | 98 | 93 | 0 |
| 1-62 | 31 | 100 | 100 | 100 | 99 | 98 | 0 | 88 | 100 | 90 | 0 |
| 1-65 | 31 | 99 | 100 | 100 | 98 | 98 | 0 | 60 | 98 | 10 | 0 |
| 1-95 | 31 | 100 | 100 | 100 | 99 | 95 | 0 | 80 | 100 | 45 | 0 |
| 1-98 | 31 | 88 | 30 | 60 | 65 | 78 | 0 | 0 | 80 | 20 | 10 |
| 1-130 | 31 | 100 | 99 | 99 | 98 | 93 | 0 | 30 | 95 | 80 | 0 |
| 1-131 | 31 | 100 | 100 | 93 | 93 | 83 | 0 | 30 | 80 | 60 | 0 |
| 1-132 | 31 | 100 | 100 | 100 | 98 | 98 | 0 | 88 | 99 | 98 | 20 |
| 1-133 | 31 | 88 | 0 | 30 | 40 | 0 | 0 | 0 | 0 | 0 | 0 |
| 1-134 | 31 | 98 | 99 | 100 | 99 | 98 | 0 | 88 | 93 | 98 | 0 |
| 1-135 | 31 | 100 | 99 | 100 | 100 | 100 | 0 | 90 | 98 | 100 | 0 |
| 1-136 | 31 | 100 | 98 | 100 | 98 | 98 | 0 | 25 | 99 | 90 | 0 |
| 1-137 | 31 | 100 | 75 | 80 | 93 | 93 | 0 | 85 | 95 | 85 | 15 |
| 1-138 | 31 | 100 | 85 | 60 | 90 | 70 | 0 | 0 | 83 | 83 | 30 |
| 1-139 | 31 | 100 | 80 | 60 | 88 | 98 | 0 | 20 | 50 | 45 | 15 |
| 1-142 | 31 | 90 | 88 | 40 | 85 | 20 | 20 | 15 | 50 | 20 | 40 |
| 1-144 | 31 | 30 | 10 | 60 | 10 | 0 | 0 | 20 | 10 | 0 | 20 |
| 1-145 | 31 | 93 | 90 | 70 | 40 | 20 | 0 | 0 | 40 | 50 | 35 |
| 1-146 | 31 | 98 | 90 | 93 | 88 | 70 | 0 | 0 | 75 | 85 | 10 |
| 1-149 | 31 | 100 | 98 | 100 | 85 | 83 | 10 | 70 | 50 | 20 | 0 |
| 1-150 | 31 | 100 | 100 | 100 | 100 | 100 | 0 | 88 | 95 | 99 | 0 |
| 1-151 | 31 | 99 | 99 | 95 | 95 | 83 | 30 | 65 | 35 | 10 | 0 |
| 1-152 | 31 | 100 | 99 | 100 | 100 | 99 | 0 | 85 | 90 | 88 | 30 |
| 1-157 | 31 | 100 | 100 | 100 | 100 | 99 | 0 | 80 | 100 | 93 | 20 |
| 1-162 | 31 | 100 | 100 | 100 | 100 | 99 | 0 | 93 | 98 | 99 | 0 |
| 1-163 | 31 | 100 | 100 | 100 | 100 | 99 | 0 | 75 | 100 | 60 | 0 |
| 1-165 | 31 | 100 | 100 | 100 | 100 | 100 | 0 | 83 | 100 | 95 | 0 |
| 1-166 | 31 | 95 | 99 | 99 | 93 | 30 | 0 | 10 | 98 | 10 | 15 |
| 1-167 | 31 | 98 | 99 | 100 | 98 | 93 | 0 | 35 | 100 | 40 | 10 |
| 1-169 | 31 | 90 | 95 | 99 | 90 | 90 | 20 | 10 | 98 | 0 | 0 |
| 1-170 | 31 | 95 | 99 | 98 | 40 | 30 | 10 | 40 | 99 | 0 | 0 |
| 1-171 | 31 | 100 | 100 | 100 | 100 | 100 | 0 | 85 | 100 | 83 | 0 |
| 1-173 | 31 | 100 | 100 | 100 | 100 | 95 | 0 | 60 | 99 | 35 | 0 |
| 1-174 | 31 | 100 | 100 | 100 | 100 | 93 | 0 | 20 | 100 | 75 | 0 |
| 2-2 | 31 | 70 | 70 | 75 | 10 | 10 | 20 | 0 | 10 | 0 | 0 |
| 2-3 | 31 | 85 | 15 | 85 | 35 | 20 | 0 | 10 | 10 | 30 | 10 |
| 2-5 | 31 | 100 | 99 | 100 | 95 | 95 | 20 | 85 | 75 | 40 | 0 |
| 2-7 | 31 | 100 | 99 | 100 | 98 | 100 | 50 | 100 | 10 | 98 | 0 |
| 2-8 | 31 | 100 | 100 | 99 | 65 | 83 | 0 | 15 | 10 | 25 | 0 |
| 2-10 | 31 | 99 | 40 | 99 | 10 | 10 | 0 | 0 | 0 | 10 | 30 |
| 2-59 | 31 | 99 | 83 | 83 | 95 | 90 | 0 | 90 | 90 | 40 | 0 |
| 2-60 | 31 | 88 | 85 | 75 | 50 | 40 | 0 | 50 | 50 | 0 | 0 |

TABLE 5-continued

| Compound No. | Active ingredient amount g/ha | Barnyardgrass | Crabgrass | Green foxtail | Wild oat | Italian ryegrass | Redroot pigweed | Rice | Corn | Wheat | Soybean |
|---|---|---|---|---|---|---|---|---|---|---|---|
| 2-61 | 31 | 99 | 78 | 95 | 98 | 93 | 0 | 90 | 95 | 95 | 0 |
| 2-63 | 31 | 100 | 98 | 100 | 100 | 100 | 0 | 90 | 100 | 95 | 0 |
| 2-83 | 31 | 99 | 98 | 99 | 88 | 80 | 0 | 0 | 60 | 10 | 0 |
| 2-84 | 31 | 99 | 100 | 100 | 99 | 93 | 0 | 0 | 90 | 0 | 0 |
| 2-89 | 31 | 95 | 65 | 93 | 0 | 20 | 0 | 10 | 30 | 0 | 20 |
| 2-90 | 31 | 90 | 0 | 75 | 0 | 10 | 0 | 0 | 0 | 20 | 0 |
| 2-92 | 31 | 80 | 30 | 10 | 50 | 78 | 20 | 0 | 80 | 0 | 0 |
| 2-93 | 31 | 100 | 99 | 100 | 30 | 88 | 20 | 0 | 95 | 0 | 10 |
| 2-94 | 31 | 100 | 0 | 100 | 40 | 20 | 0 | 0 | 0 | 0 | 0 |
| 2-101 | 31 | 75 | 85 | 88 | 70 | 50 | 0 | 0 | 80 | 0 | 20 |
| 2-104 | 31 | 85 | 60 | 70 | 35 | 30 | 10 | 10 | 10 | 20 | 10 |
| 2-105 | 31 | 90 | 95 | 90 | 75 | 80 | 0 | 35 | 65 | 25 | 25 |
| 2-108 | 500 | 100 | 85 | 95 | 50 | 10 | 0 | 93 | 10 | 50 | 20 |
| 2-112 | 500 | 99 | 98 | 100 | 90 | 90 | 20 | 93 | 93 | 80 | 0 |
| 2-114 | 31 | 98 | 10 | 80 | 83 | 80 | 0 | 10 | 75 | 25 | 0 |
| 2-115 | 31 | 100 | 95 | 98 | 100 | 98 | 20 | 78 | 98 | 83 | 0 |
| 2-116 | 31 | 100 | 100 | 100 | 100 | 100 | 0 | 90 | 100 | 99 | 10 |
| 2-118 | 31 | 85 | 40 | 60 | 88 | 70 | 0 | 80 | 20 | 50 | 10 |
| 2-121 | 31 | 100 | 98 | 100 | 98 | 98 | 20 | 90 | 20 | 78 | 0 |
| 2-122 | 31 | 100 | 90 | 95 | 60 | 75 | 0 | 0 | 85 | 60 | 40 |
| 2-123 | 31 | 90 | 10 | 83 | 10 | 0 | 0 | 50 | 0 | 90 | 0 |
| 2-124 | 31 | 85 | 80 | 80 | 0 | 0 | 30 | 0 | 0 | 0 | 0 |
| 2-125 | 31 | 100 | 90 | 50 | 90 | 93 | 0 | 70 | 90 | 50 | 0 |
| 2-126 | 31 | 100 | 100 | 100 | 100 | 100 | 0 | 93 | 100 | 99 | 20 |
| 2-127 | 31 | 100 | 30 | 100 | 90 | 78 | 0 | 70 | 0 | 100 | 0 |
| 2-128 | 31 | 85 | 83 | 75 | 88 | 93 | 0 | 45 | 75 | 60 | 0 |
| 2-131 | 31 | 85 | 65 | 98 | 50 | 78 | 10 | 10 | 40 | 45 | 10 |
| 2-132 | 31 | 90 | 50 | 80 | 90 | 78 | — | 40 | 0 | 70 | 30 |
| 2-135 | 31 | 93 | 90 | 95 | 90 | 95 | 0 | 80 | 93 | 88 | 0 |
| 2-138 | 31 | 90 | 65 | 65 | 20 | 20 | 0 | 35 | 15 | 10 | 0 |
| 2-139 | 31 | 90 | 98 | 90 | 98 | 98 | 0 | 98 | 65 | 95 | 10 |
| 2-142 | 500 | 100 | 83 | 90 | 50 | 0 | 0 | 80 | 20 | 50 | 25 |
| 2-146 | 500 | 99 | 95 | 95 | 80 | 20 | 0 | 75 | 85 | 50 | 10 |
| 2-150 | 31 | 100 | 60 | 98 | 50 | 98 | 0 | 30 | 30 | 75 | 0 |
| 2-152 | 31 | 85 | 20 | 85 | 0 | 35 | 0 | 78 | 0 | 75 | 0 |
| 2-154 | 31 | 80 | 10 | 60 | 0 | 10 | 0 | 0 | 0 | 0 | 10 |
| 2-155 | 31 | 78 | 40 | 60 | 0 | 10 | 0 | 0 | 10 | 25 | 0 |
| 2-156 | 31 | 98 | 93 | 98 | 10 | 30 | 0 | 0 | 0 | 0 | 0 |
| 2-158 | 31 | 100 | 93 | 98 | 65 | 65 | 0 | 60 | 0 | 93 | 0 |
| 2-159 | 31 | 100 | 100 | 100 | 100 | 100 | 0 | 100 | 100 | 99 | 35 |
| 2-160 | 31 | 100 | 100 | 100 | 100 | 100 | 0 | 100 | 100 | 99 | 30 |
| 2-161 | 31 | 100 | 83 | 100 | 99 | 99 | 40 | 99 | 90 | 85 | 0 |
| 2-162 | 31 | 100 | 100 | 99 | 100 | 100 | 10 | 100 | 90 | 99 | 0 |
| 2-163 | 31 | 100 | 95 | 100 | 75 | 88 | 0 | 35 | 80 | 10 | 35 |
| 2-164 | 31 | 100 | 100 | 100 | 90 | 95 | 0 | 83 | 90 | 10 | 40 |
| 2-165 | 31 | 100 | 70 | 88 | 0 | 0 | 0 | 25 | 35 | 0 | 25 |
| 2-166 | 31 | 100 | 88 | 100 | 40 | 99 | 20 | 88 | 80 | 10 | 30 |
| 2-167 | 31 | 100 | 99 | 100 | 45 | 80 | 0 | 60 | 90 | 25 | 30 |
| 2-169 | 31 | 100 | 100 | 100 | 88 | 85 | 0 | 83 | 98 | 85 | 40 |
| 2-171 | 31 | 99 | 90 | 93 | 0 | 30 | 0 | 25 | 80 | 0 | 30 |
| 2-172 | 31 | 100 | 98 | 99 | 40 | 35 | 0 | 30 | 98 | 10 | 40 |
| 2-173 | 31 | 99 | 95 | 88 | 35 | 90 | 0 | 85 | 65 | 75 | 0 |
| 2-174 | 31 | 100 | 93 | 93 | 88 | 95 | — | 93 | 95 | 93 | 0 |
| 2-175 | 31 | 98 | 98 | 99 | 10 | 50 | 0 | 0 | 95 | 0 | 10 |
| 2-176 | 31 | 100 | 99 | 100 | 25 | 85 | 0 | 10 | 80 | 0 | 0 |
| 2-177 | 31 | 100 | 100 | 99 | 98 | 98 | 0 | 65 | 83 | 90 | 30 |
| 2-178 | 31 | 100 | 100 | 100 | 95 | 98 | 0 | 15 | 83 | 75 | 0 |
| 2-179 | 31 | 88 | 98 | 100 | 0 | 0 | 0 | 0 | 75 | 10 | 0 |
| 2-181 | 31 | 100 | 99 | 100 | 83 | 93 | 0 | 10 | 70 | 35 | 0 |
| 2-183 | 31 | 95 | 98 | 98 | 95 | 98 | 0 | 90 | 50 | 90 | 30 |
| 2-184 | 31 | 95 | 95 | 99 | 30 | 35 | 0 | 60 | 40 | 10 | 30 |
| 2-185 | 31 | 93 | 85 | 88 | 0 | 0 | 0 | 0 | 10 | 0 | 20 |
| 2-186 | 31 | 90 | 99 | 99 | 25 | 0 | 0 | 0 | 98 | 0 | 15 |
| 2-193 | 31 | 70 | 90 | 93 | 0 | 0 | 0 | 0 | 65 | 0 | 0 |
| 2-194 | 31 | 85 | 90 | 90 | 10 | 35 | 0 | 0 | 60 | 0 | 10 |
| 2-195 | 31 | 93 | 90 | 93 | 90 | 85 | 0 | 40 | 83 | 35 | 30 |
| 3-1 | 31 | 100 | 99 | 100 | 98 | 100 | 50 | 100 | 10 | 98 | 0 |
| 3-33 | 31 | 100 | 99 | 100 | 100 | 98 | 0 | 93 | 10 | 100 | 30 |
| 3-34 | 31 | 100 | 95 | 100 | 95 | 99 | 0 | 90 | 15 | 90 | 30 |
| 3-35 | 31 | 100 | 99 | 99 | 100 | 99 | 10 | 95 | 60 | 100 | 25 |
| 3-36 | 31 | 100 | 99 | 99 | 99 | 99 | 0 | 90 | 40 | 99 | 40 |
| 3-37 | 31 | 100 | 99 | 100 | 98 | 99 | 10 | 95 | 45 | 99 | 30 |
| 3-38 | 31 | 100 | 100 | 100 | 98 | 99 | 20 | 80 | 30 | 98 | 25 |
| 3-39 | 31 | 88 | 0 | 95 | 0 | 0 | 0 | 0 | 15 | 0 | 0 |
| 3-40 | 31 | 99 | 99 | 99 | 98 | 98 | 0 | 85 | 25 | 98 | 10 |

TABLE 5-continued

| Active ingredient | | Growth inhibition rate (%) | | | | | | | | | |
|---|---|---|---|---|---|---|---|---|---|---|---|
| Compound No. | amount g/ha | Barnyardgrass | Crabgrass | Green foxtail | Wild oat | Italian ryegrass | Redroot pigweed | Rice | Corn | Wheat | Soybean |
| 3-41 | 31 | 100 | 95 | 99 | 98 | 99 | 20 | 10 | 20 | 99 | 0 |
| 3-42 | 31 | 100 | 20 | 98 | 100 | 95 | 10 | 60 | 30 | 20 | 0 |
| 3-43 | 31 | 100 | 98 | 100 | 98 | 98 | 0 | 80 | 40 | 95 | 10 |
| 3-44 | 31 | 100 | 99 | 100 | 100 | 98 | 0 | 85 | 20 | 85 | 10 |
| 3-45 | 31 | 100 | 99 | 99 | 100 | 100 | 0 | 98 | 45 | 98 | 25 |
| 3-46 | 31 | 100 | 99 | 100 | 100 | 100 | 20 | 98 | 50 | 98 | 35 |
| 3-47 | 31 | 100 | 99 | 100 | 99 | 99 | 0 | 30 | 40 | 98 | 20 |
| 3-48 | 31 | 100 | 98 | 100 | 75 | 95 | 0 | 0 | 25 | 90 | 10 |
| 3-49 | 31 | 99 | 100 | 100 | 98 | 100 | 0 | 50 | 45 | 99 | 20 |
| 3-50 | 31 | 100 | 98 | 100 | 98 | 93 | 0 | 60 | 15 | 99 | 10 |
| 3-51 | 31 | 99 | 100 | 100 | 99 | 99 | 0 | 60 | 60 | 99 | 30 |
| 3-52 | 31 | 100 | 95 | 100 | 20 | 90 | 0 | 70 | 35 | 10 | 20 |
| 3-53 | 31 | 100 | 93 | 95 | 60 | 65 | 0 | 40 | 0 | 0 | 0 |
| 3-54 | 31 | 100 | 98 | 100 | 78 | 95 | 0 | 20 | 30 | 93 | 20 |
| 3-55 | 31 | 98 | 99 | 100 | 99 | 99 | 0 | 90 | 50 | 98 | 30 |
| 3-56 | 31 | 98 | 99 | 100 | 99 | 98 | 0 | 0 | 40 | 93 | 30 |
| 3-57 | 31 | 100 | 99 | 100 | 99 | 95 | 0 | 0 | 25 | 95 | 25 |
| 3-58 | 31 | 100 | 99 | 100 | 95 | 99 | 0 | 50 | 55 | 98 | 25 |
| 3-59 | 31 | 99 | 98 | 100 | 93 | 93 | 0 | 0 | 0 | 65 | 20 |
| 3-60 | 31 | 99 | 95 | 100 | 98 | 95 | 0 | 10 | 20 | 93 | 10 |
| 3-61 | 31 | 0 | 20 | 60 | 0 | 0 | 0 | 0 | 20 | 0 | 0 |
| 3-62 | 31 | 100 | 99 | 99 | 99 | 93 | 0 | 0 | 60 | 90 | 20 |
| 3-63 | 31 | 100 | 98 | 100 | 98 | 90 | 0 | 0 | 40 | 83 | 0 |
| 3-64 | 31 | 98 | 90 | 100 | 83 | 85 | 0 | 0 | 50 | 60 | 0 |
| 3-65 | 31 | 100 | 83 | 99 | 75 | 85 | 0 | 0 | 40 | 98 | 10 |
| 3-66 | 31 | 10 | 20 | 35 | 50 | 40 | 0 | 0 | 25 | 10 | 0 |
| 3-67 | 31 | 100 | 95 | 100 | 100 | 99 | 0 | 40 | 50 | 99 | 0 |
| 3-68 | 31 | 100 | 95 | 100 | 90 | 83 | 0 | 0 | 20 | 30 | 0 |
| 3-69 | 31 | 100 | 95 | 100 | 99 | 99 | 0 | 30 | 20 | 98 | 0 |
| 3-70 | 31 | 98 | 88 | 98 | 60 | 40 | 0 | 0 | 30 | 0 | 10 |
| 3-71 | 31 | 100 | 90 | 100 | 99 | 98 | 0 | 15 | 0 | 95 | 0 |
| 3-74 | 31 | 93 | 20 | 95 | 25 | 0 | 0 | 0 | 20 | 0 | 0 |
| 3-75 | 31 | 99 | 95 | 99 | 98 | 98 | 0 | 0 | 10 | 95 | 0 |
| 3-76 | 31 | 93 | 30 | 93 | 0 | 10 | 0 | 0 | 0 | 0 | 0 |
| 3-77 | 31 | 100 | 90 | 100 | 60 | 85 | 0 | 0 | 30 | 25 | 0 |
| 3-78 | 31 | 99 | 93 | 98 | 40 | 10 | 0 | 0 | 0 | 0 | 0 |
| 3-79 | 31 | 100 | 98 | 100 | 98 | 99 | 0 | 99 | 50 | 93 | 30 |
| 3-80 | 31 | 100 | 95 | 99 | 99 | 93 | 0 | 0 | 25 | 90 | 25 |
| 3-81 | 31 | 99 | 93 | 99 | 95 | 95 | 0 | 0 | 0 | 25 | 0 |
| 3-82 | 31 | 100 | 98 | 100 | 98 | 98 | 10 | 93 | 35 | 98 | 0 |
| 3-96 | 31 | 100 | 100 | 100 | 98 | 99 | 0 | 95 | 20 | 95 | 0 |
| 3-97 | 31 | 100 | 100 | 100 | 100 | 99 | 0 | 75 | 15 | 95 | 0 |

Test Example 2

Upland field soil was put into a 1/300,000 hectare pot, and seeds of various plants (barnyardgrass (*Echinochloa crusqalli* L.), crabgrass (*Digitaris sanquinalis* L.), green foxtail (*Setaria viridis* L.), redroot pigweed (*Amaranthus retroflexus* L.), prickly sida (*Sida spinosa* L.), velvetleaf (*Abutilon theophrasti* MEDIC.), rice (*Oryza sativa* L.), corn (*Zea mays* L.), wheat (*Triticum aestivum* L.), soybean (*Glycine max* Merr.)) were sown. On the day after sowing, wettable powders or emulsifiable concentrates of the compounds of the present invention prepared in accordance with a conventional preparation method, were weighed so as to achieve the prescribed active ingredient amounts, and diluted with water in an amount corresponding to 1,000 liters per 1 hectare, followed by soil application by a small sprayer.

On the 14th day after the application, the state of growth of the respective plants was visually observed, and the herbicidal effect was evaluated by a growth inhibition rate (%) of 0 (equivalent to the non-treated area) to 100 (complete kill). The results are shown in Table 6.

TABLE 6

| Active ingredient | | Growth inhibition rate (%) | | | | | | | | | |
|---|---|---|---|---|---|---|---|---|---|---|---|
| Compound No. | amount g/ha | Barnyardgrass | Crabgrass | Green foxtail | Redroot pigweed | Prickly sida | Velvetleaf | Rice | Corn | Wheat | Soybean |
| 1-1 | 31 | 85 | 100 | 100 | 0 | 0 | 0 | 20 | 50 | 0 | 0 |
| 1-2 | 31 | 98 | 98 | 99 | — | 30 | 0 | 20 | 20 | 10 | 0 |
| 1-3 | 31 | 100 | 100 | 100 | 0 | 0 | 0 | 80 | 90 | 35 | 0 |
| 1-4 | 31 | 100 | 99 | 98 | 0 | 0 | 0 | 40 | 0 | 0 | 0 |
| 1-14 | 31 | 99 | 83 | 93 | 0 | 0 | 0 | 0 | 0 | 0 | 0 |
| 1-40 | 31 | 100 | 100 | 100 | 0 | 0 | 0 | 60 | 30 | 0 | 0 |
| 1-41 | 31 | 100 | 100 | 100 | 0 | 0 | 0 | 0 | 20 | 0 | 0 |
| 1-42 | 31 | 100 | 100 | 100 | 0 | 0 | 0 | 80 | 40 | 0 | 0 |

TABLE 6-continued

| Active ingredient | | Growth inhibition rate (%) | | | | | | | | | |
|---|---|---|---|---|---|---|---|---|---|---|---|
| Compound No. | amount g/ha | Barnyardgrass | Crabgrass | Green foxtail | Redroot pigweed | Prickly sida | Velvetleaf | Rice | Corn | Wheat | Soybean |
| 1-45 | 31 | 100 | 100 | 100 | 0 | 0 | 0 | 30 | 88 | 20 | 0 |
| 1-46 | 31 | 80 | 90 | 99 | 0 | 0 | 0 | 30 | 0 | 30 | 0 |
| 1-59 | 31 | 100 | 100 | 99 | 0 | 0 | 0 | 20 | 0 | 0 | 0 |
| 1-62 | 31 | 100 | 100 | 99 | 0 | 0 | 0 | 20 | 0 | 0 | 0 |
| 1-65 | 31 | 100 | 100 | 99 | 0 | 0 | 0 | 20 | 0 | 0 | 0 |
| 1-95 | 31 | 100 | 100 | 100 | 0 | 0 | 0 | 50 | 80 | 0 | 0 |
| 1-98 | 31 | 95 | 20 | 30 | 0 | 0 | 0 | 35 | 0 | 0 | 0 |
| 1-132 | 31 | 99 | 93 | 98 | 0 | 0 | 0 | 0 | 10 | 0 | 0 |
| 1-149 | 31 | 98 | 99 | 100 | 0 | 0 | 0 | 0 | 0 | 0 | 0 |
| 1-150 | 31 | 99 | 98 | 98 | 0 | 0 | 0 | 0 | 0 | 0 | 0 |
| 1-152 | 31 | 80 | 35 | 85 | 0 | 0 | 0 | 0 | 10 | 0 | 10 |
| 1-157 | 31 | 100 | 99 | 100 | 0 | 0 | 0 | 40 | 0 | 0 | 30 |
| 1-162 | 31 | 100 | 100 | 100 | 0 | 0 | 0 | 95 | 40 | 0 | 0 |
| 1-163 | 31 | 100 | 100 | 100 | 0 | 0 | 0 | 40 | 80 | 0 | 0 |
| 1-165 | 31 | 99 | 100 | 95 | 0 | 0 | 0 | 0 | 0 | 0 | 0 |
| 1-166 | 31 | 80 | 95 | 80 | 0 | 0 | 0 | 0 | 0 | 0 | 0 |
| 1-167 | 31 | 85 | 100 | 95 | 0 | 0 | 0 | 0 | 0 | 0 | 0 |
| 1-170 | 31 | 75 | 93 | 98 | 0 | 0 | 0 | 0 | 0 | 0 | 0 |
| 1-171 | 31 | 100 | 100 | 100 | 0 | 0 | 0 | 0 | 0 | 0 | 0 |
| 1-173 | 31 | 100 | 100 | 100 | 0 | 0 | 0 | 60 | 50 | 0 | 0 |
| 1-174 | 31 | 100 | 100 | 100 | 0 | 0 | 0 | 0 | 0 | 0 | 0 |
| 2-3 | 31 | 50 | 80 | 98 | 0 | 0 | 0 | 20 | 0 | 0 | 0 |
| 2-5 | 31 | 100 | 100 | 100 | 0 | 0 | 0 | 80 | 65 | 30 | 0 |
| 2-7 | 31 | 99 | 99 | 100 | 0 | 0 | 0 | 40 | 20 | 25 | 0 |
| 2-8 | 31 | 100 | 95 | 100 | 0 | 0 | 0 | 20 | 0 | 0 | 0 |
| 2-10 | 31 | 95 | 50 | 85 | 0 | 0 | 0 | 40 | 30 | 0 | 0 |
| 2-59 | 31 | 75 | 70 | 40 | 0 | 0 | 0 | 0 | 0 | 0 | 0 |
| 2-61 | 31 | 65 | 50 | 98 | 0 | 0 | 0 | 0 | 0 | 0 | 0 |
| 2-63 | 31 | 100 | 100 | 98 | 0 | 0 | 0 | 15 | 0 | 0 | 0 |
| 2-83 | 31 | 99 | 100 | 100 | 100 | 75 | 0 | 30 | 0 | 0 | 0 |
| 2-84 | 31 | 100 | 100 | 100 | 0 | 0 | 0 | 60 | 0 | 0 | 0 |
| 2-89 | 31 | 95 | 30 | 50 | 0 | 0 | 0 | 30 | 0 | 0 | 0 |
| 2-93 | 31 | 100 | 99 | 99 | 0 | 0 | 0 | 0 | 0 | 0 | 0 |
| 2-101 | 31 | 78 | 93 | 95 | 0 | 0 | 0 | 0 | 20 | 10 | 0 |
| 2-108 | 500 | 100 | 98 | 93 | 0 | 0 | 0 | 93 | 0 | 0 | 0 |
| 2-112 | 500 | 100 | 100 | 100 | 0 | 0 | 0 | 70 | 0 | 20 | 0 |
| 2-116 | 31 | 100 | 100 | 100 | 0 | 0 | 0 | 0 | 85 | 60 | 0 |
| 2-121 | 31 | 100 | 98 | 100 | 0 | 0 | 0 | 0 | 20 | 0 | 0 |
| 2-126 | 31 | 100 | 98 | 100 | 0 | 0 | 0 | 0 | 30 | 10 | 0 |
| 2-127 | 31 | 93 | 10 | 78 | 0 | 0 | 0 | 0 | 0 | 0 | 0 |
| 2-135 | 31 | 90 | 75 | 90 | 0 | 0 | 0 | 0 | 0 | 0 | 10 |
| 2-138 | 31 | 93 | 83 | 90 | 0 | 0 | 0 | 25 | 0 | 0 | 0 |
| 2-142 | 500 | 100 | 98 | 93 | 0 | 0 | 0 | 90 | 0 | 0 | 0 |
| 2-146 | 500 | 100 | 100 | 100 | 0 | 0 | 50 | 85 | 20 | 0 | 0 |
| 2-150 | 31 | 100 | 90 | 98 | 100 | 75 | 0 | 0 | 0 | 0 | 0 |
| 2-155 | 31 | 85 | 83 | 88 | 0 | 0 | 0 | 70 | 0 | 0 | 0 |
| 2-156 | 31 | 83 | 75 | 98 | 0 | 0 | 0 | 15 | 0 | 0 | 0 |
| 2-158 | 31 | 80 | 70 | 95 | 0 | 0 | 0 | 0 | 10 | 0 | 0 |
| 2-159 | 31 | 100 | 98 | 99 | 0 | 0 | 0 | 0 | 0 | 0 | 0 |
| 2-160 | 31 | 100 | 99 | 100 | 95 | 50 | 0 | 0 | 0 | 0 | 0 |
| 2-161 | 31 | 98 | 0 | 0 | 0 | 0 | 0 | 0 | 0 | 0 | 0 |
| 2-162 | 31 | 90 | 20 | 20 | — | — | 0 | 0 | 0 | 20 | 0 |
| 2-163 | 31 | 98 | 98 | 99 | 0 | 0 | 0 | 20 | 15 | 20 | 0 |
| 2-164 | 31 | 50 | 98 | 90 | 0 | 0 | 0 | 0 | 0 | 0 | 0 |
| 2-165 | 31 | 99 | 98 | 99 | 0 | 0 | 0 | 70 | 0 | 0 | 0 |
| 2-166 | 31 | 99 | 95 | 100 | 0 | 0 | 0 | 70 | 0 | 0 | 0 |
| 2-167 | 31 | 40 | 99 | 100 | — | 0 | 0 | 0 | 0 | 0 | 0 |
| 2-169 | 31 | 70 | 98 | 98 | 0 | 0 | 0 | 0 | 0 | 0 | 0 |
| 2-171 | 31 | 65 | 30 | 75 | 0 | 0 | 0 | 0 | 0 | 0 | 0 |
| 2-172 | 31 | 60 | 30 | 20 | 0 | 0 | 0 | 0 | 0 | 0 | 0 |
| 2-173 | 31 | 65 | 80 | 10 | 0 | 0 | 0 | 20 | 10 | 0 | 0 |
| 2-174 | 31 | 20 | 80 | 0 | 0 | 0 | 0 | 0 | 20 | 0 | 0 |
| 2-175 | 31 | 100 | 95 | 99 | 0 | 0 | 0 | 90 | 30 | 0 | 0 |
| 2-176 | 31 | 100 | 98 | 99 | 0 | 0 | 0 | 60 | 0 | 0 | 0 |
| 2-177 | 31 | 90 | 98 | 90 | 0 | 0 | 0 | 30 | 0 | 0 | 0 |
| 2-181 | 31 | 90 | 0 | 40 | 0 | 0 | 0 | 20 | 0 | 0 | 0 |
| 2-194 | 31 | 95 | 83 | 99 | 0 | 0 | 0 | 30 | 40 | 0 | 0 |
| 2-195 | 31 | 98 | 98 | 99 | 0 | 0 | 0 | 20 | 0 | 0 | 0 |
| 3-1 | 31 | 99 | 99 | 100 | 0 | 0 | 0 | 40 | 20 | 25 | 0 |
| 3-33 | 31 | 100 | 99 | 100 | 0 | 0 | 0 | 60 | 20 | 40 | 0 |
| 3-34 | 31 | 99 | 65 | 98 | 0 | 0 | 0 | 20 | 20 | 0 | 0 |
| 3-40 | 31 | 90 | 10 | 40 | 0 | 0 | 0 | 10 | 10 | 0 | 0 |
| 3-45 | 31 | 95 | 20 | 85 | 0 | 0 | 0 | 25 | 0 | 0 | 0 |
| 3-48 | 31 | 98 | 60 | 100 | 0 | 0 | 0 | 0 | 0 | 20 | 0 |
| 3-49 | 31 | 95 | 20 | 85 | 0 | 0 | 0 | 0 | 0 | 10 | 0 |

TABLE 6-continued

| Compound No. | Active ingredient amount g/ha | Barnyardgrass | Crabgrass | Green foxtail | Redroot pigweed | Prickly sida | Velvetleaf | Rice | Corn | Wheat | Soybean |
|---|---|---|---|---|---|---|---|---|---|---|---|
| 3-50 | 31 | 99 | 80 | 98 | 0 | 0 | 0 | 0 | 0 | 0 | 0 |
| 3-51 | 31 | 99 | 95 | 100 | 0 | 0 | 0 | 0 | 0 | 0 | 0 |
| 3-52 | 31 | 99 | 95 | 100 | 0 | 0 | 0 | 0 | 0 | 0 | 0 |
| 3-54 | 31 | 99 | 30 | 98 | 0 | 0 | 0 | 0 | 0 | 0 | 0 |
| 3-55 | 31 | 80 | 30 | 60 | 0 | 0 | 0 | 0 | 0 | 0 | 0 |
| 3-57 | 31 | 90 | 30 | 95 | 0 | 0 | 0 | 0 | 40 | 0 | 30 |
| 3-58 | 31 | 85 | 10 | 75 | 0 | 0 | 0 | 0 | 0 | 0 | 0 |
| 3-59 | 31 | 85 | 0 | 80 | 0 | 0 | 0 | 0 | 0 | 0 | 0 |
| 3-64 | 31 | 98 | 50 | 93 | 0 | 0 | 0 | 0 | 0 | 0 | 0 |
| 3-69 | 31 | 93 | 30 | 95 | 0 | 0 | 0 | 0 | 0 | 0 | 0 |
| 3-79 | 31 | 100 | 95 | 100 | 0 | 0 | 0 | 0 | 0 | 0 | 0 |
| 3-82 | 31 | 99 | 85 | 99 | 0 | 0 | 0 | 0 | 0 | 0 | 0 |
| 3-96 | 31 | 99 | 98 | 85 | 0 | 0 | 0 | 75 | 0 | 0 | 0 |
| 3-97 | 31 | 95 | 93 | 99 | 0 | 0 | 0 | 20 | 0 | 20 | 0 |

Now, Formulation Examples of the present invention will be described.

Formulation Example 1

| | | |
|---|---|---|
| (1) | The compound of the present invention | 75 parts by weight |
| (2) | Geropon T-77 (tradename, manufactured by Rhone-Poulenc) | 14.5 parts by weight |
| (3) | NaCl | 10 parts by weight |
| (4) | Dextrin | 0.5 part by weight |

The above components (1) to (4) are put into a high speed mixing granulator, and 20% of water is further added thereto, followed by granulation and drying to obtain water-dispersed granules.

Formulation Example 2

| | | |
|---|---|---|
| (1) | Kaolin | 78 parts by weight |
| (2) | Laveline FAN (tradename, manufactured by DAI-ICHI KOGYO SEIYAKU CO., LTD.) | 2 parts by weight |
| (3) | Sorpol 5039 (tradename, manufactured by TOHO Chemical Industry Co., Ltd.) | 5 parts by weight |
| (4) | Carplex (tradename, manufactured by DSL. Japan Co., Ltd.) | 15 parts by weight |

The mixture of the above components (1) to (4) and the compound of the present invention are mixed in a weight ratio of 9:1 to obtain a wettable powder.

Formulation Example 3

| | | |
|---|---|---|
| (1) | Hi-Filler No. 10 (tradename, manufactured by Matsumura Sangyo Co., Ltd.) | 33 parts by weight |
| (2) | Sorpol 5050 (tradename, manufactured by TOHO Chemical Industry Co., Ltd.) | 3 parts by weight |
| (3) | Sorpol 5073 (tradename, manufactured by TOHO Chemical Industry Co., Ltd.) | 4 parts by weight |
| (4) | The compound of the present invention | 60 parts by weight |

The above components (1) to (4) are mixed to obtain a wettable powder.

Formulation Example 4

| | | |
|---|---|---|
| (1) | The compound of the present invention | 4 parts by weight |
| (2) | Bentonite | 30 parts by weight |
| (3) | Calcium carbonate | 61.5 parts by weight |
| (4) | Toxanon GR-31A (tradename, manufactured by Sanyo Chemical Industries Co., Ltd.) | 3 parts by weight |
| (5) | Calcium lignin sulfonate | 1.5 parts by weight |

Pulverized component (1) and components (2) and (3) are preliminarily mixed, and then components (4) and (5) and water are added thereto and mixed. The mixture is extruded and granulated, followed by drying and sieving to obtain granules.

Formulation Example 5

| | | |
|---|---|---|
| (1) | The compound of the present invention | 30 parts by weight |
| (2) | Zeeklite (tradename, manufactured by Zeeklite Co., Ltd.) | 60 parts by weight |
| (3) | New Kalgen WG-1 (tradename, manufactured by TAKEMOTO OIL & FAT CO., LTD.) | 5 parts by weight |
| (4) | New Kalgen FS-7 (tradename, manufactured by TAKEMOTO OIL & FAT CO., LTD.) | 5 parts by weight |

Components (1), (2) and (3) are mixed and passed through a pulverizer, and then component (4) is added thereto. The mixture is kneaded and then extruded and granulated, followed by drying and sieving to obtain water dispersible granules.

Formulation Example 6

| | | |
|---|---|---|
| (1) | The compound of the present invention | 28 parts by weight |
| (2) | Soprophor FL (tradename, manufactured by Rhone-Poulenc) | 2 parts by weight |
| (3) | Sorpol 335 (tradename, manufactured by TOHO Chemical Industry Co., Ltd.) | 1 part by weight |
| (4) | IP solvent 1620 (tradename, manufactured by Idemitsu Petrochemical Co., Ltd.) | 32 parts by weight |
| (5) | Ethylene glycol | 6 parts by weight |
| (6) | Water | 31 parts by weight |

The above components (1) to (6) are mixed and pulverized by a wet-grinding machine (Dyno-mill) to obtain a water-based suspension concentrate.

The present invention is by no means limited to the above-described embodiments, and various modifications are possible within the claimed range of the present invention. Also, embodiments obtainable by suitably combining technical means disclosed respectively in different embodiments, will be included in the present invention. Further, by combining technical means disclosed respectively in the respective embodiments, it is possible to form a new technical feature.

INDUSTRIAL APPLICABILITY

The compound of the present invention realizes a remarkable improvement in herbicidal activities against undesirable plants, as compared with similar conventional compounds. Further, it is highly safe to crop plants. Thus, the pyridazinone compound of the present invention or its salt, exhibits excellent herbicidal effects, when used as an active ingredient of a herbicide. Its application range covers various fields including agricultural fields such as paddy field, dry field, horticultural field, mulberry field, etc. and non-agricultural fields such as mountain forest, agricultural roads, grounds, plant sites, etc. Its application method may also be suitably selected for use, among soil treatment, foliar treatment, irrigation treatment, etc.

The entire disclosure of Japanese Patent Application No. 2016-067797 filed on Mar. 30, 2016 including specification, claims, figures and abstract is incorporated herein by reference in its entirety.

The invention claimed is:
1. A pyridazinone compound represented by the formula (I) or its salt:

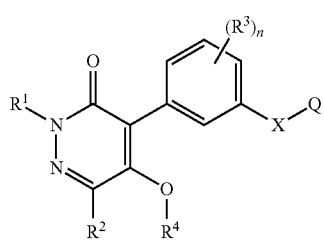

wherein X is —O— and Q is bicyclic heteroaryl which may be substituted by Z; or X is —S—, —SO—, —SO$_2$— or —N(Y)— and Q is monocyclic aryl which may be substituted by Z, monocyclic heteroaryl which may be substituted by Z, bicyclic aryl which may be substituted by Z, or bicyclic heteroaryl which may be substituted by Z Y is a hydrogen atom or alkyl;
$R^1$ is alkyl, alkenyl, alkynyl, cycloalkyl, cycloalkylalkyl, haloalkyl, monocyclic aryl which may be substituted by Z, monocyclic arylalkyl which may be substituted by Z, alkylthioalkyl, alkylsulfinylalkyl, alkylsulfonylalkyl, dialkylaminoalkyl, alkoxyalkyl, amino, nitro, alkylcarbonylalkyl, alkoxycarbonylalkyl or hydroxycarbonylalkyl;
$R^2$ is a hydrogen atom, alkyl, haloalkyl, cycloalkyl, halogen, alkoxy, alkylthio, alkylsulfinyl, alkyl sulfonyl or cyano;
$R^3$ is halogen, hydroxy, alkyl, haloalkyl, alkenyl, haloalkenyl, alkynyl, haloalkynyl, alkoxy, haloalkoxy, nitro, amino, alkylcarbonyl or cycloalkyl;
$R^4$ is a hydrogen atom, alkyl, —C(O)R$^6$, —C(S)R$^6$, —SR$^7$, —SOR$^7$, —SO$_2$R$^7$, monocyclic arylalkyl which may be substituted by Z, alkoxyalkyl, —CH(J$^1$)OCOOJ$^2$, alkylcarbonylalkyl, monocyclic aryl which may be substituted by Z, monocyclic arylcarbonylalkyl which may be substituted by Z, alkenyl, alkoxyalkoxyalkyl, alkoxycarbonylalkyl, alkynyl, cyanoalkyl, haloalkoxyalkyl or dialkylaminoalkyl;
$R^6$ is alkyl, alkoxy, morpholino, dialkylamino, (monocyclic aryl which may be substituted by Z)(alkyl)amino, cycloalkyl, alkoxyalkyl, alkylthioalkyl, haloalkyl, alkylthio, alkenyl, alkynyl, alkoxycarbonylalkyl, cycloalkylalkyl, cyanoalkyl, alkoxyalkoxyalkyl, monocyclic aryl which may be substituted by Z, monocyclic heteroaryl which may be substituted by Z, monocyclic arylalkyl which may be substituted by Z, monocyclic aryloxy which may be substituted by Z, monocyclic arylthio which may be substituted by Z, monocyclic aryloxyalkyl which may be substituted by Z, monocyclic arylthioalkyl which may be substituted by Z, alkoxycarbonyl, alkoxyalkoxy, haloalkoxy, haloalkoxyalkoxy, alkylthioalkoxy, cycloalkoxyalkoxy, monocyclic arylalkoxy which may be substituted by Z, monocyclic aryloxyalkoxy which may be substituted by Z, monocyclic heteroaryloxyalkoxy which may be substituted by Z, alkenyloxyalkoxy, alkoxyalkoxyalkoxy, alkynyloxy, alkenyloxy, haloalkenyl, dialkylaminoalkyl, alkylthioalkoxyalkoxy, cycloalkylalkoxy, cycloalkylalkoxyalkoxy, monocyclic arylalkoxyalkoxy which may be substituted by Z, monocyclic heteroarylalkoxyalkoxy which may be substituted by Z or cycloalkoxy which may be substituted by Z;
$R^7$ is alkyl, haloalkyl, cycloalkyl or monocyclic aryl which may be substituted by Z;
Z is halogen, alkyl, haloalkyl, alkoxy, haloalkoxy, cycloalkyl, cyano, nitro, —C(O)OR$^5$, formyl, alkylthio, alkylsulfinyl, alkyl sulfonyl, —CH=NOJ$^3$ or dialkylaminocarbonyl;
$R^5$ is a hydrogen atom or alkyl;
$J^1$ is a hydrogen atom or alkyl;
$J^2$ is alkyl or cycloalkyl;
$J^3$ is a hydrogen atom, alkylcarbonyl or alkoxyalkyl; and
n is an integer of from 0 to 4.
2. The pyridazinone compound or its salt according to claim 1, wherein in the formula (I), X is —O— and Q is bicyclic heteroaryl which may be substituted by Z; or X is —S—, —SO—, —SO$_2$— or —N(Y)— and Q is monocyclic aryl which may be substituted by Z, monocyclic heteroaryl which may be substituted by Z, bicyclic aryl which may be substituted by Z, or bicyclic heteroaryl which may be substituted by Z
Y is a hydrogen atom or alkyl;
Z is halogen, alkyl, haloalkyl, cyano, nitro or —C(O)OR$^5$;
$R^1$ is alkyl, alkenyl, alkynyl or cycloalkyl;
$R^2$ is a hydrogen atom, alkyl, haloalkyl or cycloalkyl;
$R^3$ is halogen, alkyl, haloalkyl, alkenyl, haloalkenyl, alkynyl, haloalkynyl, alkoxy, haloalkoxy or cycloalkyl;
$R^4$ is a hydrogen atom, alkyl, —C(O)R$^6$ or —SO$_2$R$^7$;
$R^5$ is a hydrogen atom or alkyl;
$R^6$ is alkyl, alkoxy or morpholino;
$R^7$ is alkyl; and
n is an integer of from 1 to 4.

3. A herbicide containing the pyridazinone compound or its salt as defined in claim 1 as an active ingredient.

4. A method for controlling undesired plants or inhibiting their growth, which comprises applying a herbicidally effective amount of the pyridazinone compound or its salt as defined in claim 1 to the undesired plants or to a place where they grow.

5. The method according to claim 4, wherein the application amount of the pyridazinone compound or its salt is from 0.1 to 5,000 g/ha.

* * * * *